(12) United States Patent
Mayse

(10) Patent No.: US 11,571,555 B2
(45) Date of Patent: Feb. 7, 2023

(54) AUTOMATIC PLEURAL-PERITONAL PUMP

(71) Applicant: Pleural Dynamics, Inc., Wayzata, MN (US)

(72) Inventor: Martin L. Mayse, Wayzata, MN (US)

(73) Assignee: Pleural Dynamics, Inc., Wayzata, MN (US)

( * ) Notice: Subject to any disclaimer, the term of this patent is extended or adjusted under 35 U.S.C. 154(b) by 129 days.

(21) Appl. No.: 16/819,352

(22) Filed: Mar. 16, 2020

(65) Prior Publication Data

US 2021/0283330 A1    Sep. 16, 2021

(51) Int. Cl.
| | | |
|---|---|---|
| *A61M 27/00* | (2006.01) | |
| *A61M 5/142* | (2006.01) | |
| *A61M 39/24* | (2006.01) | |
| *A61M 5/168* | (2006.01) | |
| *A61M 1/00* | (2006.01) | |

(52) U.S. Cl.
CPC ............ *A61M 27/002* (2013.01); *A61M 1/71* (2021.05); *A61M 1/84* (2021.05); *A61M 5/14276* (2013.01); *A61M 5/16804* (2013.01); *A61M 39/24* (2013.01); *A61M 2039/2406* (2013.01); *A61M 2205/3334* (2013.01); *A61M 2205/3379* (2013.01); *A61M 2205/8206* (2013.01); *A61M 2210/101* (2013.01); *A61M 2210/1017* (2013.01)

(58) Field of Classification Search
CPC ............... A61M 27/002; A61M 1/82
See application file for complete search history.

(56) References Cited

U.S. PATENT DOCUMENTS

| | | | |
|---|---|---|---|
| 3,233,610 A | 2/1966 | Charles | |
| 3,683,929 A | 8/1972 | Holter | |
| 4,487,603 A | 12/1984 | Harris | |
| 4,588,394 A * | 5/1986 | Schulte | A61M 5/1428 604/9 |
| 4,725,207 A | 2/1988 | Buchwald et al. | |
| 4,850,955 A * | 7/1989 | Newkirk | A61M 27/002 604/9 |
| 5,009,635 A | 4/1991 | Scarberry | |

(Continued)

OTHER PUBLICATIONS

"International Application Serial No. PCT US2021 021643, International Search Report dated Jun. 22, 2021", 2 pgs.

(Continued)

*Primary Examiner* — Jenna Zhang
(74) *Attorney, Agent, or Firm* — Schwegman Lundberg & Woessner, P.A.

(57) ABSTRACT

An automatic pump-based fluid management system, as described herein, comprises an intercostal pump that is, generally, a resiliently flexible bulb having an inlet and an outlet. The inlet is attached to a first tube that extends from the intercostal pump to a first area of a patient's body, for example, the patient's pleural cavity. The outlet is connected to a second tube that extends from the intercostal pump to a second area of a patient's body, for example, the patient's peritoneal cavity. In use, the intercostal pump is placed between a first rib and a second rib in a patient. The intercostal pump operates by being successively compressed and decompressed between the first and second ribs as the patient breathes.

16 Claims, 44 Drawing Sheets

(56) References Cited

U.S. PATENT DOCUMENTS

| | | | |
|---|---|---|---|
| 5,154,693 A * | 10/1992 | East | A61M 27/006 |
| | | | 604/9 |
| 5,261,459 A * | 11/1993 | Atkinson | A61M 39/24 |
| | | | 137/846 |
| 5,830,172 A | 11/1998 | Leveen et al. | |
| 8,157,760 B2 | 4/2012 | Criado et al. | |
| 9,393,387 B1 * | 7/2016 | Mayse | A61M 27/002 |
| 9,421,348 B2 | 8/2016 | Lenihan et al. | |
| 9,662,478 B2 | 5/2017 | Browd et al. | |
| 10,252,037 B2 | 4/2019 | Degen et al. | |
| 10,300,255 B1 | 5/2019 | Mayse et al. | |
| 10,569,003 B2 | 2/2020 | Degen et al. | |
| 2011/0196194 A1 * | 8/2011 | Forsell | A61M 1/82 |
| | | | 600/31 |
| 2013/0197422 A1 * | 8/2013 | Browd | A61B 5/031 |
| | | | 604/9 |
| 2019/0105476 A1 | 4/2019 | Turtz | |

OTHER PUBLICATIONS

"International Application Serial No. PCT US2021 021643, Written Opinion dated Jun. 22, 2021", 9 pgs.

Astoul, Philippe, et al., "Novel pleural-bladder pump in malignant pleural effusions: from animal model to man", Astoul P, et al. Thorax 2020;75, (2020), pp. 432-434.

* cited by examiner

A

B

C

D

AUTOMATIC PLEURAL-PERITONAL PUMP

RELATED APPLICATIONS

This application relates to U.S. patent application. Ser. No. 13/968,479, filed on Aug. 16, 2013, entitled "Systems and Methods for Draining Bodily Fluid via an Intercostal Pump," which is hereby incorporated by reference herein in its entirety.

BACKGROUND

A number of techniques for draining bodily fluid involve utilizing a pump, in combination with a shunt or catheter, to drain fluid from one cavity within the human body to either another cavity or to a reservoir outside of the body. Such techniques may be utilized for purposes including, for example, draining a patient's blood, urine, saliva, cerebrospinal fluid, peritoneal fluid, and/or pleural fluid, among other possibilities.

One drainage-technique application is the drainage of pleural fluid for the treatment of pleural effusions. Pleural fluid is normally a low-protein liquid that can be found in relatively small amounts (normally 10-20 milliliters) in each of a patient's pleural cavities. The pleural cavities are the spaces between the visceral pleura (i.e., the membrane located over the entire outer surface of each lung) and the parietal pleura (i.e., the membrane lining the inside of the chest wall of each hemithorax). The small amount of pleural fluid in each pleural space is spread out very thinly between the visceral and parietal pleura thereby providing for a large surface tension which mechanically couples the lung to the chest wall while simultaneously lubricating these surfaces allowing the lung to slide over the chest wall during the breathing process. In a normal, healthy person, pleural fluid is constantly being produced, largely from leakage of fluid from blood and lymphatic vessels in the visceral pleura that coats the outer surface of the lung and reabsorbed at essentially the same rate by lymphatic channels located in the parietal pleural that lines the chest wall. This dynamic balance exchanges the fluid multiple times a day and maintains a low total volume in the 10-20 milliliter range. However, under certain abnormal conditions, such as infection, inflammation, malignancy, heart failure, liver failure, or kidney failure, among other conditions, the net flow of pleural fluid within the pleural cavity becomes unbalanced, with increased fluid production, decreased reabsorption, or both, resulting in the excess accumulation (e.g., on the order several hundred milliliters to several liters) of fluid in the pleural space.

Excess accumulation of pleural fluid is known as pleural effusion and adds additional mass that must be moved with each breath and may cause the pathological compression of lung tissue. This results in considerable difficulty in or prevention of the breathing process. Pleural effusion may lead to, for example, dyspnea, shortness of breath, chest pain, and/or chronic cough, and may greatly compromise a patient's quality of life.

Currently, pleural effusions affect approximately 1.5 million new patients each year in the United States. Many of these effusions are chronic, recur if drained, and can be quite symptomatic and debilitating for the patient. One common type of recurrent, symptomatic pleural effusion is the result of malignancy. Over 200,000 malignant pleural effusions occur each year in the United States and more than one half of those patients with malignant pleural effusions have recurrent symptoms resulting directly from their effusion.

Treatment options for recurrent, symptomatic pleural effusions can be divided into 1) repeated drainage of the pleural effusion and 2) elimination of the pleural space.

One approach to the treatment of recurrent, symptomatic pleural effusions, is repeated therapeutic thoracentesis. Thoracentesis involves passing a needle and catheter apparatus into the pleural cavity, at which point the needle is removed, leaving the catheter in the pleural space. The catheter remains in place and, thereby, acts as a drainage tube that allows the excess pleural fluid to be moved from the pleural space to a collection reservoir outside of the body. This procedure typically improves symptoms significantly. Unfortunately, malignant effusions are likely to recur following drainage and in order to control symptoms therapeutic thoracentesis must be repeated frequently. However, due to patients' delays in notifying their physician that their symptoms have returned and delays in organizing and providing repeat thoracentesis, patients often spend a significant portion of their life with effusion-related symptoms. Furthermore, thoracentesis is painful and uncomfortable, and is frequently accompanied by complications such as pneumothorax (i.e., the collapse of the lung due to accumulation of air in the pleural cavity) in up to eleven percent of patients and severe bleeding or infection in many others.

Another treatment option is pleurodesis. Pleurodesis is the obliteration of the pleural space and adhesion of the visceral and parietal pleural surfaces by the instillation of a sclerosant agent into the pleural space. In one approach, the sclerosant agent is introduced via a chest tube that has been inserted into the patient under moderate sedation or general anesthesia for drainage of the pleural fluid in a manner similar to the drainage achieved in thoracentesis. After drainage of the pleural effusion a sclerosing agent is instilled through the tube into the pleural cavity to completely coat the visceral and parietal membranes so that these membranes will permanently adhere to each other to close and eliminate the pleural cavity. Chest-tube pleurodesis can sometimes lead to long-term control of effusion-related symptoms. Unfortunately, chest-tube pleurodesis typically requires hospitalization for at least two days and as many as seven days, can be quite painful, can lead to breathing difficulties related to the pleurodesis, and, in up to one third of patients, fails to provide relief of symptoms for more than a few weeks.

Another variation of pleurodesis is thoracoscopic pleurodesis, which involves the insertion of a telescope into the patient's chest by way of an intercostal incision on the patient's side. Pleural fluid is evacuated, and a detailed inspection of the pleural space is undertaken so as to more discriminately apply sclerosant to regions of abnormality. In some cases, thoracoscopic pleurodesis can achieve better results than chest-tube pleurodesis. Unfortunately, thoracoscopic pleurodesis typically still requires prolonged hospitalization for four to seven days, can also be quite painful, can lead to breathing difficulties related to the pleurodesis, and, in many patients, fails to provide relief of symptoms for more than a few weeks.

Yet another treatment option is chronic indwelling pleural catheters. Such indwelling catheters are placed in the patient permanently, allowing a patient to drain pleural fluid to an external reservoir on an intermittent, yet continual, basis. That is, the pleural catheter is placed with one end in the affected pleural space inside the patient's body and the other end of the catheter extends outside of the patient's body and remains externally exposed for extended period of times. Chronic indwelling catheters have been shown to result in relatively high success rates in the management of effusion-related symptoms and are associated with relatively short patient-hospital times of approximately one day. However, because the catheter passes through the patient's skin with a portion inside the body and a portion outside the body, a considerable fraction of patients, approximately eight percent, fall victim to infection. Further, the patient is subject to the discomfort, irritation, and annoyance of an exposed indwelling catheter. Finally, in order to gain relief from effusion related symptoms, the patient or their caregiver must actively access the external portion of the catheter, connect the catheter to an external reservoir, and drain effusion fluid from the pleural space into the reservoir.

Still another approach are pleuroperitoneal shunts. Pleuroperitoneal shunts provide a permanent conduit between the pleural cavity and the peritoneal cavity, or the abdomen, which allows fluid to move from the pleural cavity to the peritoneal cavity, as opposed to an external reservoir. Once in the peritoneal cavity, the fluid is reabsorbed into the patient's blood stream through blood and lymph vessels located in the abdomen. In popular pleuroperitoneal shunts, the shunt has a pumping chamber that must be manually activated by the patient or caregiver to move the pleural fluid. The pleuroperitoneal shunt is tunneled under the skin from the chest to the abdomen with the pumping chamber lodged in a subcutaneous pocket overlying the rib cage. Pleuroperitoneal shunts, like chronic indwelling catheters, have been shown to result in relatively high success rates in the management of effusion-related symptoms and are associated with relatively short patient-hospital times of approximately one day. However, also like chronic indwelling catheters, a considerable percentage of patients, approximately four percent, fall victim to infection. Further drawbacks of conventional pleuroperitoneal shunts include a relatively high rate of shunt-specific complications, such as clotting of fluid within the shunt. Finally, in order to gain relief from effusion related symptoms, the patient or their caregiver must actively compress the pumping chamber multiple repeatedly to transfer effusion fluid from the pleural space to the peritoneal space causing significant discomfort and inconvenience.

Other drainage-technique applications exist. These include, but are not limited to, drainage of pericardial fluid, cerebrospinal fluid, peritoneal fluid, urine, bile, and lymph. Cavities into which such fluids can be drained include, but are not limited to, the pleural space, the peritoneal space, the bile duct, the stomach, lymphatic vessels including the thoracic duct, veins including the vena cava, and the bladder.

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

BRIEF SUMMARY

There is a need for a novel technique of draining pleural fluid that provides for a high rate of success in treating pleural effusions, avoids high rates of infection and other complications, doesn't require lengthy patient-hospital times and/or repeated hospital visits, and avoids the inconvenient necessity of manually compressing the pumping chamber multiple times each and every day or the inconvenient necessity of physically connecting the catheter to an external reservoir in order to relieve symptoms. A fluid management system based on an automatic pump, as described herein, provides for such a novel and beneficial drainage technique.

An automatic pump-based fluid management system, as described herein, comprises a pump that is, generally, a pumping chamber having a first one-way valve located at an inlet to the pumping chamber and a second one-way valve located in series with the first valve at an outlet from the pumping chamber. The volume of the pumping chamber in contact with the fluid is capable of being increased or decreased. The inlet is attached to a first tube that extends from the automatic pump to a first area of a patient's body, for example, the patient's pleural cavity. The outlet is connected to a second tube that extends from the automatic pump to a second area of a patient's body. The second area of the patient's body may be, for example, the patient's peritoneal cavity. Upon operation of the automatic pump, fluid is transferred from the first area of the patient's body to the second area.

In one embodiment, the pumping chamber of the automatic pump is a resilient flexible tube and the pumping chamber is placed between a first rib and a second rib in a patient. (Note that although the terms "first rib" and "second rib" are used herein, it should be understood that such use does not necessarily refer to any particular two ribs, e.g. the "first" and "second" ribs as typically referred to in anatomical contexts as the two ribs nearest a patients' skull.) The automatic pump operates by the pumping chamber being successively compressed and decompressed between the first and second ribs as the patient breaths thereby cyclically changing the volume of the pumping chamber. As the patient inhales, the patient's rib cage expands, the intercostal space (or the space between the first and second ribs) is increased, and the pumping chamber is decompressed. As the patient exhales, the patient's rib cage contracts, the intercostal space narrows, and the pumping chamber is compressed. For a person breathing 12 times a minute this means that the pumping chamber is compressed and decompressed 17,280 times a day.

In another embodiment, the pumping chamber of the automatic pump is an elongate resilient flexible tube with a portion of the pumping chamber placed between a first rib and a second rib in a patient and a second portion of the elongate pumping chamber positioned in the sub-cutaneous tissues of the patient between the rib cage and the skin. The automatic pump thereby can operate in two ways, first by the pumping chamber being successively compressed and decompressed between the first and second ribs as the patient breathes thereby cyclically changing the volume of the pumping chamber, and second by the patient or a caregiver manually compressing the portion of the elongate pumping chamber located between the patient's rib cage and their skin. Hence, as the patient inhales the portion of the pumping chamber located between a first and second rib is decompressed and as the patient exhales the portion pumping chamber is compressed thereby providing for automatic pumping. Additionally, if there is excess effusion fluid in the pleural space, as determined based on patient symptoms, radiography or ultrasonography, the patient or patient caregiver can, perhaps repeatedly, manually compress the portion of the pumping chamber between their digits or hand and the rib cage to provide additional pumping action.

In yet another embodiment, the pumping chamber of the automatic pump has a first portion composed of resilient flexible tube placed between a first rib and a second rib in a patient and a second portion composed of a semi-rigid chamber with an electro-mechanical pump that can aide in the pumping action provided by the first portion. The automatic pump thereby can operate first by the first portion of the pumping chamber being successively compressed and decompressed between the first and second ribs as the patient breaths thereby cyclically changing the volume of the pumping chamber as well as by cyclical changes of the volume of the pumping chamber produced by the electro-mechanical pump of the second portion. Hence, as the patient inhales, the first portion of the pumping chamber located between a first and second rib is decompressed filling with effusion fluid from the pleural space, and as the patient exhales, the first portion of the pumping chamber is compressed pushing fluid out of the pumping chamber into the peritoneal space. The electro-mechanical pump of the second portion can also pump fluid from the pleural space to the peritoneal space independent of the action of the pumping chamber positioned between the first and second rib.

Use of an automatic pump as described herein avoids certain shortcomings of known fluid drainage techniques. For instance, the intercostal pump operates to drain fluid regularly, continuously, and automatically without requiring a patient to manually compress a pump by hand or requiring a patient to drain fluid external to the patient's body. Further, due to the continuous operation of the intercostal pump, improved performance may be achieved by decreasing the occurrence of clotting observed in other fluid-drainage systems that may remain inactive for long periods of time.

The foregoing presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments. Other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the scope of the present disclosure. Accordingly, the drawings and detailed description are to be regarded as illustrative in nature and not restrictive.

BRIEF DESCRIPTION OF DRAWINGS

The invention disclosed herein will be more readily understood from a reading of the specification with reference to the accompanying drawings forming a part thereof, wherein.

DETAILED DESCRIPTION

The apparatuses, systems, and methods described herein may be used for the purposes of draining and/or moving fluid from one cavity within the human body to another cavity. Particularly, the apparatuses, systems, and methods described herein comprise an automatic pump which provides a general pumping function in an automatic pump-based fluid management system.

For purposes of explanation, the disclosure herein includes a discussion of the use of an automatic pump-based fluid management system for the purposes of drainage of pleural fluid for the treatment of pleural effusions. However, it should be understood that such an application is but one particular application of one particular embodiment of an automatic pump-based fluid management system, and that other embodiments and applications are possible.

Also, for purposes of explanation, the disclosure herein describes an automatic pump as part of a particular automatic pump-based fluid management systems. However, it should be understood that any such automatic pump-based fluid management system disclosed herein is but a particular embodiment of an automatic pump-based fluid management system that uses an automatic pump as described herein, and that other uses of an automatic pump are possible.

The automatic pump-based fluid management system can provide regular, continuous, and automatic drainage of bodily fluid. Therefore, many of the disadvantages of other techniques for draining bodily fluid may be avoided.

1. Automatic Pump-Based Fluid Management System

Figure 1:
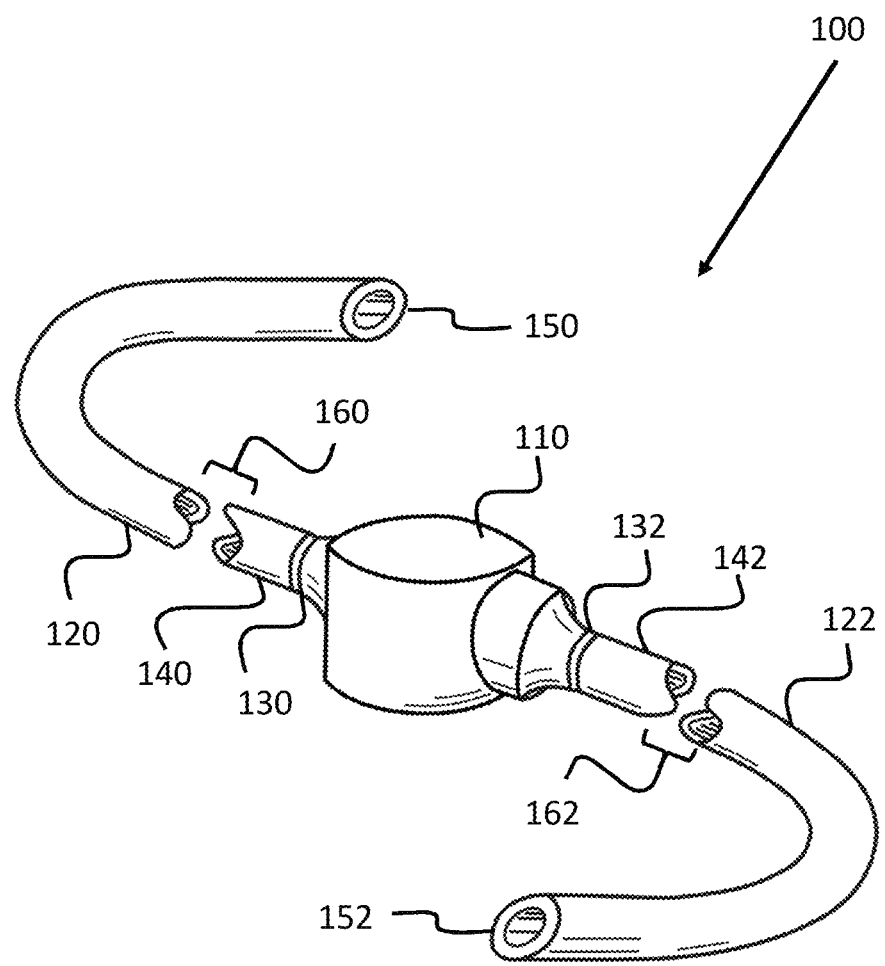
FIG. 1 shows a perspective view of an automatic pump-based fluid management system including a pump and also including inlet and outlet tubes (inlet and outlet tubes represented schematically shortened for illustrative purposes)

FIG. 1 shows a perspective view of an automatic pump-based fluid management system including an automatic pump and including inlet and outlet tubes (the depiction of which have been schematically represented shortened in length for illustrative purposes). It should be understood that FIG. 1 shows an embodiment of an automatic pump-based fluid management system for purposes of explanation and that other embodiments are possible.

a. Automatic Pump-Based Fluid Management System General

With reference to FIG. 1, automatic pump-based fluid management system 100 for the movement of fluid from a first body compartment to a second body compartment comprises a pump 110 that generally has an inlet 130 and an outlet 132 and is capable of moving fluid between the inlet 130 and outlet 132.

Automatic pump-based fluid management system 100 also comprises a first tube 120 and a second tube 122. Inlet 130 and outlet 132 each communicate between the interior and the exterior of pump 110 and are coupled to the first tube 120 and the second tube 122, respectively. In other words, inlet 130 and outlet 132 are configured so as to provide for fluid communication between first tube 120 and second tube 122, respectively, and an interior space of pump 110.

Further, first tube 120 comprises a tube-inlet end 150 and a pump-inlet end 140. Generally, first tube 120 is configured so that when automatic pump-based fluid management system 100 is in use, tube-inlet end 150 may be disposed in an area of a person's body from which fluid is to be drained. On the other hand, pump-inlet end 140 is coupled to inlet 130 of pump 110. Accordingly, the length of first tube 120 may vary, as depicted by length extension 160.

Similarly, second tube 122 comprises a pump-outlet end 142 and a tube-outlet end 152. Generally, second tube 122 is configured so that when automatic pump-based fluid management system 100 is in use, tube-outlet end 152 may be disposed in an area of a person's body to which fluid is to be drained. On the other hand, pump-outlet end 142 is coupled to outlet 132 of the pump 110. Accordingly, the length of second tube 122 may vary, as depicted by length extension 162.

Although first tube 120 and second tube 122 are shown as entering into pump 110 in a substantially straight manner (i.e., perpendicular to a wall of the pump 110), first tube 120 and second tube 122 may be configured to enter pump 110 at any desired angle. For example, it may be desirable for first tube 120 and second tube 122 to enter and leave, respectively, pump 110 at about 90 degree angles so as to enable pump 110 to be situated in a more advantageous manner. It may be desirable for first tube 120 and second tube 122 to enter and leave at other angles as well.

Although tubes 120 and 122 are generally shown as flexible tubing that may be easily manipulated and/or shaped to take any form or direction, in some embodiments it may be desirable for tubes 120 and 122 to be rigidly or semi-rigidly defined, to some extent, so that a desired shape or direction of the tubes may be maintained. For example, one of the tubes may be at least partially rigidly or semi-rigidly configured, shaped, or cast so that it has a 90-degree bend upon leaving intercostal pump 110. Each of tubes 120 and 122 may be configured to a similar 90-degree bend. Alternatively, the tubes may not have similar bends. As yet another alternative, the tubes may each have a bend of some other degree.

To achieve automatic pump-based fluid movement, the pump 110 may be an automatic intercostal pump, discussed in greater detail below, composed of a substantially resilient, flexible chamber with a one-way valve at the inlet and a one-way at the outlet that takes advantage of rib motion during normal breathing to automatically and cyclically compress and decompress the resilient, flexible chamber between adjacent ribs and thereby provide a pumping action. Alternatively, pump 110 may be an electro-mechanical pump, discussed in greater detail below, such as a gear pump, screw pump, rotary vane pump, diaphragm pump, piezoelectric diaphragm pump, plunger pump, peristaltic pump, lobe pump, piston pump, or centrifugal pump. Other types of pumps are possible as well.

b. Pleuroperitoneal Automatic Pump-Based Fluid Management System

Figure 2A:
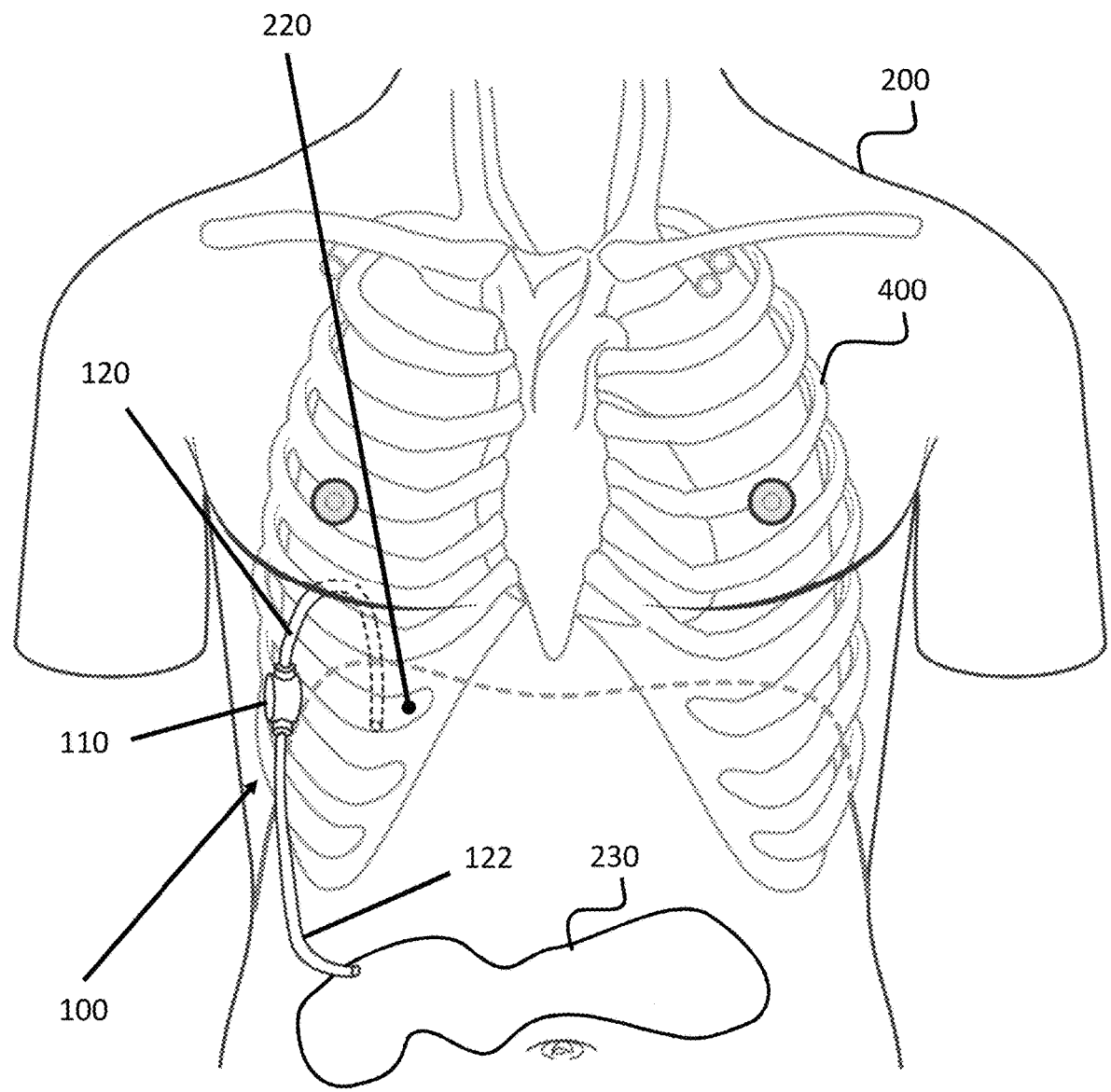
FIGS. 2A, 2B, and 2C show an automatic pump-based fluid management system implanted in a patient.

With reference to FIG. 2A, automatic pump-based fluid management system 100 is shown implanted in a patient 200, providing for drainage of fluid from a first area 220 to a second area 230 within the patient's body. In one embodiment, as in the embodiment depicted in FIG. 2A, fluid is drained from a patient's pleural cavity to the patient's peritoneal cavity. In such an embodiment, therefore, first area 220 is the patient's pleural cavity and second area 230 is the patient's peritoneal cavity.

In an embodiment, automatic pump 110 is configured so that it may be placed on the exterior of the patient's rib cage 400 under the patient's skin. To access the patient's pleural cavity 220, the first tube 120 passes from the pump inlet 130 and traverses the rib cage 400 between adjacent ribs with the tube-inlet end 150 of the first tube 120 disposed in a person's pleural cavity 220 from which fluid is to be drained. The second tube 122 passes from the pump outlet 132 and traverses under the skin along the abdominal wall with the tube-outlet end 152 of the second tube 122 disposed in a person's peritoneal cavity 230 into which fluid is to be drained. The peritoneal cavity 230 has a fluid absorptive capacity such that excess fluid transferred from the pleural cavity 220 will be resorbed into, for example, the patient's interstitial tissues, lymphatics, and blood vessels thereby minimizing accumulation of fluid in the peritoneal cavity 230.

Figure 2B:
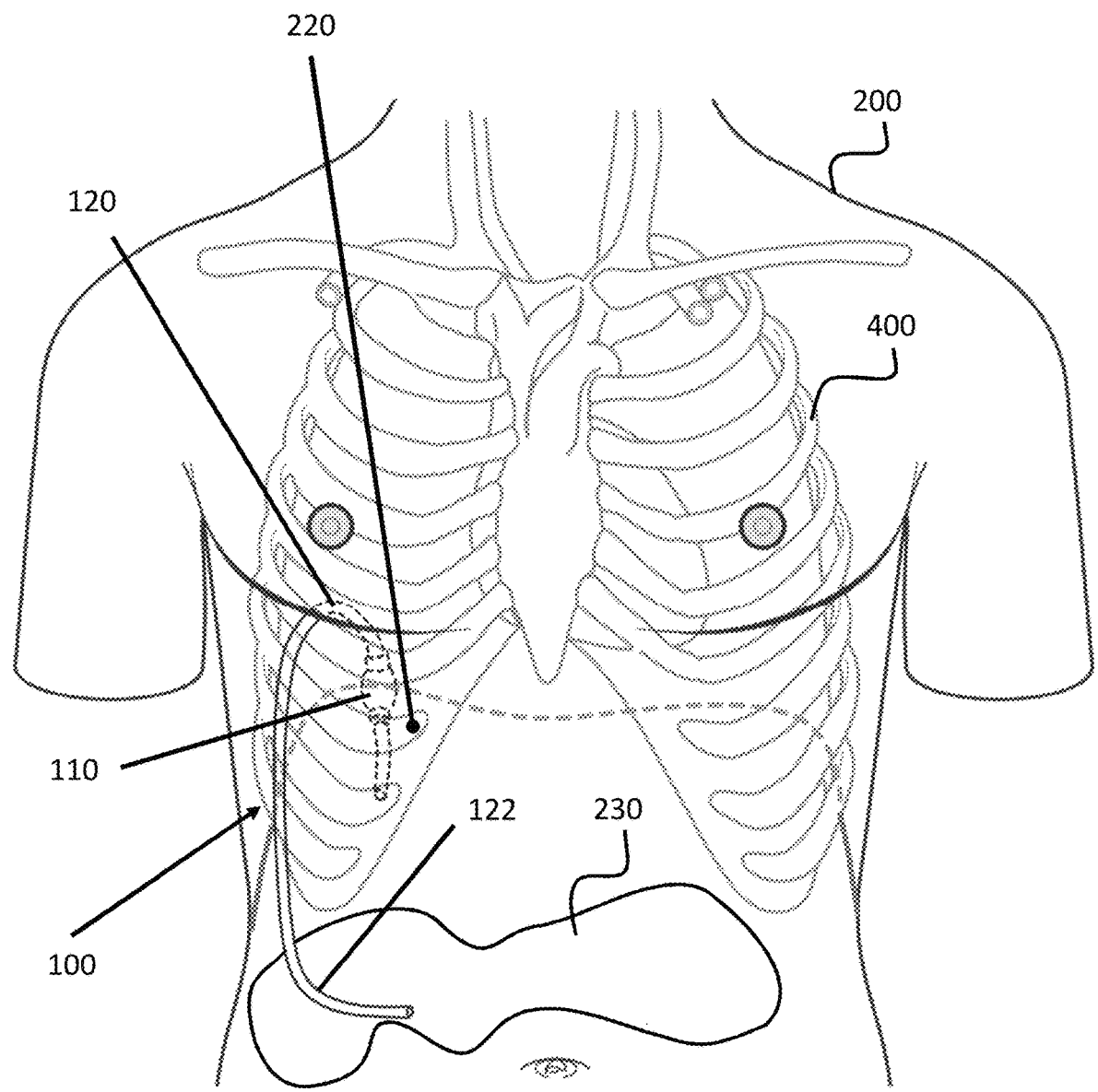

In other embodiments, as shown in FIG. 2B, the automatic pump 110 can be configured so that it may be placed within the patient's pleural cavity 220. The tube-inlet end 150 of the first tube 120 as well as the first tube 120 can be disposed in a person's pleural cavity 220 from which fluid is to be drained. The second tube 122 passes from the pump outlet 132 of the automatic pump 110 located in the pleural cavity 120 into the peritoneal cavity such that the tube-outlet end 152 of the second tube 122 is disposed in a person's peritoneal cavity 230 into which fluid is to be drained. The second tube 122 may traverse the rib cage 400 between adjacent ribs, travel along the rib cage 400 under the skin and traverses the abdominal wall such that the tube-outlet end 152 of the second tube 122 is disposed in a person's peritoneal cavity 230 into which fluid is to be drained. Alternatively, the pathway of the second tube 122 may pass directly from the patient's pleural cavity 220 through the diaphragm 240 into the patient's peritoneal cavity 230.

Figure 2C:
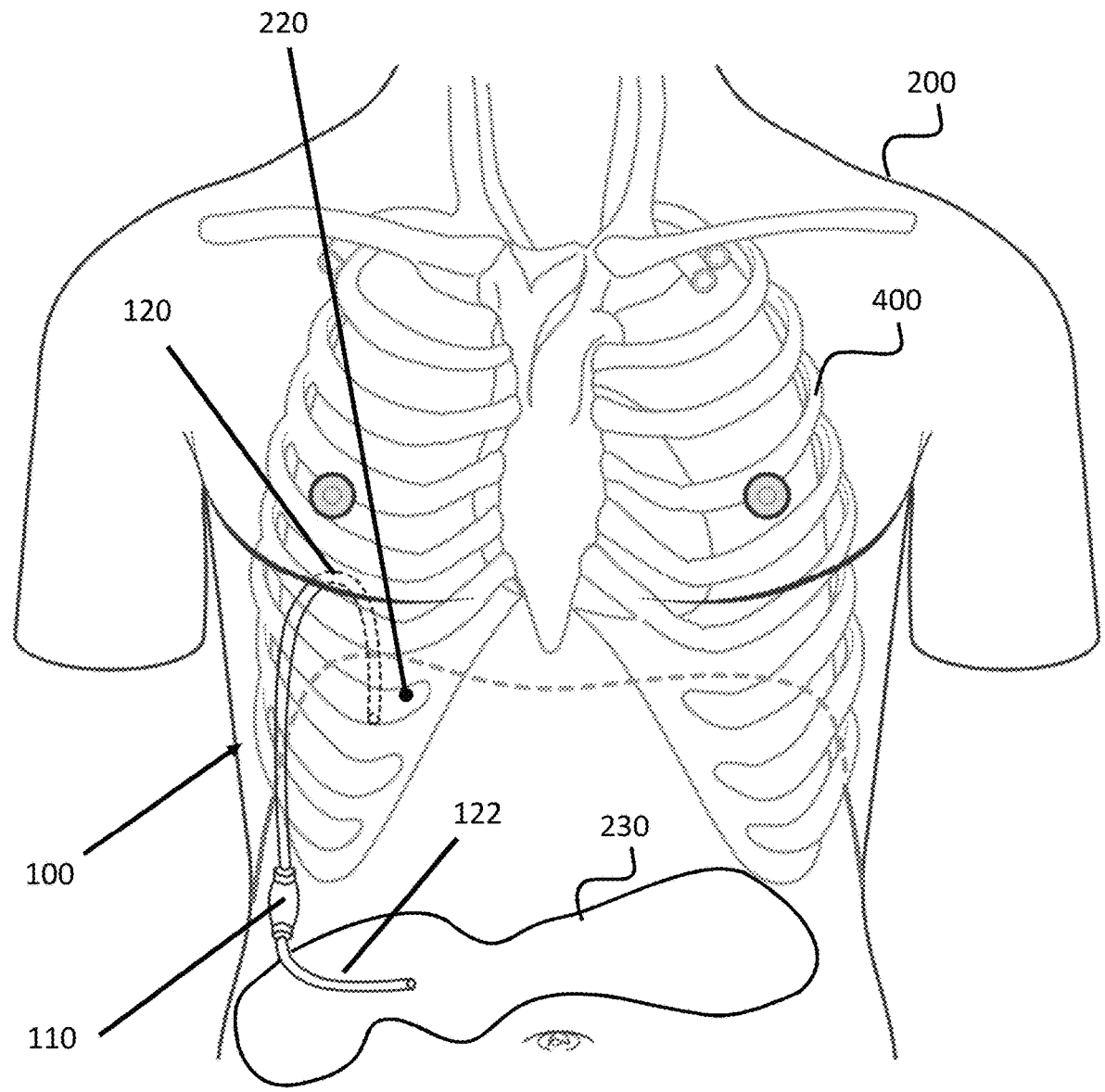

In other embodiments, as shown in FIG. 2C, the automatic pump 110 and outlet second tube 230 can be configured to be placed within the patient's peritoneal cavity 230 with the first tube passing from the pump inlet 130 through the abdominal wall, along the rib cage 400 under the skin, and traverse the rib cage 400 between adjacent ribs to enter the pleural cavity 220 such that the tube-inlet end 150 of the first tube 120 is located in the pleural cavity. Alternatively, the pathway of the first tube 120 may pass directly from the patient's pleural cavity 220 to the patient's peritoneal cavity 230 through the diaphragm 240.

c. Pleural Cavity and Peritoneal Cavity Pressures

Pressures in the pleural cavity 220 and peritoneal cavity 230 are not the same, are not static, and typically vary during normal breathing. Inspiration is an active process requiring muscle contraction. During inspiration, the external intercostal muscles contract leading to elevation of the ribs and sternum, and the diaphragm contracts, flattening out and pressing down on the abdominal contents. This combined action leads to an expansion of the thoracic cavity with a decrease in the pleural pressure ($P_{pleural}$) that expands the elastic lung and a simultaneous compression of the abdominal contents with an increase in the peritoneal pressure ($P_{peritoneal}$). Expiration during normal breathing is largely a passive process relying on elastic recoil. During expiration, the external intercostal muscles and the diaphragm simply relax. With relaxation of the external intercostals, the elasticity of the inflated lungs causes them to recoil back to their original position. Simultaneously, the diaphragm relaxes and the compressed abdominal contents push the diaphragm up. This combined action leads to a decrease in size of the thoracic cavity with an increase in the pleural pressure ($P_{pleural}$) and a simultaneous decrease in the peritoneal pressure ($P_{peritoneal}$).

Figure 3:
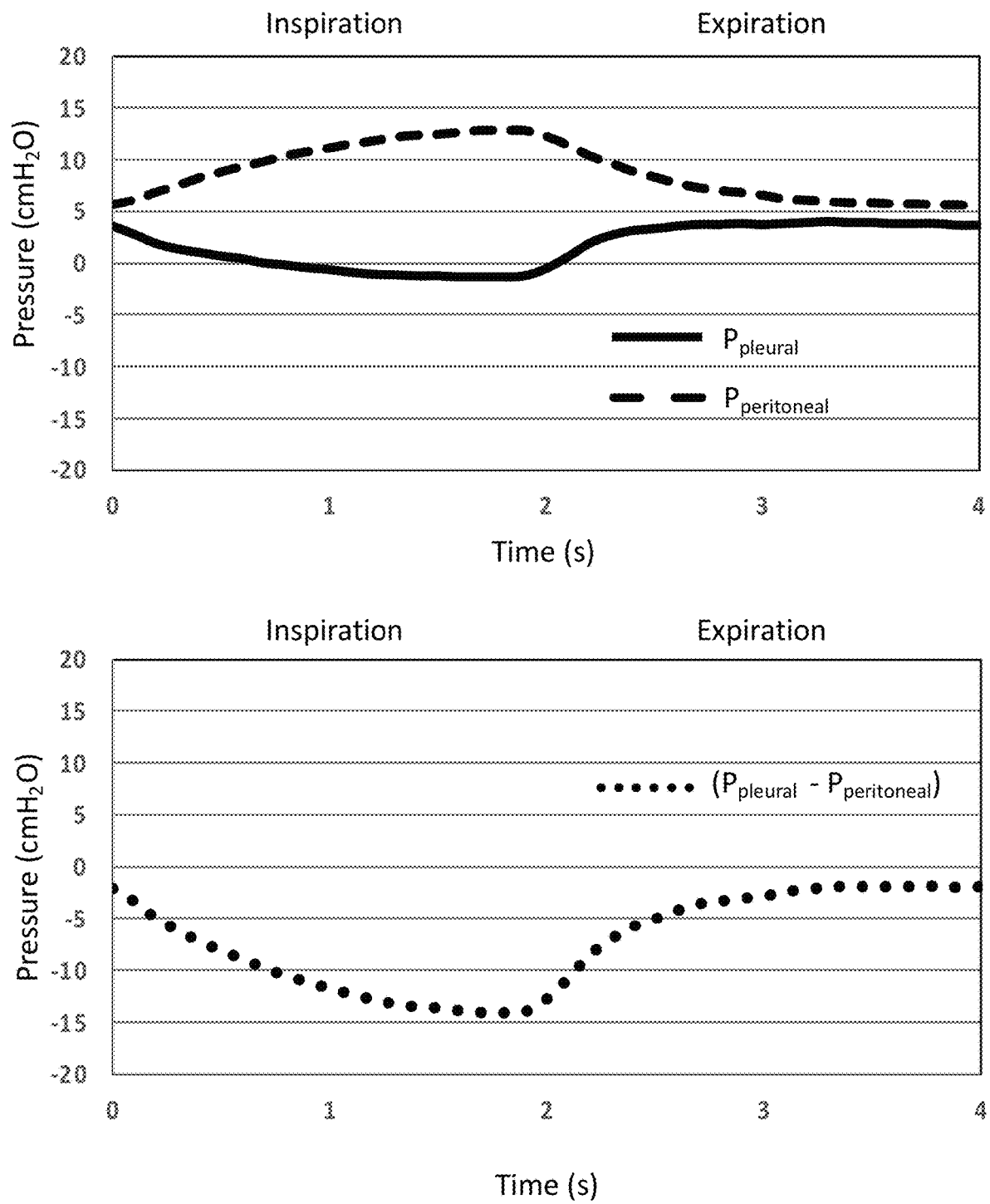
FIG. 3 shows representative pleural and peritoneal pressures as they change during inspiration and expiration.

As seen in FIG. 3, during normal, resting breathing in patients with little to no pleural effusion fluid, pleural pressure ($P_{pleural}$) varies from about +3 cmH$_2$O at the end of expiration to about −2 cmH$_2$O at end of inspiration and peritoneal pressure ($P_{peritoneal}$) varies from about +5 cmH$_2$O at the end of expiration to about +13 cmH$_2$O at end of inspiration. Overall pleural pressure is lower than peritoneal pressure during the entire respiratory cycle with a gradient that varies on average from about −2 cmH$_2$O at the end of expiration to about −15 cmH$_2$O at the end of inspiration. [Miller J D, Skeletal muscle pump versus respiratory muscle pump: modulation of venous return from the locomotor limb in humans. *J Physiol* 2005; 563(3): 925-943]. Pleural pressures, peritoneal pressures, as well as the pleural-to-peritoneal pressure gradient vary from patient-to-patient and are altered with exertion, coughing, sneezing, deep breathing, body position, diseases of the chest or abdomen, prior chest or abdominal surgery, and the presence of pleural effusion fluid. In fact, the presence of pleural effusion fluid can add a significant hydrostatic pressure component to pleural space pressures, changing the pleural pressures from values that are low or even negative to values that are positive. In fact, in patients with pleural effusions, pleural pressure ($P_{pleural}$) may increase to about +10 to about +15 cmH$_2$O when the effusion fluid is present and may decrease to about −10 to about −15 cmH$_2$O when the effusion fluid is drained. [Feller-Kopman D, Large-volume thoracentesis and the risk of re-expansion pulmonary edema. *Ann Thor Surg* 2007; 84: 1656-1662]. When the impact of pleural effusion fluid is added to the variation that occurs during normal breathing, pleural pressure may be higher than peritoneal pressure during respiratory cycle with gradients that can range from about −5 cmH$_2$O to about +13 cmH$_2$O while the effusion fluid is present.

For the automatic pump-based fluid management system 100 to transfer fluid from the pleural cavity 220 to the peritoneal cavity 230, the automatic pump 110 can overcome the pressure gradient that exists from the pleural cavity 220 to the peritoneal cavity 230. As outlined above, this pressure gradient varies during the respiratory cycle and for the case of pleural effusions, the amount of effusion fluid that is present. When the automatic pump-based fluid management system 100 is initially placed and effusion fluid is present in the pleural cavity 220, fluid can flow freely between the pleural cavity 220 to the peritoneal cavity 230 when the valves within the automatic pump 110 have a combined opening pressure that is below the pleural-to-peritoneal pressure gradient.

When the pleural effusion fluid is largely drained from the pleural cavity 220, a lower pleural-to-peritoneal pressure gradient exists as shown in FIG. 3. Because of this pressure gradient, at the end expiration the automatic pump 110 can generate at least about 2 cmH$_2$O of head pressure to overcome this pressure gradient and pump fluid from the pleural cavity 220 to the peritoneal cavity 230. Similarly, at end inspiration the automatic pump 110 can generate at least about 15 cmH$_2$O of head pressure to overcome the pressure gradient between the peritoneal cavity 230 and the pleural cavity 220 and therefore be able to pump fluid from the pleural cavity 220 to the peritoneal cavity 230. It is noted that if the pump generates a constant head pressure, the flow between the pleural cavity 220 and peritoneal cavity 230 will vary during the breathing cycle because the pressure gradient between the peritoneal cavity 230 and the pleural cavity 220 varies. The values presented above are based on average observations. In some situations, the pump may generate at least about 25 cmH$_2$O of head pressure to overcome variation in the pressure gradient that might exist during a full cycle of normal breathing and therefore be able to pump fluid from the pleural cavity 220 and peritoneal cavity 230 at any point during normal breathing, and even as high as about 35 cmH$_2$O to about 50 cmH$_2$O to overcome patient-to-patient variation. Additionally, it can be noted that an automatic pump 110 can be designed to operate preferentially during expiration, and ideally during the end portion of expiration when pressure gradient between the peritoneal cavity 230 and the pleural cavity 220 is lower. In this situation, the automatic pump 110 may need to only generate a minimum head pressure of about 5 cmH$_2$O, or preferably about 10 cmH$_2$O to about 15 cmH$_2$O, in order to overcome patient-to-patient variation, to pump fluid from the pleural cavity 220 to the peritoneal cavity 230. This lower head pressure translates to a lower rate of power consumption and lower total work per unit volume of pumped effusion fluid for the automatic pump 110 when compared to operation of the automatic pump 110 during the entire respiratory cycle, the beginning portion of expiration, or the end portion of inspiration.

d. Pleural Fluid Debris and Coagulant Proteins

Pleural fluid, in both health and disease, is essentially a filtrate of blood that is modified by reabsorption. Filtration occurs though blood vessel walls, interstitial tissues, and mesothelial cell membranes of both the visceral and parietal pleural surfaces, and modification occurs by fluid, solute, protein, and cellular reabsorption. Similar to interstitial liquid of other organs, in healthy individuals, pleural fluid contains protein and a few cells. Pleural fluid protein has a total concentration of approximately 1.0 g/dl (plasma total protein concentration of 6.0 g/dl or greater) with the albumin being the most abundant comprising approximately 50% of the total protein, globulin being the second most abundant comprising approximately 35% of the total protein, and fibrinogen being the third most abundant comprising less than 20% of the protein. The cell concentration is approximately 2,000 cells/mm$^3$ volume of pleural liquid and consist mainly of mesothelial cells, monocytes, and lymphocytes.

In malignancy, this system of filtration and reabsorption is unbalanced. The cells, membranes, and tissues that serve to filter blood tend to be less selective and resorptive mechanisms are altered and typically less effective. As such, the pleural fluid that is produced in malignancy is increased in volume and abnormal in composition such that fluid that is rich in both protein and cells, and the types of proteins and cells that are present are different. Indeed, pleural fluid total protein concentration is typically greater than 2.9 g/dl and cellular concentrations may increase many fold.

Fibrinogen is an important protein in pleural fluid. Fibrinogen is converted into fibrin by thrombin in a process called fibrinogenesis. Fibrin is broken down by the action of plasminogen in a process called fibrinolysis. In turn, plasminogen is activated by tissue plasminogen activator (tPA)

and tPA is inhibited by plasminogen activator inhibitor-1 (PAI-1). The net amount of fibrin that is produced is the result of an imbalance between fibrinogenesis and fibrinolysis.

Pleural fluid fibrinogen concentrations are typically low relative to plasma concentrations. Even in patients with malignancy, when total protein concentrations tend to be elevated, pleural fluid fibrinogen concentrations tend to be even lower, pleural fluid levels of tPA tend to be elevated, and PAI-1 tend to be decreased. All of these tend to make the net production of fibrin low.

Never-the-less, it is still possible in patients with malignant pleural effusion that an imbalance between fibrinogenesis and fibrinolysis may develop and may result in the formation of fibrin. Fibrin is capable of organizing into small clots, strands, membranes, and septa. Fibrin membranes and septa are responsible for pleural fluid loculations or pockets that can make drainage of fluid from the pleural space difficult, and fibrin clots and strands can block drainage tubes.

In fact, gross anatomic findings in malignant pleural effusions as demonstrated by transthoracic ultrasound of the pleural cavity reveal complex septated effusions in 8.7% of patients, homogeneously echogenic effusions in 15.4% and complex non-septated effusions in 65.4% of patients, both of which likely represent some combination of blood and cellular and fibrinous debris, and anechoic (clear fluid) in only 10.6% of patients.

Figure 4:
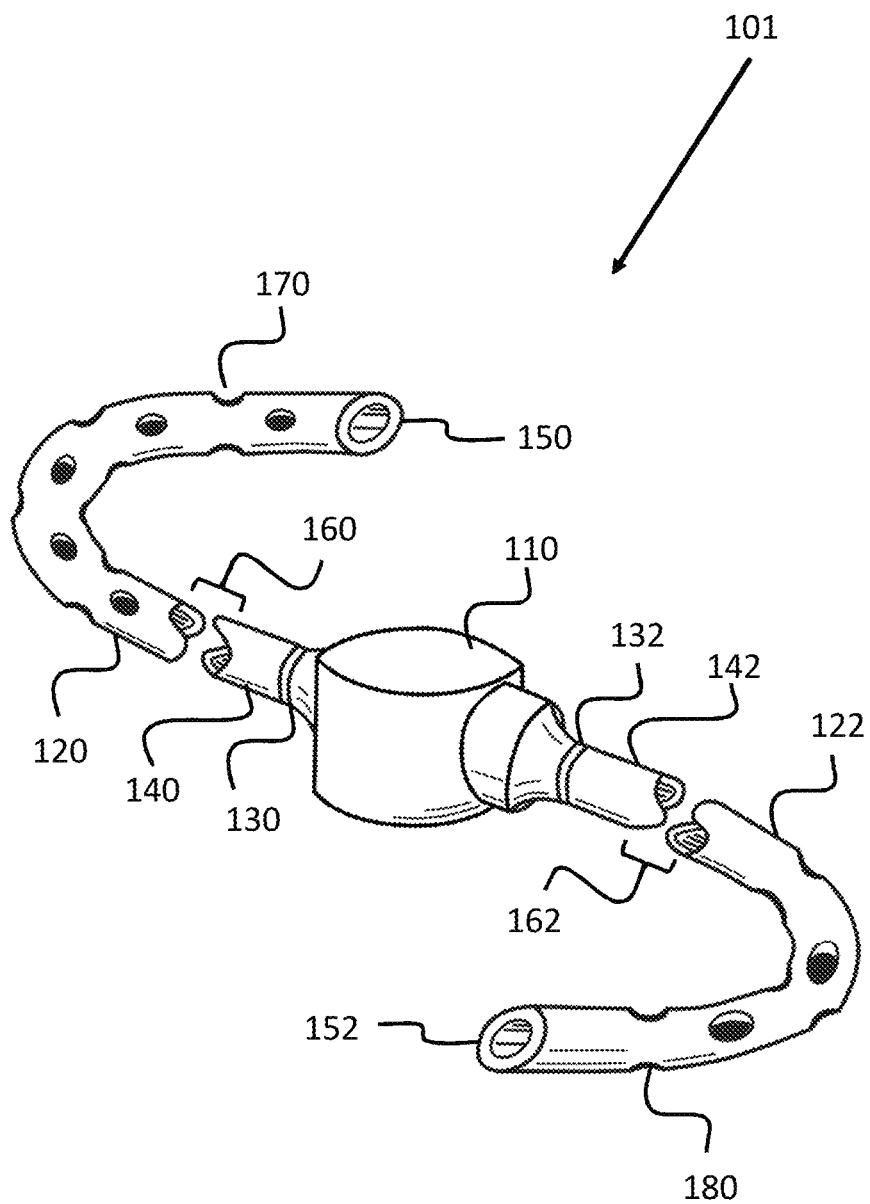
FIG. 4 shows a perspective view of an automatic pump-based fluid management system including a pump and also including inlet and outlet tubes that have perforations or fenestrations designed to prevent occlusion and to improve fluid flow (inlet and outlet tubes represented schematically shortened for illustrative purposes)

In order to prevent blocking or clogging of the automatic pump-based fluid management system and maintain flow through the system, multiple strategies may be employed either singly or in combination. One strategy is to provide multiple fluid-inlet pathways. With reference to FIG. 4, first tube 120 may comprise one or more fluid-inlet perforations 170. Fluid-inlet perforations 170 may take the form of holes in the wall of first tube 120 allowing for the intake of fluid into first tube 120 through not only tube-inlet end 150, but through fluid-inlet perforations 170 as well. Fluid-inlet perforations 170 may avoid obstruction of flow into the first tube 120 or may improve the volume or efficiency of fluid intake into first tube 120, and thereby, may improve the volume or efficiency of fluid drained by automatic pump-based fluid management system 101. Fluid-inlet perforations 170 may also be advantageous by allowing for alternative fluid inlet locations in the event that tube-inlet end 150, or other perforations 170, become blocked due to, for example, fibrin clots, fibrin strands, or other debris, or apposition of the first tube 120 against the chest wall or lung. Second tube 122 may also include fluid-outlet perforations 180.

Figure 5:
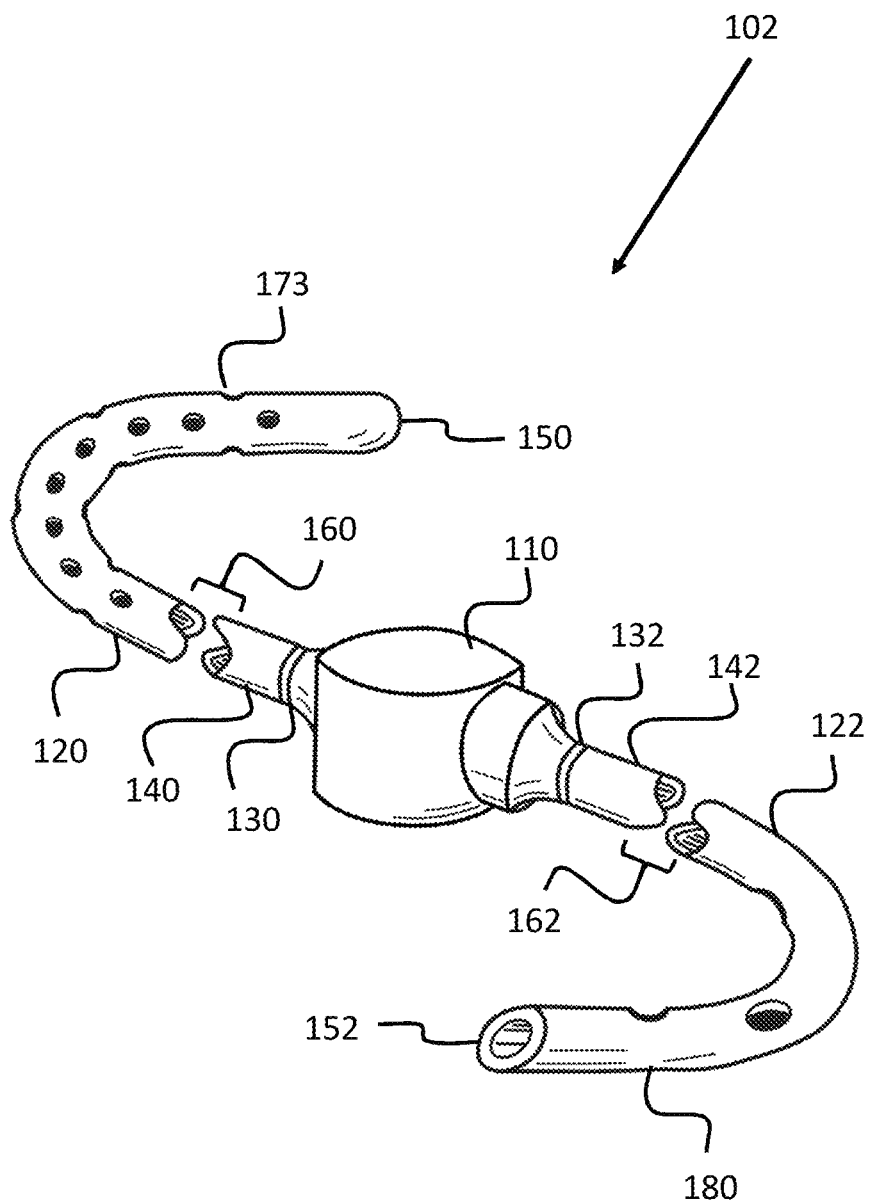
FIG. 5 shows a perspective view of an automatic pump-based fluid management system including a pump and also including an inlet tube with a rounded and closed end and small fenestrations designed to prevent entry of fibrin strands and particulates into the catheter and pump and thereby prevent occlusion of the system, as well as an outlet tube (inlet and outlet tubes represented schematically shortened for illustrative purposes)

An additional or alternative strategy is to construct the first tube 120 to provide a filtering mechanism for fluid entering the automatic pump-based fluid management system. With reference to FIG. 5, first tube 120 may comprise one or more filtering fluid-inlet perforations 173. Filtering fluid-inlet perforations 173 may take the form of holes in the wall of first tube 120 allowing for the intake of fluid into first tube 120. Filtering fluid-inlet perforations 173 are sized and shaped such that any fibrinous clots, fibrinous strands, or other debris that are able to pass through the filtering perforations 173 can pass through the entire fluid pathway of the filtered automatic pump-based fluid management system 102 without occluding or significantly obstructing fluid flow. Alternatively, filtering fluid-inlet perforations 173 are sized and shaped such that each and every such perforation is smaller than the smallest opening that exists along the entire fluid pathway of the filtered automatic pump-based fluid management system 102. As such, any fibrinous clots, fibrinous strands, or other debris that can pass through the filtering fluid-inlet perforations 173 will be smaller than the smallest openings in the fluid pathway of the filtered automatic pump-based fluid management system 102, and as such should be able to pass through the fluid pathway of the filtered automatic pump-based fluid management system 102. As illustrated in FIG. 5, tube-inlet end 150 of the first tube 120 may comprise a closed-end, and in some cases may be rounded or smoothed to assist in placement of the first tube 120.

Figure 6:
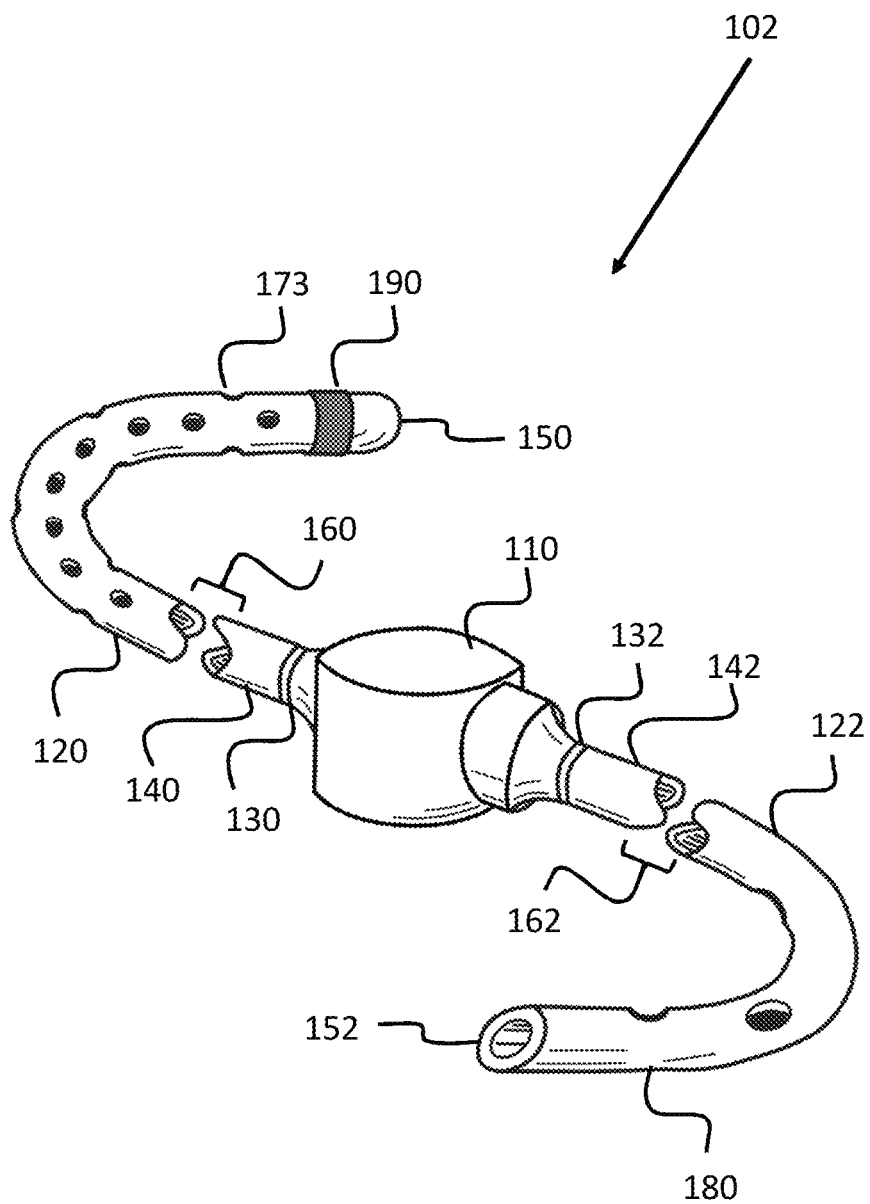
FIG. 6 shows a perspective view of an automatic pump-based fluid management system including a pump, perforated or fenestrated inlet and outlet tubes (inlet and outlet tubes represented schematically shortened for illustrative purposes), and a band of fibrinolytic and/or anticoagulant material on the inlet tube to prevent fibrin and/or clot formation and thereby prevent occlusion of the system.

In another additional or alternative potential strategy, as shown in FIG. 6, a fibrinolytic coating 190 is provided on at least a portion of the first tube 120 that is exposed to the pleural fluid. Such a fibrinolytic coating 190 can serve to break down fibrin, fibrin clots, fibrin strands, fibrin membranes, fibrinous septa and any other fibrinous debris in the fluid, which will allow the fluid to pass through the filtered automatic pump-based fluid management system 102. Examples of fibrinolytic factors for the fibrinolytic coating 190 include plasmin, tissue plasminogen activator, urokinase, streptokinase, plasminogen activator inhibitor-1 inhibitor, and plasminogen activator inhibitor-2 inhibitor. Other examples of fibrinolytics may be used.

Figure 7:
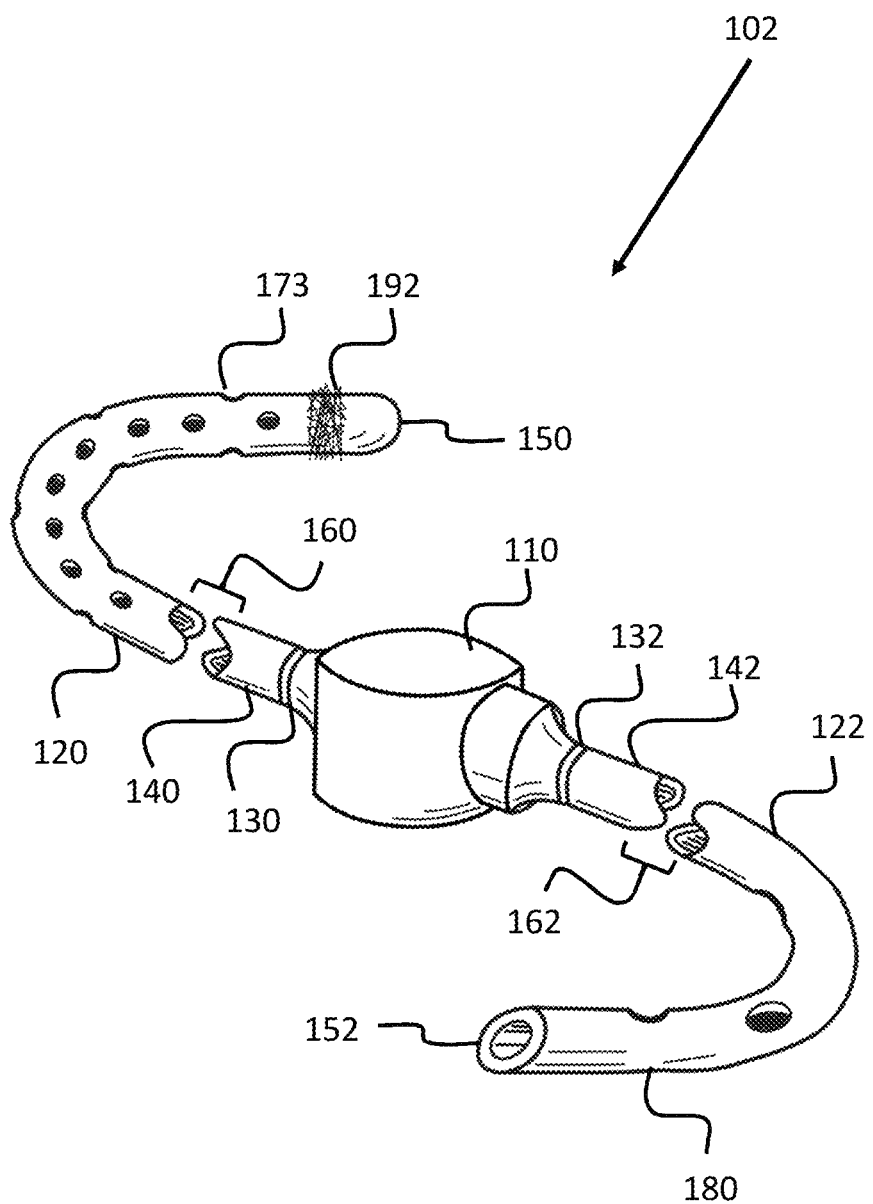
FIG. 7 shows a perspective view of an automatic pump-based fluid management system including a pump, perforated or fenestrated inlet and outlet tubes (inlet and outlet tubes represented schematically shortened for illustrative purposes), and a band of pro-fibrotic material on the inlet tube to induce localized fibrin and/or clot formation away from the fenestrations and thereby prevent occlusion of the system.

In another additional or alternative strategy, as shown in FIG. 7, a fibrin scavenger 192 is provided on at least a portion of the first tube 120 that is exposed to the pleural fluid. The fibrin scavenger is designed to convert fibrinogen to fibrin and bind it to the tip of the catheter such that it is no longer free in the pleural fluid to enter the fluid pathway of the automatic pump-based fluid management system 102. Examples of fibrin scavengers include thrombin, factor XIIIa, surface roughness, surface texture, micro-fibers, and dacron. Other fibrin scavengers or other approaches to convert fibrinogen to fibrin can also be used to scavenge fibrin from the pleural fluid so that it is no longer free in the pleural fluid to clog the fluid pathway of the automatic pump-based fluid management system 102.

In an additional or alternative strategy to prevent clogging, the fluid inlets, fluid outlets, first tube, second tube, or any other aspect of automatic pump-based fluid management system may be coated in anticoagulation factors or fibrinolytic factors. For example, the components or surfaces of the pump 110, first tube 120, or second tube 122 may be coated at least in part with anticoagulation factors or fibrinolytic factors. The presence of the anticoagulation factors may reduce the amount of clotting that would otherwise occur if they were not present. Examples of anticoagulation factors include heparin, low molecular weight heparin, fondaparinux, idraparinux, idrabiotaparinux, diabigatran, rivaroxaban, apixan, betrixaban, edoxaban, darexaban, letaxaban, eribaxaban, hirudin, lepirudin, bivalirudin, argatroban, dabigatran, ximelagatran, hementin, vitamin E, coumarin, warfarin, acenocoumarol, phenprocoumon, atromentin, phenindione, brodifacoum, and difenacoum. Examples of fibrinolytic factors include plasmin, tissue plasminogen activator, urokinase, streptokinase, plasminogen activator inhibitor-1 inhibitor, and plasminogen activator inhibitor-2 inhibitor. Other examples of anticoagulation factors or fibrinolytics may be used.

In another additional or alternative potential strategy, to prevent clogging or to deal with clogging should it occur, the walls of the automatic pump 110 may be constructed using a material that can be punctured with a needle or similar object for the instillation of, for example, anticoagulants, fibrinolytics, or other suitable material(s) into the interior of the automatic pump-based fluid management system 100. Alternatively, and as described further below, access ports may be added to the automatic pump 110 that allow also for the instillation of, for example, anticoagulants, fibrinolytics, or other suitable materials into the interior of the automatic pump-based fluid management system 100.

In an additional or alternative strategy to prevent clogging, patients may be selected based on favorable pleural effusion characteristics as demonstrated by transthoracic ultrasound of the pleural cavity 220 that are unlikely to clog the system. For example, use of the automatic pump-based fluid management system may be limited to patients who have an anechoic (clear fluid) as demonstrated by transthoracic ultrasound of the pleural cavity 220. Other pleural effusion characteristics such as complex septated effusions, homogeneously echogenic effusions, complex non-septated effusions, or combinations of characteristics may be favorable as well.

2. Automatic Intercostal Pump-Based Fluid Management System

Figure 8A:
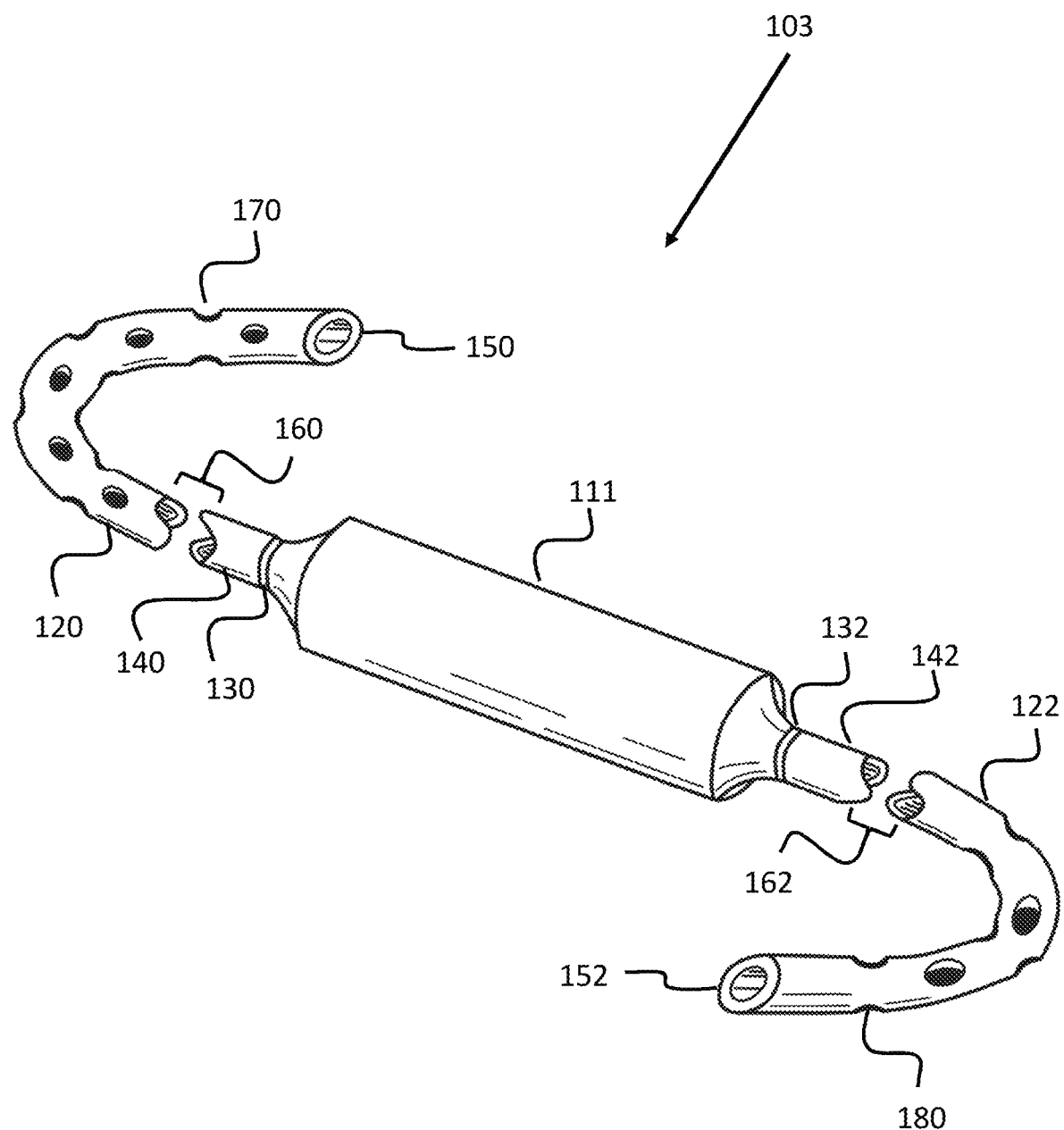
FIG. 8A shows a perspective view of an automatic intercostal pump-based fluid management system for intercostal uses, and including a pumping chamber and including perforated or fenestrated inlet and outlet tubes (inlet and outlet tubes represented schematically shortened for illustrative purposes)

With reference to FIG. 8A, an automatic intercostal pump-based fluid management system 103 for placement between a first rib and a second rib comprises a pump 111 that is generally, a resiliently flexible structure enclosing an interior space and having an inlet 130 and an outlet 132. Automatic intercostal pump 111 may be made of any suitable material that allows for pump 111 to be compressed and then freely returned to its original state. For example, the pump 111 may be a resiliently flexible tube or cylinder made of polyurethane, silicone, polyvinyl chloride, or latex rubber. Alternatively, the pump 111 may be made of a combination of two or more materials where at least one of the component materials provides resilience and at least one of the component materials provides fluid containment. For example, the pump 111 may be composed of an elastic nitinol, steel, polyester, or other elastic component to provide for resiliency and a second fluid containment component such as polyurethane, silicone, polyvinyl chloride, latex rubber, polyethylene terephthalate, nylon, polytetrafluoroethylene, PEBAX, or the like to provide fluid containment within the pump 111.

Although pump 111 is shown as generally cylindrical, other configurations are possible. In short, pump 111 may be any shape providing for suitable compression/decompression and placement in an intercostal region. In particular, it may be desirable to conform, to some extent, pump 111 to the characteristics (i.e., shape and/or space) of a particular region. In an embodiment, pump 111 may comprise flexible silicone tubing. However, pump 111 may take other forms as well.

Automatic intercostal pump-based fluid management system 103 also comprises a first tube 120 and a second tube 122. Inlet 130 and outlet 132 each communicate between the interior and the exterior of intercostal pump 111 and are coupled to the first tube 120 and the second tube 122, respectively. In other words, inlet 130 and outlet 132 are configured so as to provide for fluid communication between first tube 120 and second tube 122, respectively, and an interior space of intercostal pump 111.

First tube 120 comprises a tube-inlet end 150 and a pump-inlet end 140. Generally, first tube 120 is configured so that when automatic intercostal pump-based fluid management system 103 is in use, tube-inlet end 150 may be disposed in an area of a person's body from which fluid is to be drained. On the other hand, pump-inlet end 140 is coupled to inlet 130 of intercostal pump 111. Accordingly, the length of first tube 120 may vary, as depicted by length extension 160.

Similarly, second tube 122 comprises a pump-outlet end 142 and a tube-outlet end 152. Generally, second tube 122 is configured so that when automatic intercostal pump-based fluid management system 103 is in use, tube-outlet end 152 may be disposed in an area of a person's body to which fluid is to be drained. On the other hand, pump-outlet end 142 is coupled to outlet 132 of intercostal pump 111. Accordingly, the length of second tube 122 may vary, as depicted by length extension 162.

Although first tube 120 and second tube 122 are shown as entering into intercostal pump 111 in a substantially straight manner (i.e., perpendicular to a wall of the pump 111), first tube 120 and second tube 122 may be configured to enter intercostal pump 111 at any desired angle. For example, it may be desirable for first tube 120 and second tube 122 to enter and leave, respectively, intercostal pump 111 at about 90 degree angles so as to enable intercostal pump 111 to be situated in the intercostal region in a more advantageous manner. It may be desirable for first tube 120 and second tube 122 to enter and leave at other angles as well.

Although tubes 120 and 122 are generally shown as flexible tubing that may be easily manipulated and/or shaped to take any form or direction, in some embodiments it may be desirable for tubes 120 and 122 to be rigidly or semi-rigidly defined, to some extent, so that a desired shape or direction of the tubes may be maintained. For example, one of the tubes may be at least partially rigidly or semi-rigidly configured, shaped, or cast so that it has a 90-degree bend upon leaving intercostal pump 111. Each of tubes 120 and 122 may be configured to a similar 90-degree bend. Alternatively, the tubes may not have similar bends. As yet another alternative, the tubes may each have a bend of some other degree.

With reference to FIG. 8A, first tube 120 may comprise one or more fluid-inlet perforations 170. Fluid-inlet perforations 170 may take the form of holes in the surface of first tube 120 allowing for the intake of fluid into first tube 120 through not only tube-inlet end 150, but through fluid-inlet perforations 170 as well. Fluid-inlet perforations 170 may improve the volume or efficiency of fluid intake into first tube 120, and thereby, may improve the volume or efficiency of fluid drained by intercostal pump-based fluid management system 103. Fluid-inlet perforations 170 may be particularly advantageous as allowing for alternative fluid inlet locations in the event that tube-inlet end 150, or other perforations, become blocked due to, for example, fibrin clots, fibrin strands, or other debris, or apposition of the first tube 120 against the chest wall or lung. Second tube 122 may also include fluid-outlet perforations 180.

Figure 8B:
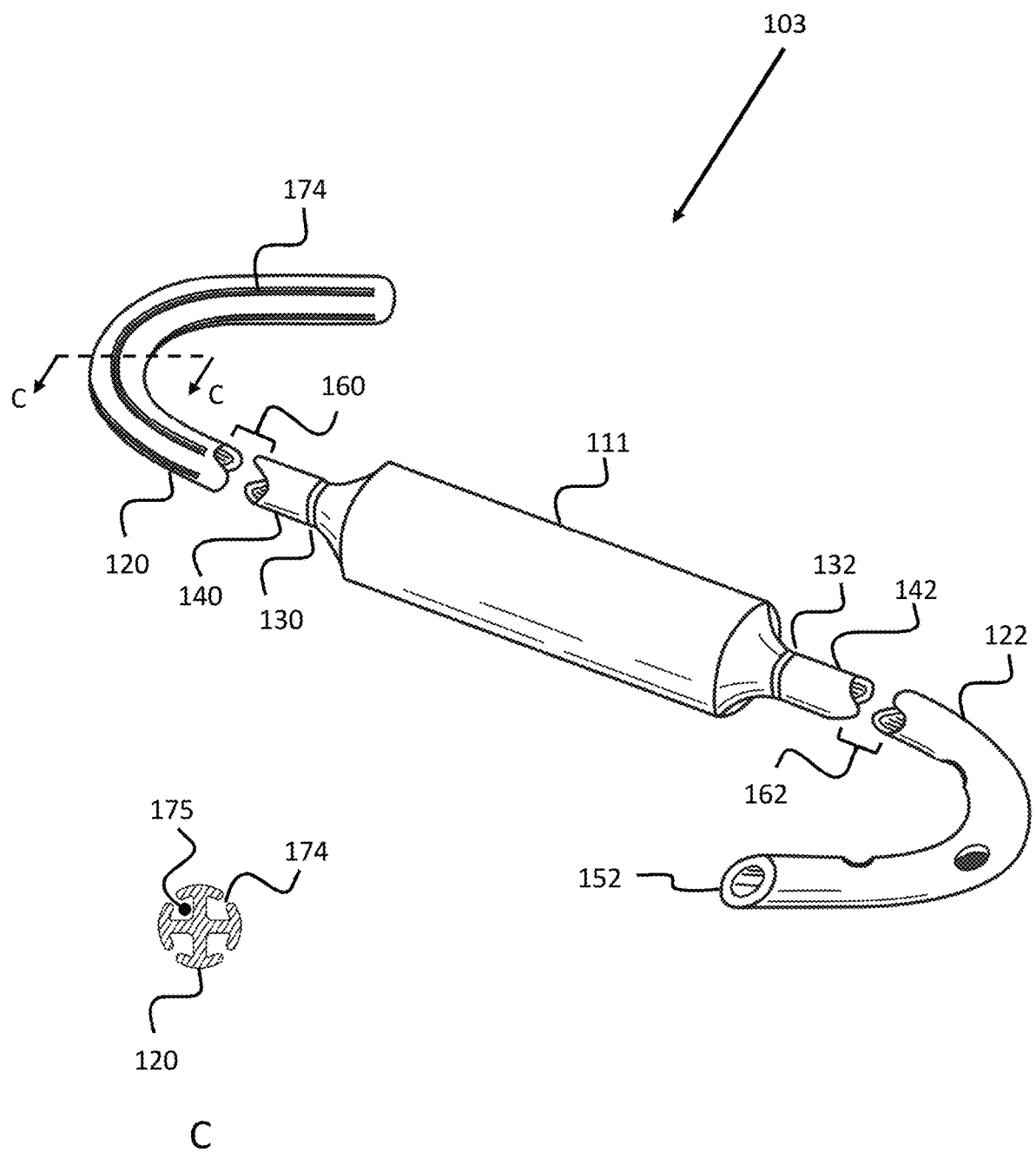
FIG. 8B shows a perspective view of an automatic intercostal pump-based fluid management system for intercostal uses, and including a pumping chamber and inlet tube with linear fluid channels and perforated or fenestrated outlet tube (inlet and outlet tubes represented schematically shortened for illustrative purposes)

With reference to FIG. 8B and inset cross-section C illustrated therein, first tube 120 may comprise one or more linear fluid channels 175. Liner fluid inlet slits 174 in the surface of the first tube 120 open into the linear fluid channels 175 allowing for the intake of fluid into the into the linear fluid channels 175 of the first tube 120. In combination, these features provide redundancy against clogging of the first tube 120. Linear fluid inlet slits 174 may be particularly advantageous by allowing near continuous access to the interior of the first tube 120 along the a significant portion of its length, such that if a single slit or a portion of multiple slits become blocked due to, for example, fibrin clots, fibrin strands, or other debris, or apposition of the first tube 120 against the chest wall or lung, the first tube 120 overall is still capable of allowing the passage of fluid into its interior and along its length. Further, the linear fluid intake slits 174 can be sized so as to limit the size of particulates or debris that enter into the linear fluid channels 175. This size can be chosen so as to prevent entry of particulates or debris that are large enough to clog the lumen of the linear fluid channels 175 or any other narrowing within the automatic intercostal pump-based fluid management system 103.

Automatic intercostal pump-based fluid management system 103 described with respect to FIG. 8A and FIG. 8B may additionally or alternatively include any other features, materials, or characteristics described with respect to the automatic pump-based fluid management systems of FIGS. 4-7.

3. Pleuroperitoneal Intercostal Pump-Based Fluid Management System

Figure 9:
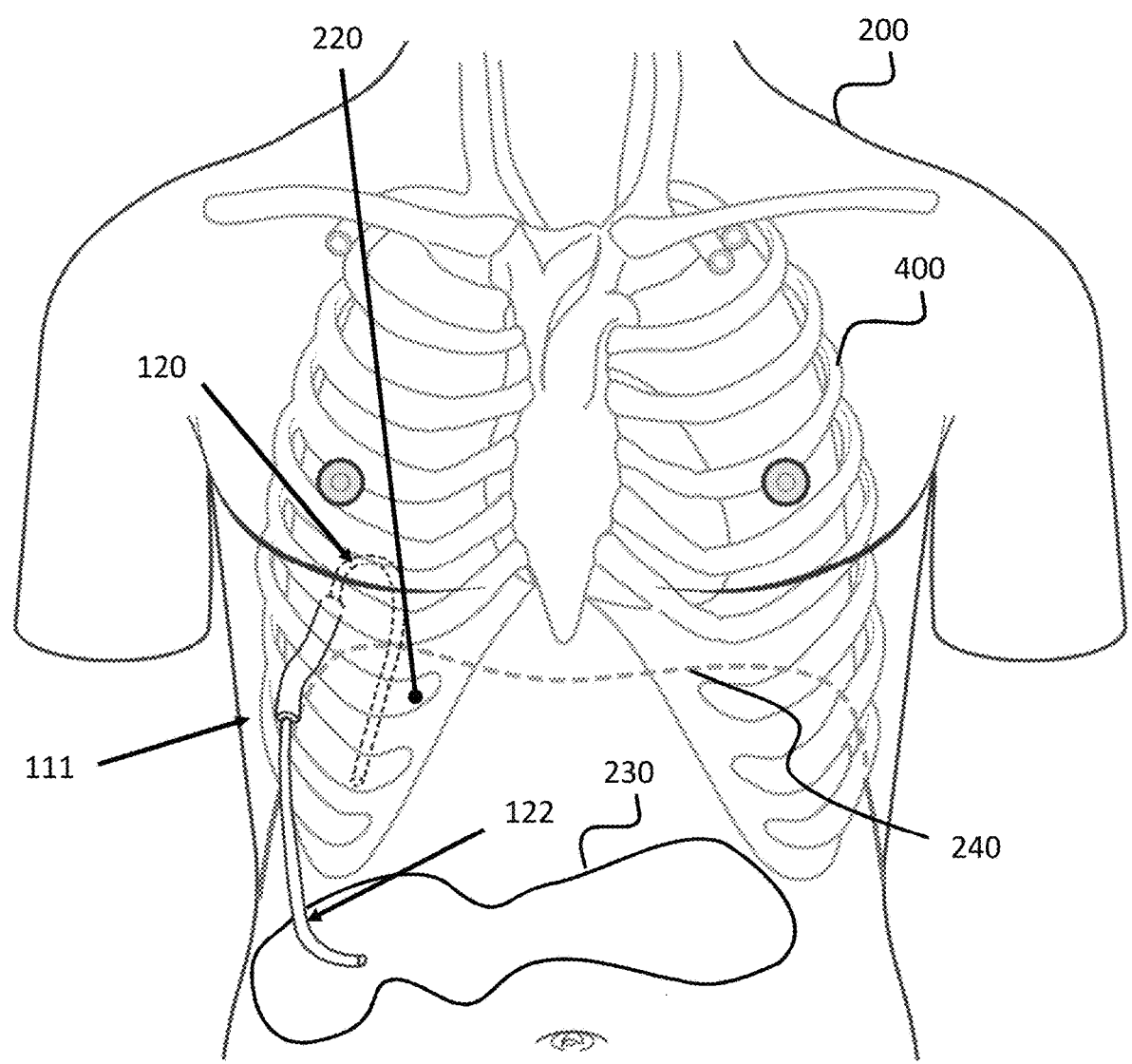
FIG. 9 shows an automatic intercostal pump-based fluid management system implanted in a patient.

With reference to FIG. 9, automatic intercostal pump-based fluid management system 103 is shown implanted in a patient 200, providing for drainage of fluid from a first area 220 to a second area 230 within the patient's body. In one embodiment, as in the embodiment depicted in FIG. 9, fluid is drained from a patient's pleural cavity to the patient's peritoneal cavity. In such an embodiment, therefore, first area 220 is the patient's pleural cavity and second area 230 is the patient's peritoneal cavity.

In an embodiment, automatic intercostal pump 111 is configured so that it may be placed, at least partially, in the intercostal region between two ribs. In other words, when implanted, intercostal pump 111 extends through the patient's intercostal space, or at least a portion thereof. Accordingly, first tube 120, and correspondingly, pump inlet 130, are disposed on the interior of the patient's rib cage. Second tube 122, and correspondingly, pump outlet 132, are disposed on the exterior of the patient's rib cage. In this way, upon breathing and the corresponding compression/decompression of the rib cage, patient 210 will automatically cause intercostal pump 111 to operate (e.g., "pump"). The operation of intercostal pump 111 is discussed further below.

4. The Automatic Intercostal Pump a. Automatic Intercostal Pump Design

Figure 10A:
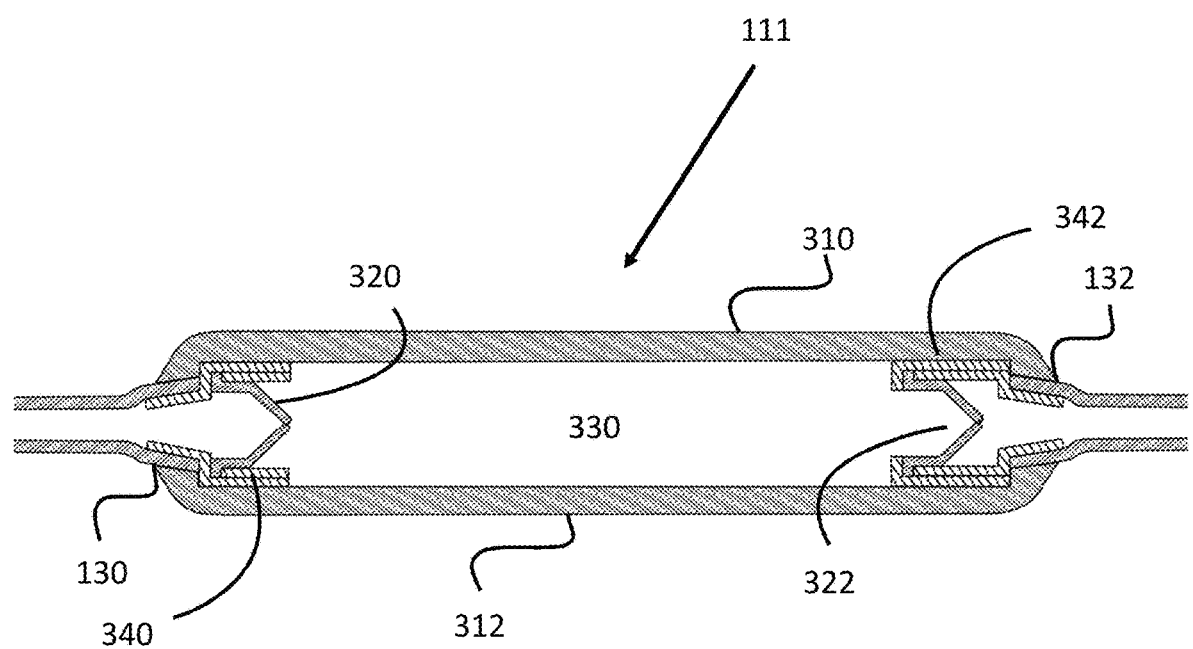
FIGS. 10A, 10B, 10C, and 10D show cross-sectional schematic views of a pumping chamber with a one-way inlet valve and a one-way outlet valve and various positions or states of the inlet and outlet one-way valves when the pumping chamber is compressed.

FIG. 10A shows a cross-sectional schematic view of an automatic intercostal pump 111 in a generally or substantially non-compressed state with both the inlet one-way valve 320 and outlet one-way valve 322 (described in further detail below) closed. As noted above, automatic intercostal pump 111 may be, generally, a resilient flexible tube or cylinder made of polyurethane, silicone, polyvinyl chloride, latex rubber or other appropriately resilient material. Alternatively, the pump 111 may be made of a combination of two or more materials where at least one of the materials provides resilience and at least one of the component materials provides fluid containment. For example, the pump 111 may be composed of a first resilient component such as elastic nitinol, steel, polyester, or other elastic component and a second fluid containment component such as polyurethane, silicone, polyvinyl chloride, latex rubber, polyethylene terephthalate, nylon, polytetrafluoroethylene, PEBAX, or the like to minimize leakage from within the intercostal pump 111. Other materials may be used.

Automatic intercostal pump 111 comprises a pump wall that encloses an interior space 330. For purposes of explanation, the pump wall is depicted as including upper wall 310 and lower wall 312. The distinction between an upper and lower wall is made for the purposes of clarity in explaining the compression/decompression of intercostal pump 111, and should not be interpreted as limiting intercostal pump 111 to comprise two distinct pump walls.

Generally, pump wall 310 (312) may be constructed of any material and of any thickness suitable to achieve desired flexibility and resilience of intercostal pump 111. The particular thickness of pump wall 310 (312) in a given embodiment may depend on, for example, the material of pump wall 310 (312) and the intended use (e.g., drainage function) of intercostal pump 111. In some embodiments, the pump wall 310 (312) may be made of silicone with an ASTM D2240 type A durometer ranging between about 30 to about 70 (Young's modulus between about 1.15 to about 5.5 MPa), preferably between about 40 and about 60 (Young's modulus between about 1.7 to about 3.6 MPa) and more preferably between about 45 and about 50 (Young's modulus between about 2.0 to about 2.5 MPa). In some embodiments, the intercostal pump 111 may comprise a generally or substantially cylindrical silicone structure having a substantially round cross section. The substantially cylindrical silicone structure may have an inner diameter between about 2 and about 14 mm, preferably between about 4 and about 10 mm, and more preferably between about 6 and about 7 mm; an outer diameter between about 3 and about 16 mm, preferably between about 6 and about 12 mm, and more preferably between about 8 and about 10 mm; and a wall thickness of about 0.3 to about 3 mm, preferably between about 0.5 and about 2 mm, and more preferably between about 0.7 and about 1.0 mm. In an embodiment, the substantially cylindrical structure may have an inner diameter of about 6.4 mm and an outer diameter of about 8 mm, with a corresponding wall thickness of about 0.8 mm. In other embodiments, the intercostal pump 111 may comprise a silicone structure having a substantially oval cross section or a substantially rectangular cross section. Other shapes and dimensions may be desirable as well.

Intercostal pump 111 further comprises inlet one-way valve 320 and outlet one-way valve 322. Inlet valve 320 may be situated in the interior space 330 of the pump body in general proximity to inlet 130. Inlet one-way valve 320 may be any suitable one-way valve, and may, for example, be made of silicone or other suitable material. Inlet one-way valve 320 is configured so as to preclude or substantially preclude fluid movement from the interior space 330 of intercostal pump 111 to inlet 130. At the same time, inlet one-way valve 320 is configured to allow fluid movement from inlet 130 to the interior space 330 of intercostal pump 111. In other words, inlet one-way valve 320 is in fluid communication with inlet 130 so as to provide generally for one-way fluid movement from inlet 130 to interior space 330 of intercostal pump 110.

Correspondingly, outlet one-way valve 322 may be situated in the interior space 330 of the pump body in general proximity to outlet 132. Outlet one-way valve 322 may be any suitable one-way valve, and may, for example, be made of silicone or other suitable material. Outlet one-way valve 322 is configured so as to allow fluid movement from the interior space 330 of intercostal pump 111 to outlet 132. At the same time, outlet one-way valve 322 is configured to preclude or substantially preclude fluid movement from outlet 132 to the interior space 330 of intercostal pump 111. In other words, outlet one-way valve 322 is in fluid communication with outlet 132 so as to provide for one-way fluid movement from interior space 330 of intercostal pump 111 to outlet 132.

In an embodiment of intercostal pump 111, an inlet one-way valve frame 340 and an outlet one-way valve frame 342 have been added respectively to the outer perimeter of inlet one-way valve 320 and outlet one-way valve 322 so that the compression/decompression of intercostal pump 111 does not cause significant compression of, deformation of, or undesirable wear to, inlet one-way valve 320 and outlet one-way valve 322. The inlet one-way valve frame 340 and an outlet one-way valve frame 342 may each be constructed of any relatively stiff, or non-flexible material, for the outer perimeter of inlet one-way valve 320 and outlet one-way valve 322, respectively. Additionally, the size and shape of each of the inlet one-way valve frame 340 and outlet one-way valve frame 342 can be chosen to provide joining points or interconnectable joints between the first tube 120 and second tube 122 and the upper wall 310 and lower wall 312 of the intercostal pump 111. Other types of valve frames that can function so that the compression/decompression of intercostal pump 111 does not cause significant compression of, deformation of, or undesirable wear to, inlet one-way valve 320 and outlet one-way valve 322 may be used.

Note that, although inlet one-way valve 320 and outlet one-way valve 322 are depicted as situated within the interior space 330 of intercostal pump 111, alternative placement of the valves may be desirable as well. For example, one of, or both of, inlet one-way valve 320 and outlet one-way valve 322 might be situated exterior to the pump body, perhaps within inlet tube 120 and outlet tube 122, respectively, or between inlet tube 120 and the pump body or outlet tube 122 and pump body, respectively. The particular placement of the valves need not be critical, so long as they sufficiently provide substantially for one-way fluid flow into and out of intercostal pump 111.

b. Pump Operation

Figure 10B:
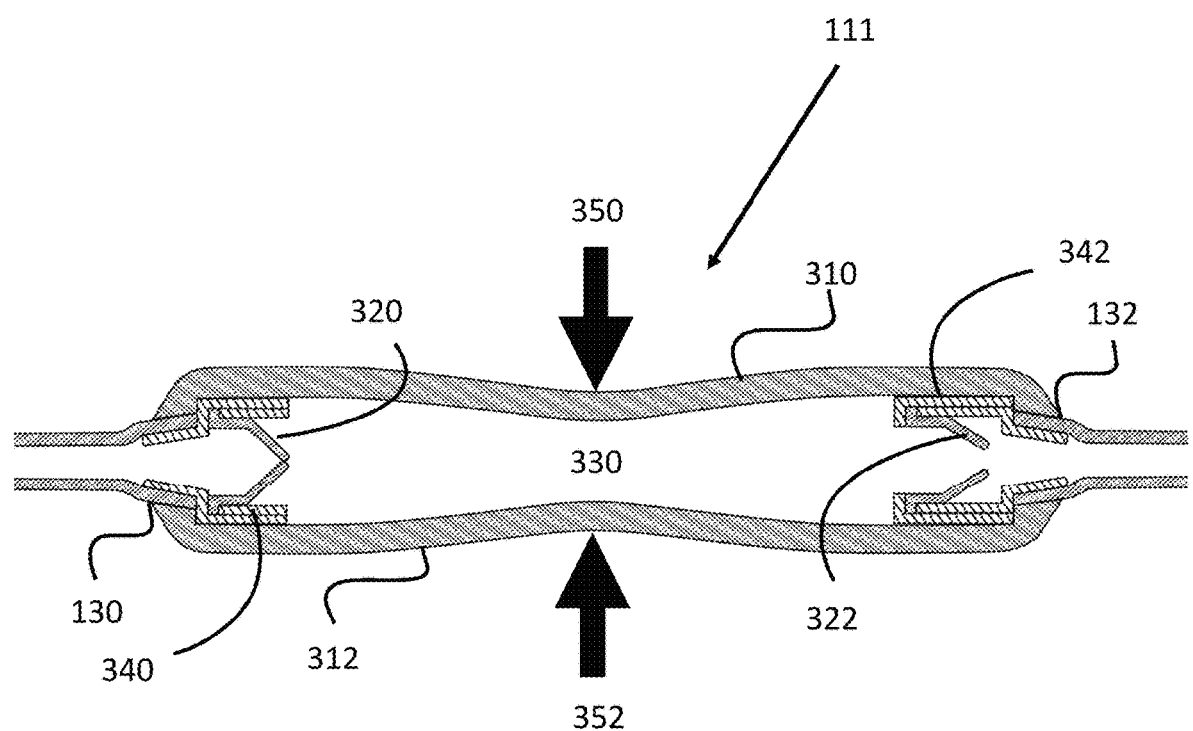

FIG. 10B shows a cross-sectional schematic view of intercostal pump 111 in a generally or substantially compressed state. In an embodiment, as shown, a first force 350 may act on upper wall 310 causing upper wall 310 to collapse in towards interior space 330. Correspondingly, a second force 352 may additionally or alternatively act on lower wall 312 causing lower wall 312 to collapse in towards interior space 330. The collapse of the upper wall 310 and/or lower wall 312 serves to decrease the volume of the interior space 330 and to increase the pressure in the interior space 330. This increase in pressure causes the inlet one-way valve 320 to remain closed and causes the outlet one-way valve 322 to open, and fluid located in the interior space 330 flows from the interior space 330 through the outlet one-way valve 322 and into the second tube 122. For incompressible fluids, the change of volume experienced by the interior space in response to the collapse of the upper wall 310 and/or lower wall 312 will be approximately equal to the volume of fluid that moves from the interior space 330 through the outlet one-way valve 322. As the fluid moves from the interior space 330 through the outlet one-way valve 322, the pressure in the interior space will decrease. Once the interior pressure about equals or substantially equals the pressure in the pump outlet 132, flow will stop and the outlet one-way valve 322 will close as shown in FIG. 10C.

Figure 10C:
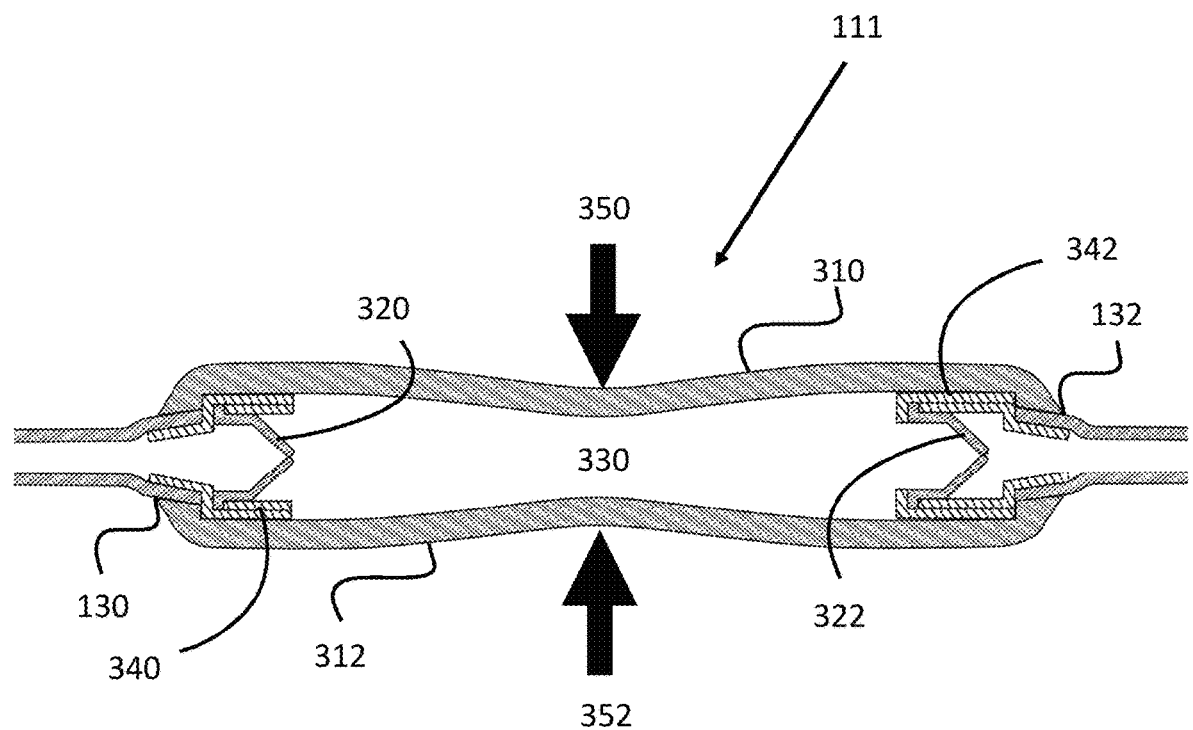
Figure 10D:
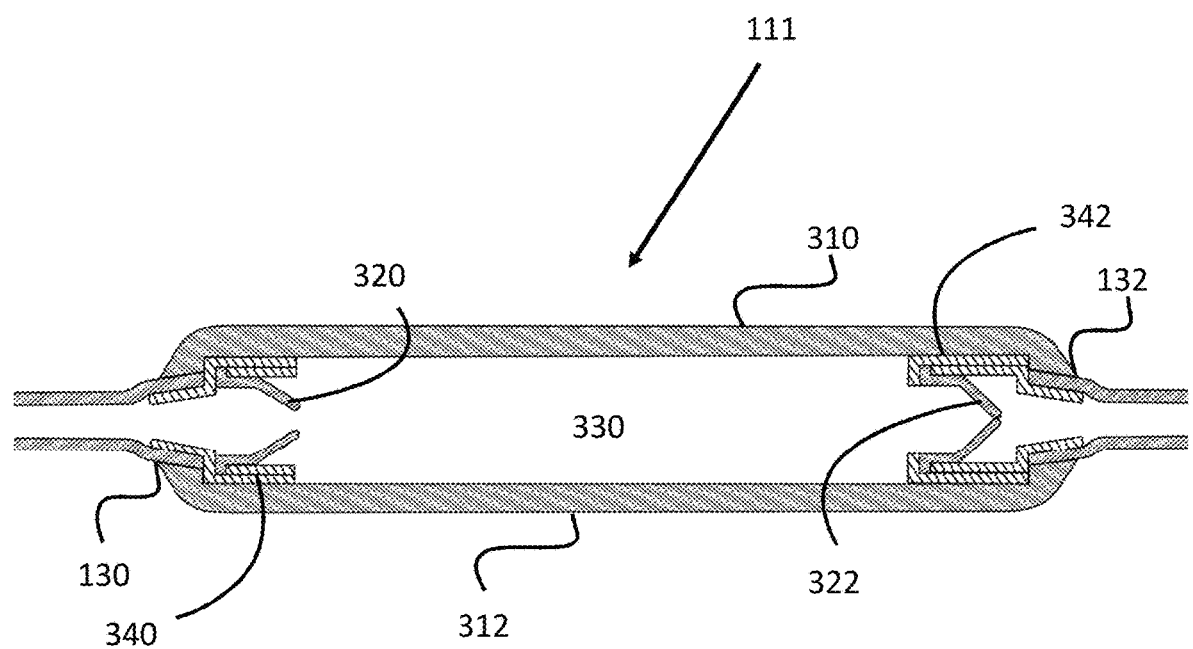

As described above, intercostal pump 111 is substantially resiliently flexible and therefore, after being placed in a compressed state as shown in FIGS. 10B and 10C, intercostal pump 111 will return to an uncompressed state as shown in FIG. 10D when at least one of the first force 350 and the second force 352 are removed. As the upper wall 310 returns to its uncompressed state as the first force 350 is removed and/or the lower wall 312 returns to its uncompressed state as the second force 352 is removed, the volume of the interior space 330 increases and the pressure in the interior space 330 decreases. The pressure inside the interior space 330 eventually drops below the pressure in the interior of the inlet and causes the inlet one-way valve 320 to open and fluid located in the inlet to flow into the interior space 330. In this way, intercostal pump 111 operates as a pump that, generally, draws fluid from its inlet 130 and passes it to its outlet 132.

Figure 10E:
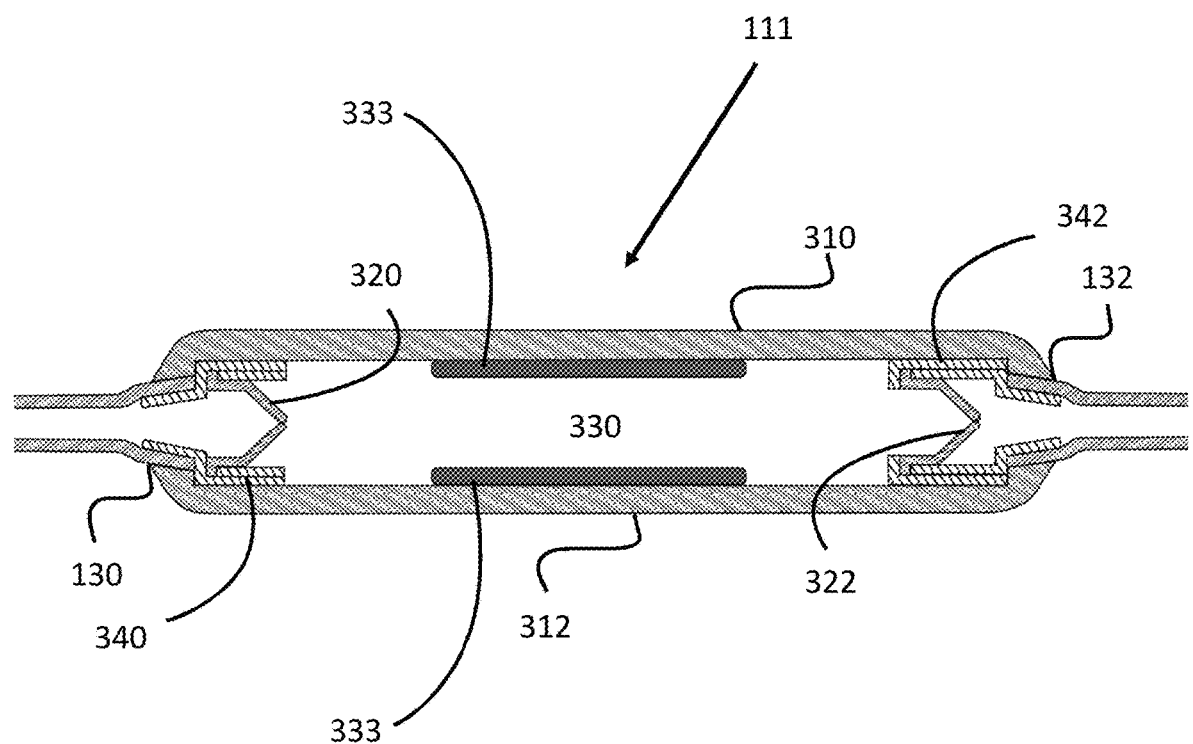
FIGS. 10E and 10F show cross-sectional schematic views of a pumping chamber with a one-way inlet valve and a one-way outlet valve and reinforcing members within the pumping chamber designed to provide greater volumetric changes to the pump chamber for a given application of force.
Figure 10F:
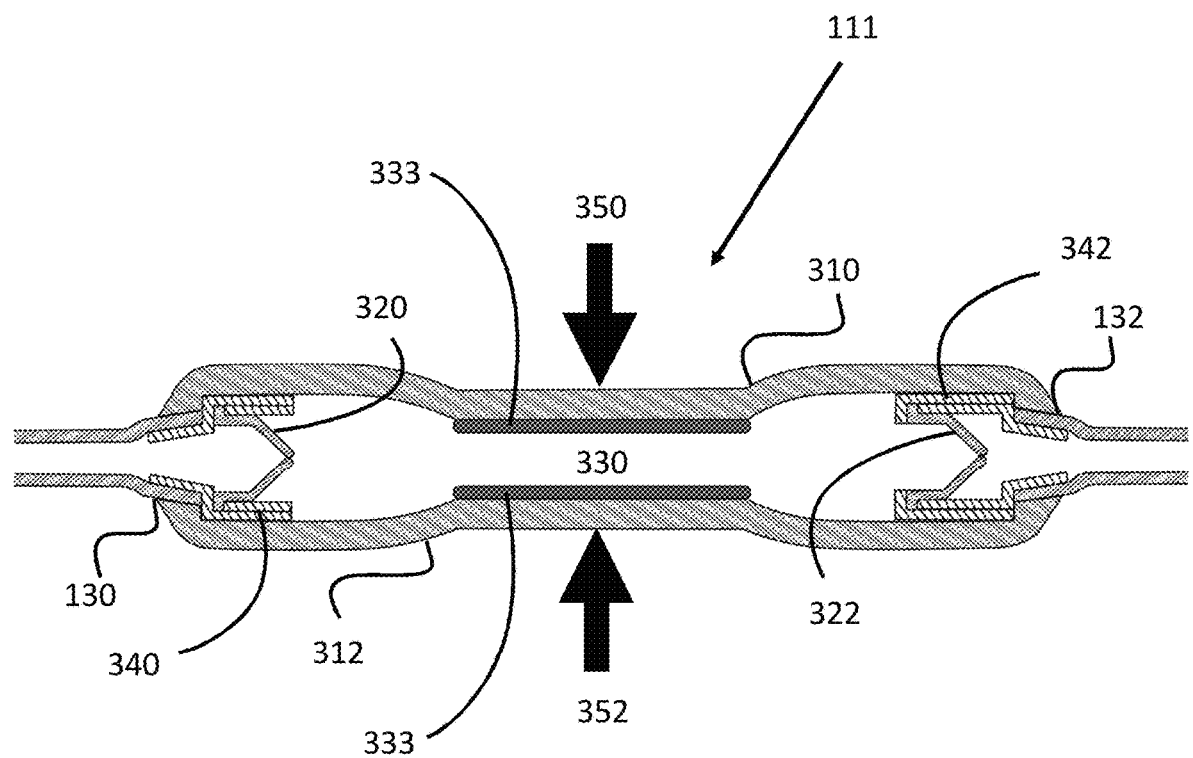

Additionally, as shown in FIGS. 10E and 10F, intercostal pump 111 may be constructed with reinforcing members 333 integrated into the wall or attached to the wall such that a larger volumetric change in the interior space 330 may occur when at least one of the first force 350 and the second force 352 are applied when compared to the volumetric change in the interior space 330 when the reinforcing members 333 are not present as shown in FIGS. 10A and 10B. This occurs as the reinforcing members 333 serve to distribute the relatively narrowly applied first force 350 and second force 352 along a greater length of the upper wall 310 and lower wall 312 of the pump thereby causing a greater change in the interior volume 330 of the pump. While reinforcing members 333 are shown as being located midway along the length of the upper wall 310 and lower wall 312 such that both ends of the reinforcing members 333 move together, it is also possible to position the reinforcing members 333 such that one end of each member is positioned in close proximity or even attached to the inlet one-way valve frame 340 or outlet one-way valve frame 342 such that the reinforcing member now acts as a lever arm providing even greater volumetric change to the interior space 330 when at least one of the first force 350 and the second force 352 are applied. Reinforcing members 333 can generally be any suitable size and shape and can be made from any suitable material, and in some cases can be made from any suitable material that is generally more rigid than the material forming the upper wall 310 and lower wall 312.

In use, intercostal pump 111 may be compressed as a result of patient breathing. More particularly, intercostal pump 111 may be compressed as a result of the natural movement of a patient's ribs during the breathing cycle. Additionally, the intercostal pump 111 may be placed such that the interior space 330 passes between fibers of the external intercostal or internal intercostal muscles and may be compressed as a result of these muscle fibers contracting.

Figure 11A:
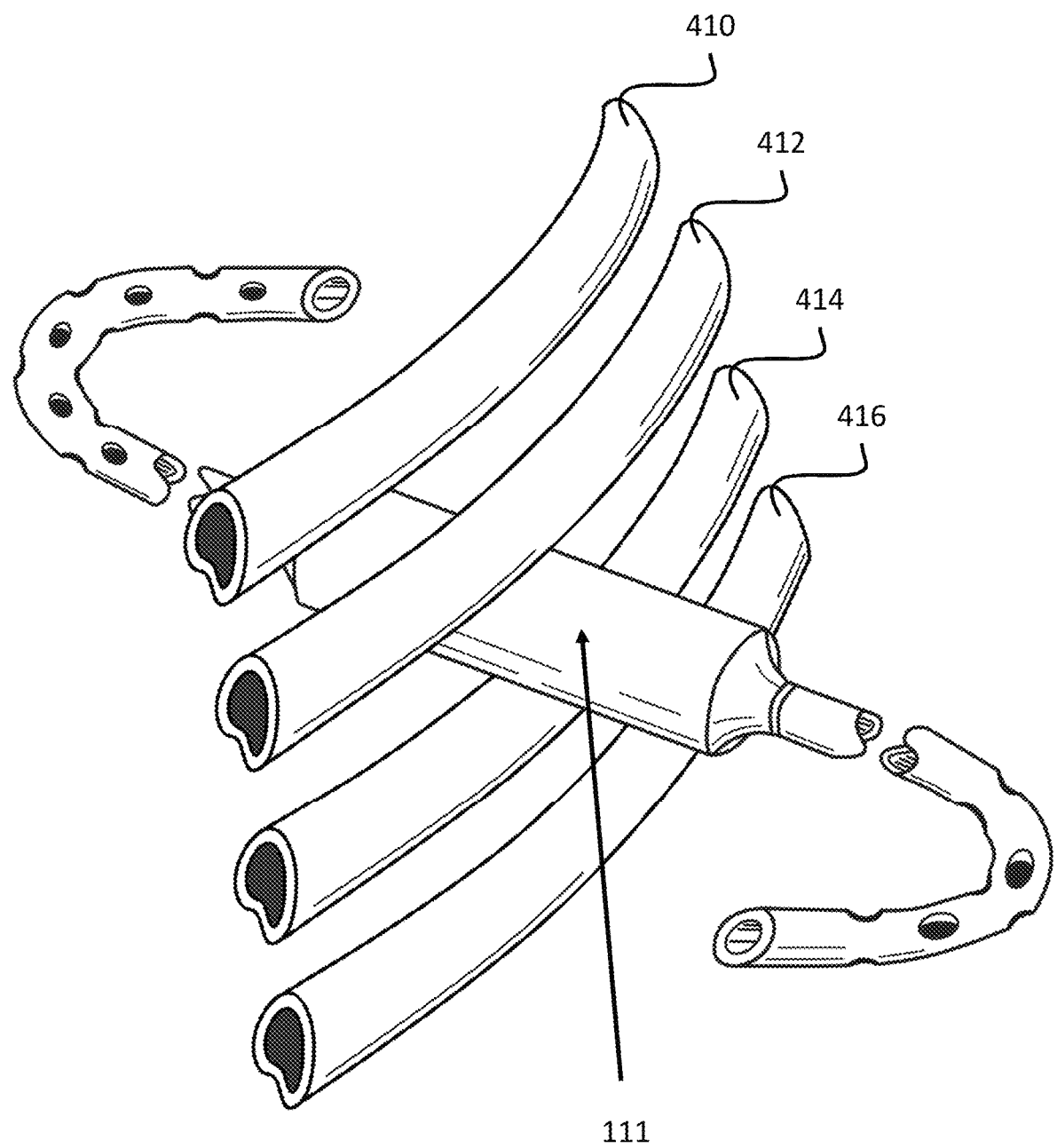
FIGS. 11A and 11B show perspective views of an automatic intercostal pump-based fluid management system and the relationship of the pumping chamber with respect to a patient's ribs during inspiration and expiration.

As shown in FIG. 11A, in use, intercostal pump 111 is placed between a first rib 412 and a second rib 414 selected from the ribs in the chest wall. References herein to a first rib and a second rib do not necessarily refer to, but could be, the first and second ribs anatomically. When the rib cage expands (upon inhaling), individual ribs 410, 412, 414, and 416 separate, and in this configuration of the ribs, relatively little force is exerted on intercostal pump 111. Therefore, intercostal pump 111 is in a generally or substantially uncompressed state.

Figure 11B:
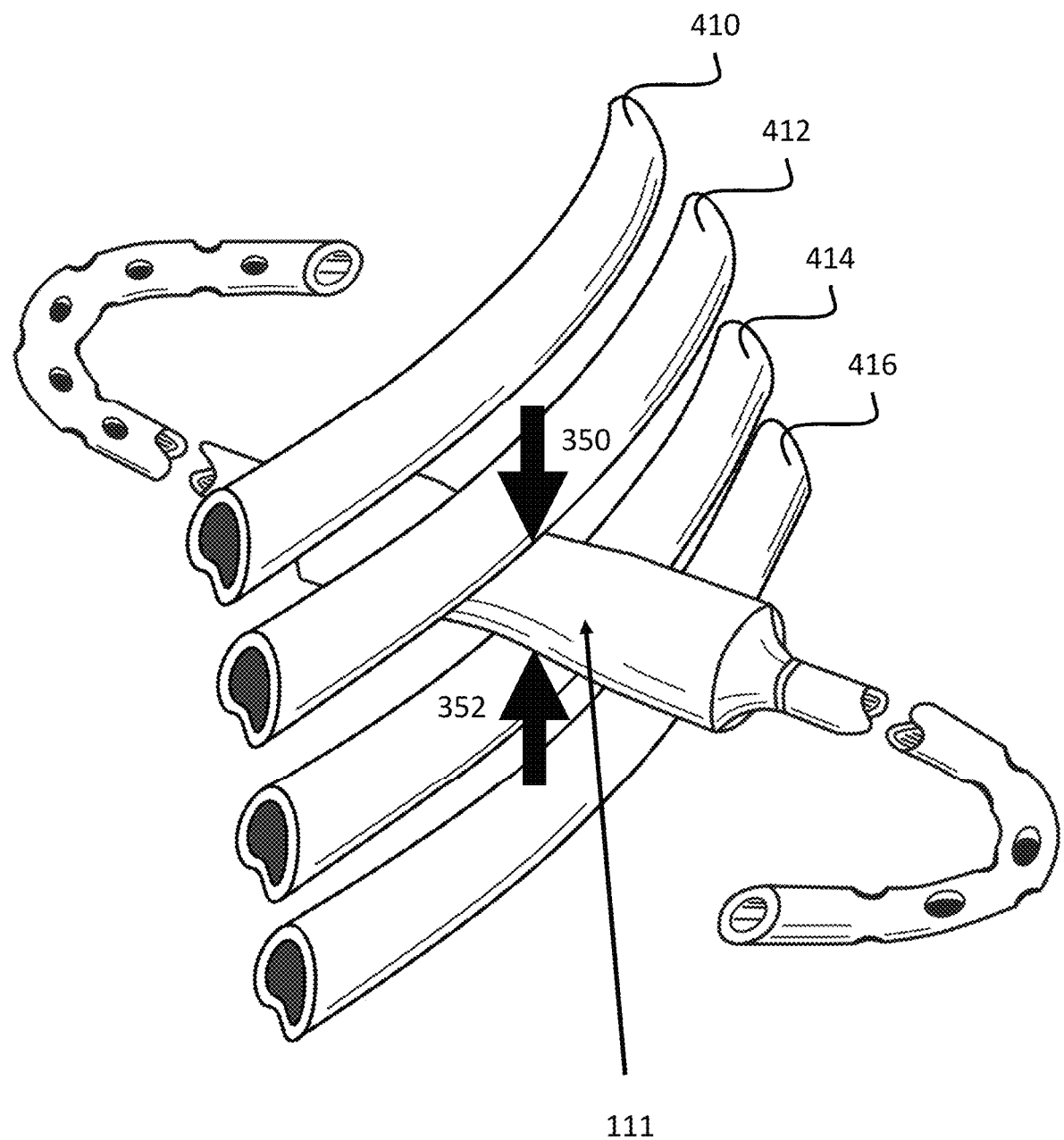

As shown in FIG. 11B, when the rib cage contracts (upon exhaling), individual ribs 410, 412, 414, and 416 move towards one another. As a result, a first force 350 and/or a second force 352 are exerted on intercostal pump 110 by a first rib 412 and/or a second rib 414, respectively. Therefore, intercostal pump 111 is in a generally or substantially compressed state.

An average adult takes about sixteen breaths per minute. Therefore, in use, intercostal pump 111 may be compressed approximately sixteen times per minute or 23,040 times in a day. Of course, this is only an approximation and may vary greatly. A particular compression rate need not be critical to the functioning of intercostal pump 111, though the rate at which fluid is pumped will vary with the compression rate and amplitude of compression (i.e., degree of rib motion).

An average adult exhibits approximately 0.25 to 3 millimeters of relative motion between a first rib 412 and second rib 414 throughout the breathing cycle. Accordingly, the walls of intercostal pump 111 may be compressed approximately 0.25 to 3 millimeters during each breath. Of course, this also is only an approximation and may vary greatly from patient-to-patient and for any given patient may vary depending on the specific anatomic first rib 412 and second rib 414 and the specific location along the length of the first rib 412 and second rib 414 relative to the spine and/or sternum.

A relevant consideration is that ribs are lined by soft tissue. The soft tissue may be compressible itself and therefore, if any soft tissue is left in place between intercostal pump 111 and either of a first rib 412 or second rib 414, the full extent of possible compression of intercostal pump 111 may be affected. In some cases, therefore, it may be desirable to remove soft tissue at the point of contact of intercostal pump 111 with either of a first rib 412 or second rib 414.

Another relevant consideration is that ribs generally exhibit portions that are relatively cartilaginous, which portions may be relatively compressible themselves. As a result, in some cases it may be desirable to place intercostal pump 111 so as to be in contact with portions of a first rib 412 and second rib 414 exhibiting a relatively low amount of cartilage (i.e., a portion of the rib having a relatively high amount of bone, as opposed to cartilage, exposed).

Yet another relevant consideration is that it may be desirable to situate intercostal pump 111 in such way that the amount of surface area of intercostal pump 111 that is in contact with each of a first rib 412 and second rib 414 is significantly increased or substantially maximized. In this way, intercostal pump 111 may experience a greater amount of compression. Therefore, it may be desirable to situate intercostal pump 111 in a manner substantially parallel to a first rib 412 and second rib 414 or at any angle between substantially perpendicular and substantially parallel to a first rib 412 and second rib 414, as opposed to the substantially perpendicular manner as generally indicated in FIGS. 11A and 11B.

Yet another relevant consideration is that it may be desirable to size the intercostal pump 111 relative to the distance between a first rib 412 and second rib 414 at end inhalation so that the intercostal pump 111 is at least partially compressed even when the first rib 412 and second rib 414 are relatively separated. In this way, changes to the distance between the first rib 412 and second rib 414 that occur during breathing may translate to larger volume changes within the intercostal pump 111.

Yet another relevant consideration is that it may be desirable to position the intercostal pump 111 relative to a first rib 412 and a second rib 414 so that the intercostal pump 111 may be cyclically deformed during breathing by the relative motions of a first rib 412, a second rib 414, other tissues of the chest wall, and/or the lung such that the volume of the interior space 330 of the intercostal pump 111 is cyclically changed with breathing leading to fluid being pumped.

c. Valve Construction

Figure 12:
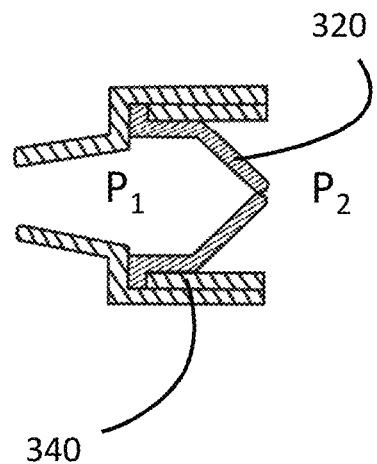
FIG. 12 shows cross-sectional schematic views of a one-way inlet valve in a closed state and open state and cross-sectional schematic views of a one-way outlet valve in a closed state and open state.
Figure 12:
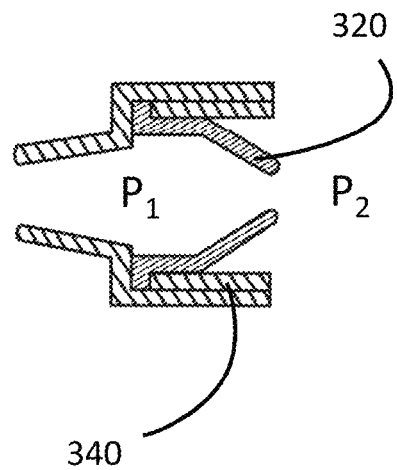
Figure 12:
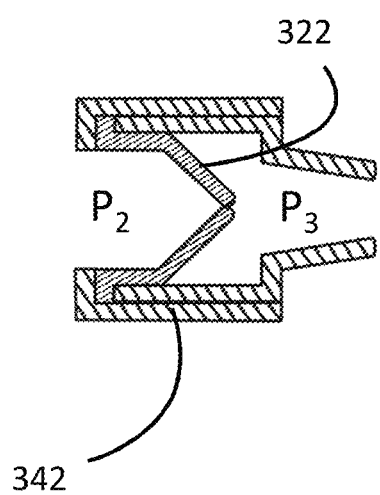
Figure 12:
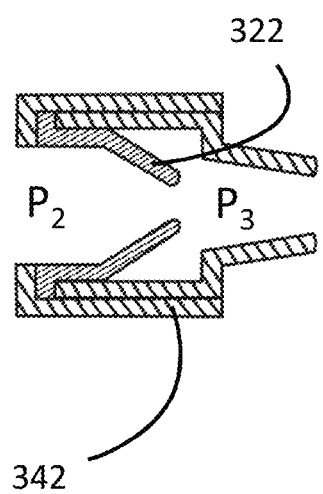

FIG. 12 shows cross-sectional views of one-way inlet valves in a closed state and open state and cross-sectional views of one-way outlet valves in a closed state and open state. In panel A, an inlet one-way valve 320 is shown in a closed state with an inlet one-way valve frame 340 enclosing and providing structure and support to the inlet one-way valve 320. In panel B, an inlet one-way valve 320 is shown in an open state. The size and shape of the inlet one-way valve frame 340 can be chosen to provide joining points or interconnectable joints to the first tube 120. In panel C, an outlet one-way valve 322 is shown in a closed state with an outlet one-way valve frame 342 enclosing and providing structure and support to the outlet one-way valve 322. In panel D, an outlet one-way valve 322 is shown in an open state. The size and shape of the inlet one-way valve frame 342 can be chosen to provide joining points or interconnectable joints to the first tube 122.

For the inlet one-way valve 320, when it is in a closed position as shown in panel A of FIG. 12, the pressure differential across the valve is such that pressure $P_1 \leq P_2 + P_c$, where $P_1$ and $P_2$ are the pressures in the locations shown in panel A and $P_c$ is the cracking pressure of the valve. Similarly, when the inlet one-way valve 320 is in an open position as shown in panel B of FIG. 12, the pressure differential across the valve is such that pressure $P_1 > P_2 + P_c$, where $P_1$ and $P_2$ are the pressures in the locations shown in panel B and $P_c$ is again the cracking pressure of the valve.

For the outlet one-way valve 322, when it is in a closed position as shown in panel C of FIG. 12, the pressure differential across the valve is such that pressure $P_2 \leq P_3 + P_c$, where $P_2$ and $P_3$ are the pressures in the locations shown in panel C and $P_c$ is the cracking pressure of the valve. Similarly, when the outlet one-way valve 322 is in an open position as shown in panel D of FIG. 12, the pressure differential across the valve is such that pressure $P_2 > P_3 + P_c$, where $P_2$ and $P_3$ are the pressures in the locations shown in panel D and $P_c$ is again the cracking pressure of the valve.

In an embodiment, the inlet one-way valve 320 and outlet one-way valve 322 are formed as a duckbill valve having thin and substantially planar lips that define a slit that can move from a closed to an open position. In an embodiment, the inlet one-way valve 320 and outlet one-way valve 322 may have low cracking pressures, $P_c$, such that the valves transition from a closed state to an open state with relatively small differential pressures across the valve. This cracking pressure, $P_c$, can be less than about 25 cmH$_2$O to operate in most patients, preferably less than about 15 cmH$_2$O, more preferably less than about 10 cmH$_2$O or even less than about 5 cmH$_2$O. In an embodiment, the inlet one-way valve 320 and outlet one-way valve 322 can have low resealing pressures, such that the valves transition from an open state to a closed state with small differential pressures across the valves. This resealing pressure can be less than about 15 cmH$_2$O to operate in most patients, preferably less than about 10 cmH$_2$O, more preferably less than about 5 cmH$_2$O or even less than about 2 cmH$_2$O.

Additionally, in an embodiment, the inlet one-way valve 320 and outlet one-way valve 322 are configured to undergo minimal deformation when closed and a pressure gradient exists across the valves opposite to their one-way direction. Specifically, the inlet one-way valve undergoes minimal deformation when a back-pressure exists across the valve, i.e., when $P_1 \leq P_2 + P_c$, and the outlet one-way valve undergoes minimal deformation when a back-pressure exists across the valve, i.e., when $P_2 \leq P_3 + P_c$. With such design, volumetric changes that occur in the interior space 330 of the pump body translate approximately or substantially one-to-one into forward flow through the automatic intercostal pump 111. This resistance to deformation can be assessed as a volumetric back-flow that occurs when a back-pressure is applied across a sealed or closed inlet one-way valve 320 and outlet one-way valve 322. With an applied back-pressure of 50 cmH$_2$O or less, back-flow may be less than about 200 microliters to operate in most patients, preferably less than about 100 microliters, more preferably less than about 50 microliters or even less than about 25 microliters. As such, the amount of volume pumped forward ($V_{forward}$) with each cycle will be close to, substantially equal, or equal the volume change of the internal space 330 of the pump ($\Delta V_{internal\ space}$) minus the volumetric deformation of the valve required to reseal the valve is ($V_{reseal\ volume}$). Generally stated another way:

$$V_{forward} = \Delta V_{internal\ space} - V_{reseal\ volume}$$

Nonlimiting examples of valves that may be used for one-way valves 320, 322 are the type described in U.S. Pat. No. 5,261,459, titled "Miniature Duckbill Valve Having a Low Cracking Pressure and High Flow Rate," which is hereby incorporated by reference herein in its entirety.

d. Alternative Pleuroperitoneal Automatic Intercostal Pump Designs

Figure 13:
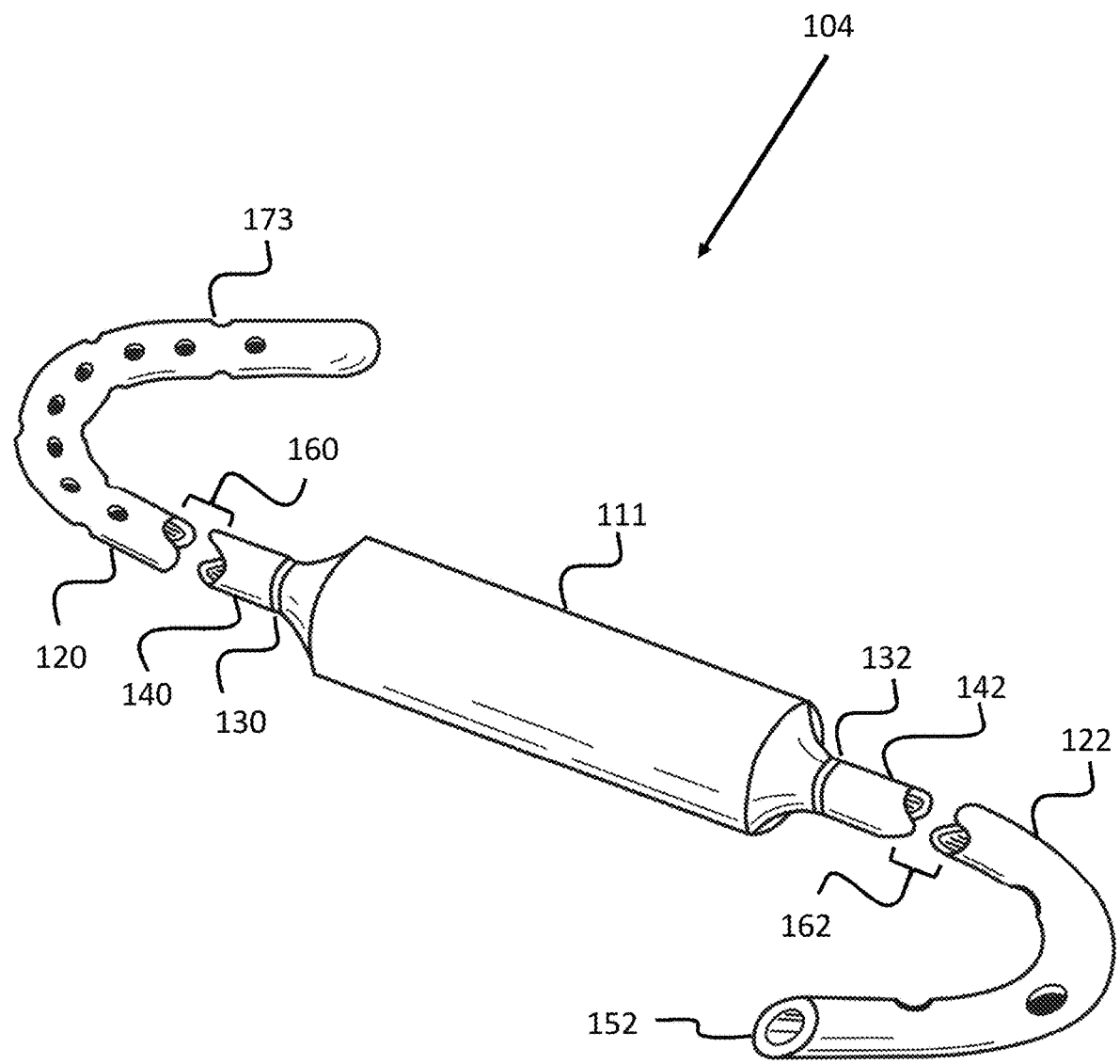
FIG. 13 shows a perspective view of an automatic intercostal pump-based fluid management system including a pumping chamber and an inlet tube with a rounded and closed end, inlet holes sized relative to the inlet and outlet valves, and an outlet tube (inlet and outlet tubes represented schematically shortened for illustrative purposes)

Any aspect, feature, characteristic, etc., or combination thereof, of the automatic pump-based fluid management system described in FIGS. 1-7 may also be incorporated into the automatic intercostal pump-based fluid management system of FIGS. 8-12. As an example, in order to prevent blocking or clogging of the automatic intercostal pump-based fluid management system and maintain flow through the system, the first tube 120 can be constructed so as to provide a filtering mechanism for fluid entering the automatic intercostal pump-based fluid management system 104. With reference to FIG. 13, first tube 120 may comprise one or more filtering fluid-inlet perforations 173. Filtering fluid-inlet perforations 173 may take the form of holes in the wall of first tube 120 allowing for the intake of fluid into first tube 120. Filtering fluid-inlet perforations 173 are sized and shaped such that any fibrinous clots, fibrinous strands, or other debris that are able to pass through the filtering perforations 173 can also pass through the entire fluid pathway of the filtered automatic intercostal pump-based fluid management system 104 without occluding or significantly obstructing fluid flow. Alternatively, filtering fluid-inlet perforations 173 are sized and shaped such that each and every such perforation is smaller than the smallest opening that exists along the entire fluid pathway of the filtered automatic intercostal pump-based fluid management system 104. For example, filtering fluid-inlet perforations 173 may be sized and shaped such that they are smaller than the openings in the inlet one-way valve 320 and the outlet one-way valve 322. As such, any fibrinous clots, fibrinous strands, or other debris that can pass through the filtering fluid-inlet perforations 173 will be smaller than the smallest openings in the fluid pathway of the filtered automatic pump-based fluid management system 104, and as such should be able to pass through the fluid pathway of the filtered automatic pump-based fluid management system 102. As illustrated in FIG. 13, the tube-inlet end of the first tube 120 may comprise a closed-end, and in some cases may be rounded or smoothed to assist placement of the first tube 120.

Figure 14A:
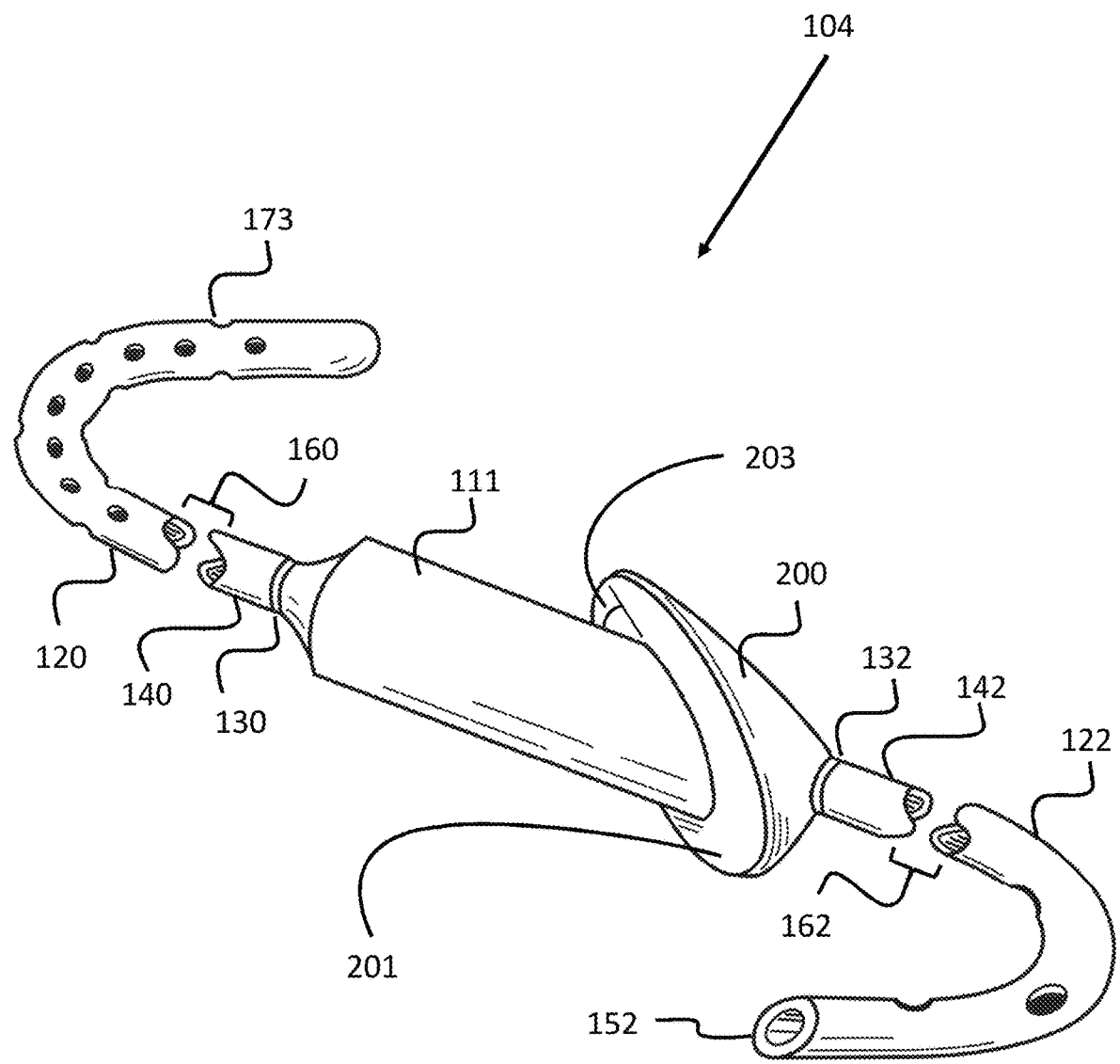
FIG. 14A shows a perspective view of an automatic intercostal pump-based fluid management system including a pumping chamber, an inlet tube, an outlet tube, and a stability and orientation feature (inlet and outlet tubes represented schematically shortened for illustrative purposes)
Figure 14B:
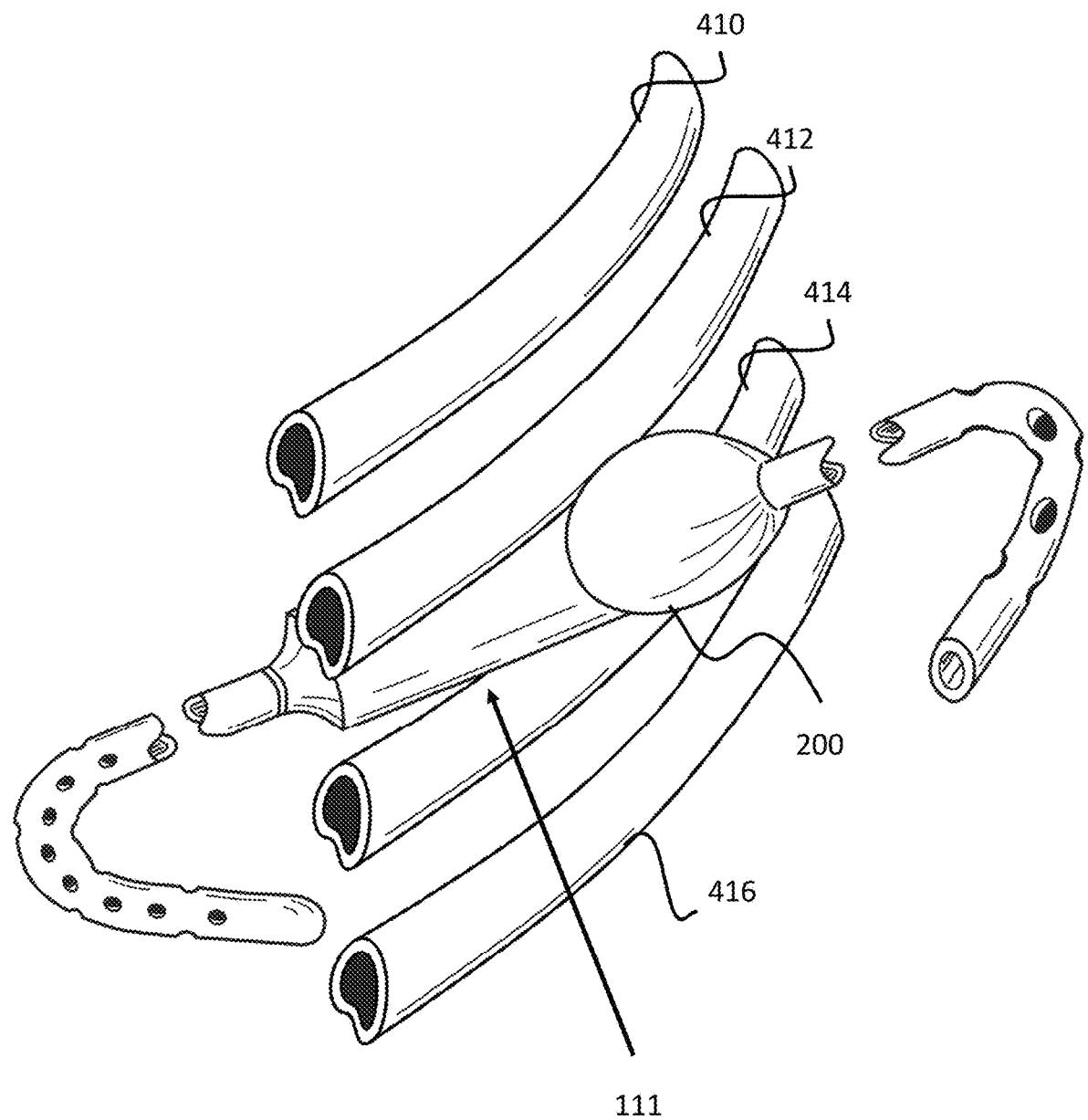
FIG. 14B shows a perspective view of the automatic intercostal pump-based fluid management system with a stability and orientation feature and the relationship of the pumping chamber with respect to a patient's ribs.

Providing for a stable position and orientation of the intercostal pump 111 in the intercostal space between a first rib and a second rib of the pump may be beneficial. With reference to FIG. 14A, a stability and orientation feature 200 is provided on and in some cases around the intercostal pump, for example in proximity to the outlet portion of the intercostal pump 111. The stability and orientation feature 200 in FIG. 14A is shown as a relatively rounded, generally conical feature with a relatively planar surface 201 that is annular or partially annular to the intercostal pump 111 body and is oriented at a suitable angle 203 to the long axis of the intercostal pump 111. In use, as shown in FIG. 14B, when the intercostal pump 111 is positioned between a first rib 414 and a second rib 416, the planar surface 201 of the stability and orientation feature 200 interfaces with the first rib 414 and a second rib 416 and any intervening soft tissue to orient the intercostal pump 111 at a desired angle, generally determined by angle 203, relative to the chest wall, and to provide stability at this angle and stability against movement of the intercostal pump along its axis relative to the chest wall. While shown generally rounded and conical, the overall shape of the stability and orientation feature 200 can be of any shape that essentially serves to orient the intercostal pump 111 relative to the chest wall and/or to provide for stability of that orientation and/or axial position of the intercostal pump 111 relative to the chest wall.

Figure 15A:
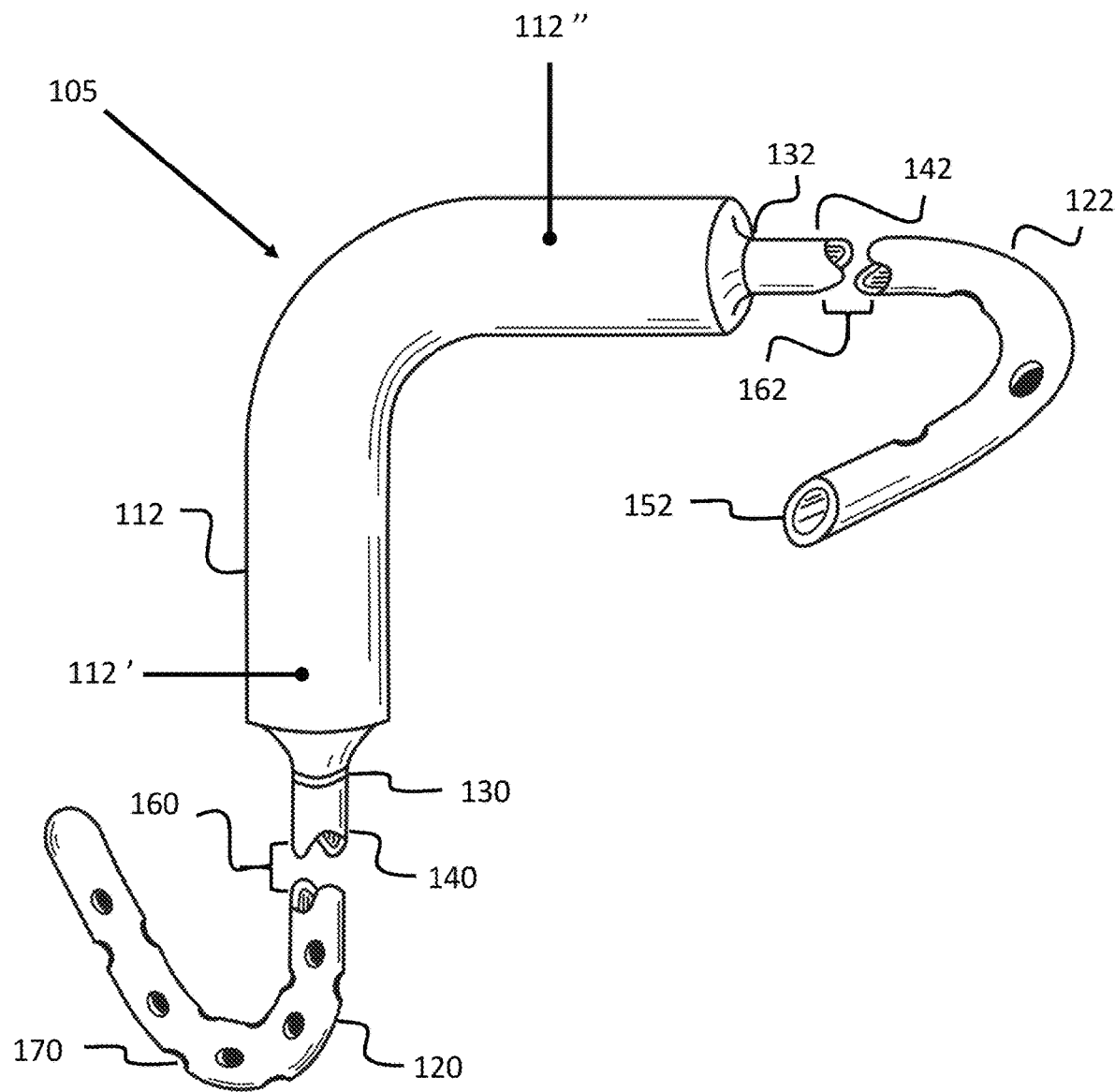
FIG. 15A shows a perspective view of an automatic intercostal pump-based fluid management system including a pump that is shaped to better accommodate the transition from the pleural space to subcutaneous tissues and including a perforated or fenestrated inlet and outlet tube (inlet and outlet tubes represented schematically shortened for illustrative purposes)
Figure 15B:
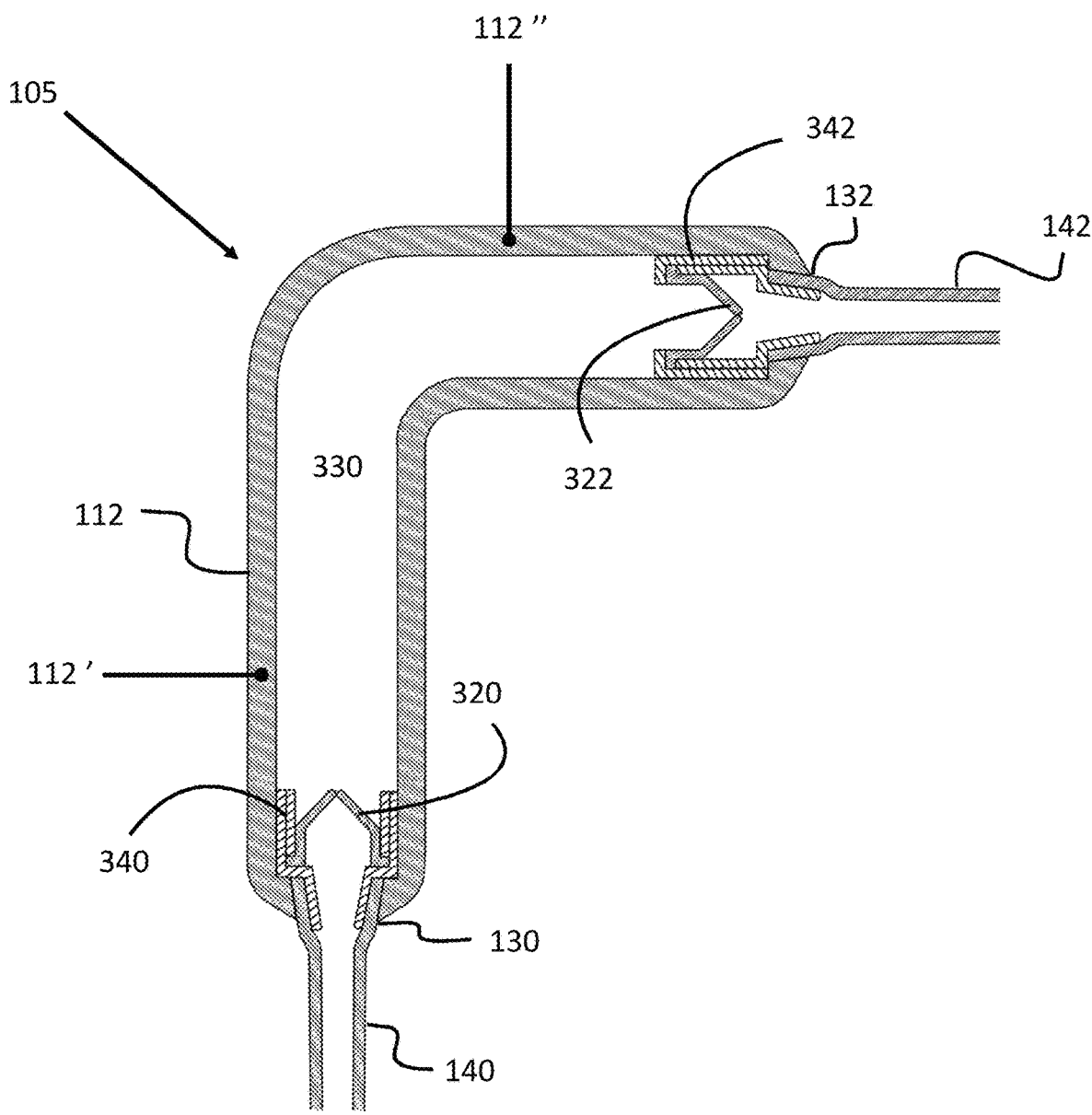
FIG. 15B shows a cross-sectional schematic view of the pump of the automatic intercostal pump-based fluid management system shown in FIG. 15A.

To better accommodate the transition between the pleural cavity and the subcutaneous tissues between the skin and ribcage, still further embodiments can be constructed. As shown in FIG. 15A, a fitted automatic intercostal pump-based fluid management system 105 includes a fitted pump 112 that is roughly or substantially 'L-shaped' to better accommodate the transition from the pleural space to subcutaneous tissues. In more general terms, fitted pump 112 may be shaped with an angled portion or transition portion that provides for an angled transition of the pump 112 (e.g., between portions 112' and 112", described below) of between about 1 degree to 179 degrees, preferably between about 45 degrees and 135 degrees, more preferably between about 75 degrees and 105 degrees, and in some cases roughly about 90 degrees. When placed in a patient, the intercostal portion 112' of the fitted pump 112 is placed in an intercostal space between a first rib and a second rib and the subcutaneous portion 112" of the pump 112 is placed in the subcutaneous tissues under the skin and on the outer portion of the rib cage. In this configuration and placement, as the patient breathes, the intercostal portion 112' of the pump 112 is cyclically compressed and decompressed by the first rib and second rib as described, for example, with respect to FIG. 11A and FIG. 11B thereby automatically providing a continuous pumping action on the pump and flow of fluid from the pleural cavity to the peritoneal cavity. Additionally, in this configuration and placement, the subcutaneous portion 112" of the pump 112 is located on the outside of the rib cage and is accessible for cyclic (or non-cyclic) manual compression between the skin and the ribcage that can provide additional pumping action of the pump 112, when desired, to supplement fluid flow from the pleural cavity to the peritoneal cavity. FIG. 15B shows a cross-sectional schematic view of the pump 112 of the fitted automatic intercostal pump-based fluid management system 105.

Figure 16A:
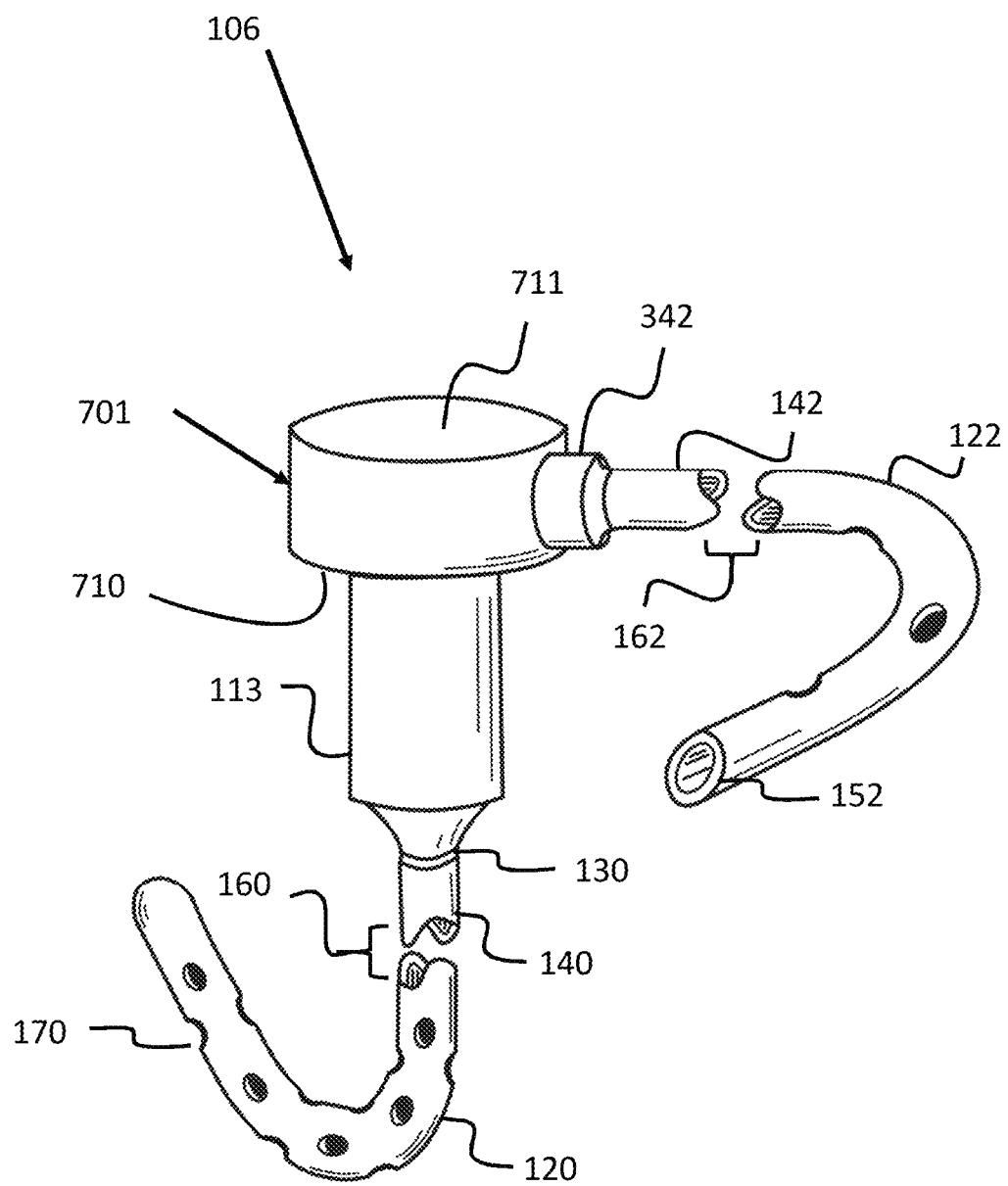
FIG. 16A shows a perspective view of an automatic intercostal pump-based fluid management system including a pump that is shaped to better accommodate the transition from the pleural space to subcutaneous tissues and to better prevent displacement once placed and including a perforated or fenestrated inlet and outlet tube (inlet and outlet tubes represented schematically shortened for illustrative purposes)
Figure 16B:
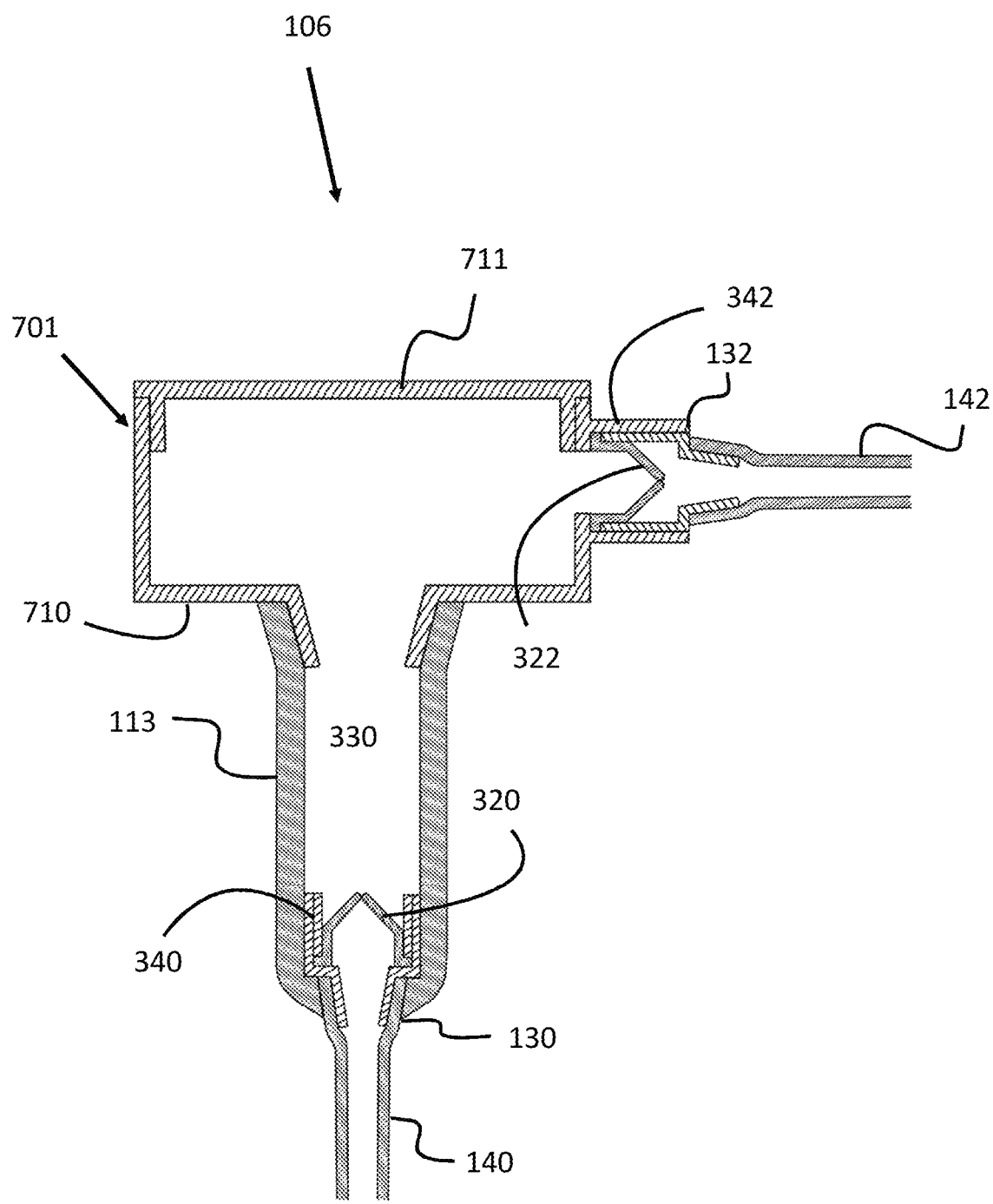
FIG. 16B shows a cross-sectional schematic view of the pump of the automatic intercostal pump-based fluid management system shown in FIG. 16A.

Another alternative to better accommodate the transition between the pleural cavity and the subcutaneous tissues of the chest wall as well as provide for stable positioning is shown in FIG. 16A. A transitioned automatic intercostal pump-based fluid management system 106 includes an intercostal pump 113 connected to a transitioning chamber 701 to better accommodate the transition from the pleural space to subcutaneous tissues. The transitioning chamber 701 is shown as a cylinder with intercostal pump 113 connected to a flat first end 710 of the cylinder, a flat second end 711 on an opposite side of the cylinder from the flat first end 710, and an outlet one-way valve frame 342 integrated into or attached to the wall of the cylinder. When placed in a patient, the intercostal pump 113 is placed in an intercostal space between a first rib and a second rib and the transitioning chamber 701 of the transitioned automatic intercostal pump-based fluid management system 106 is placed in the subcutaneous tissues under the skin and on the outer portion of the rib cage. In this configuration and placement, as the patient breathes, the intercostal pump 113 is cyclically compressed and decompressed by the first rib and second rib as described, for example, with respect to FIG. 11A and FIG. 11B thereby automatically providing a continuous pumping action on the pump and flow of fluid from the pleural cavity to the peritoneal cavity. Additionally, in this configuration and placement, the transitioning chamber 701 is located on the outside of the rib cage and provides for a roughly or substantially 90 degree (or other suitable angle) transition from the of the pump inlet end 140 of the first tube 120 to the pump outlet end 142 of the second tube 122 to better accommodate the transition from the pleural cavity to the subcutaneous tissues. The flat first end 710 of the cylinder provides a stable interface of the transitioning chamber 701 with the rib cage and helps maintain stable positioning of the intercostal pump 113 in the intercostal space between a first rib and a second rib. While the transitioning chamber 701 is shown as a flat ended cylinder, it can take any appropriate shape that provides for an up to 90 degree (or other suitable angle) transition from the pump inlet end 140 of the first tube 120 to the pump outlet end 142 of the second tube 122 and stability of the intercostal pump. The transitioning chamber 701 may be constructed of any relatively stiff, or non-flexible material such as nylon, acrylic, polycarbonate, PEEK, ABS, PET, stainless steel, or other suitable material. However, it can also be made of a relatively more flexible material as desired. FIG. 16B shows a cross-sectional schematic view of the pump 113 and transitioning chamber 701 of the transitioning automatic intercostal pump-based fluid management system 106.

Figure 17:
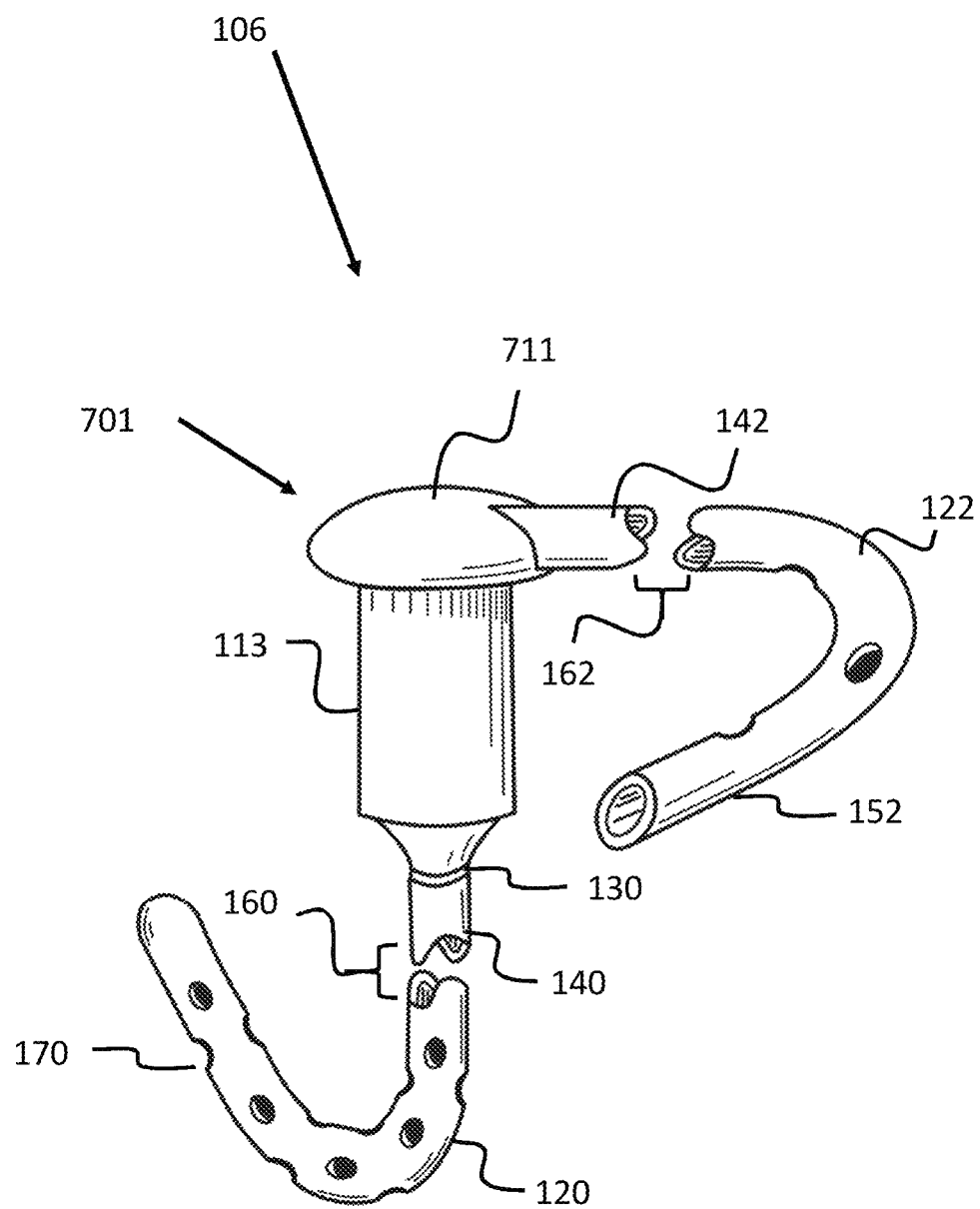
FIG. 17 shows a perspective view of an alternative automatic intercostal pump-based fluid management system including a pump that is shaped to better accommodate the transition from the pleural space to subcutaneous tissues and to better prevent displacement once placed (inlet and outlet tubes represented schematically shortened for illustrative purposes)
Figure 18:
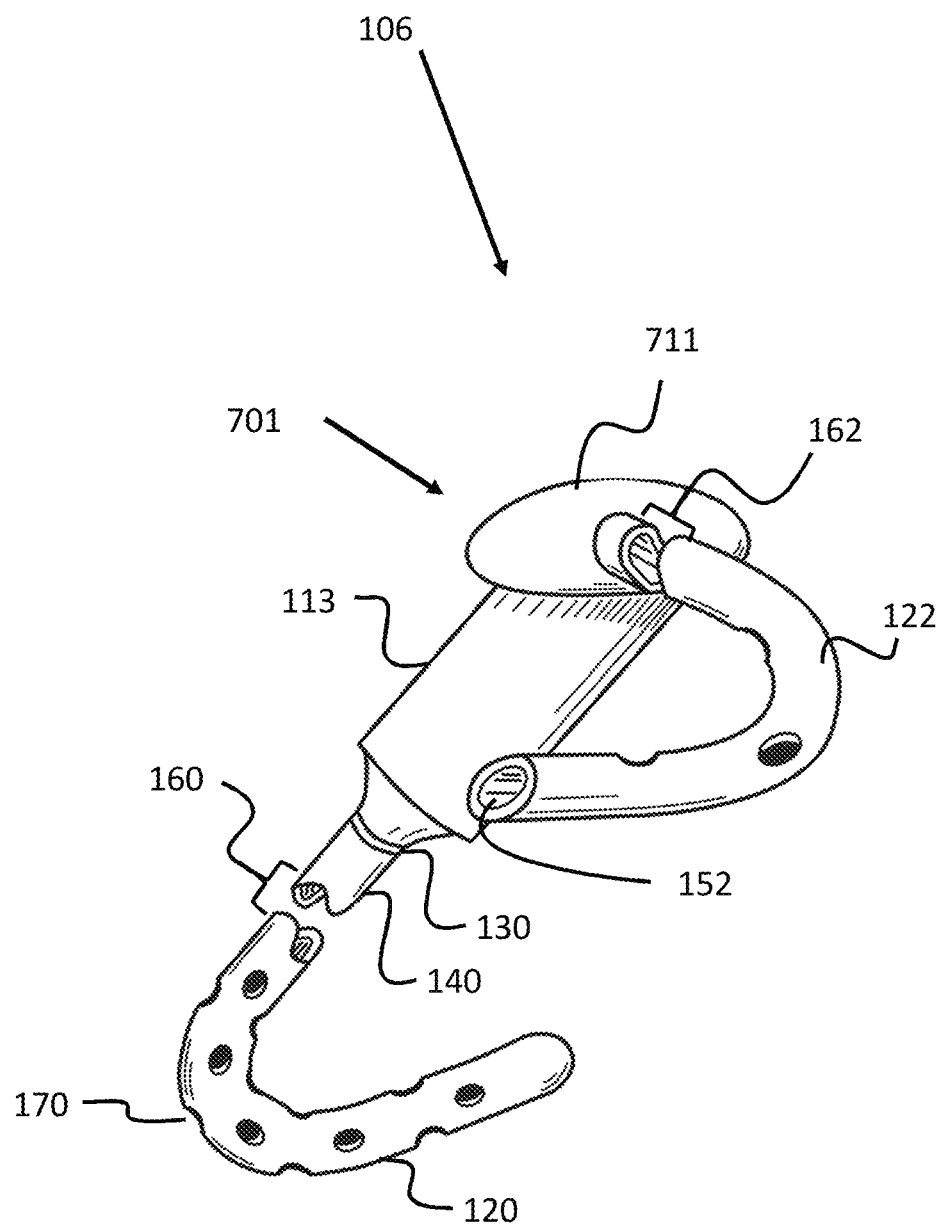
FIG. 18 shows a perspective view of an alternative automatic intercostal pump-based fluid management system including a pump that is shaped to better accommodate the transition from the pleural space to subcutaneous tissues, to provide an arbitrary orientation angle of the pump relative to the chest wall, and to better prevent displacement once placed (inlet and outlet tubes represented schematically shortened for illustrative purposes)
Figure 19:
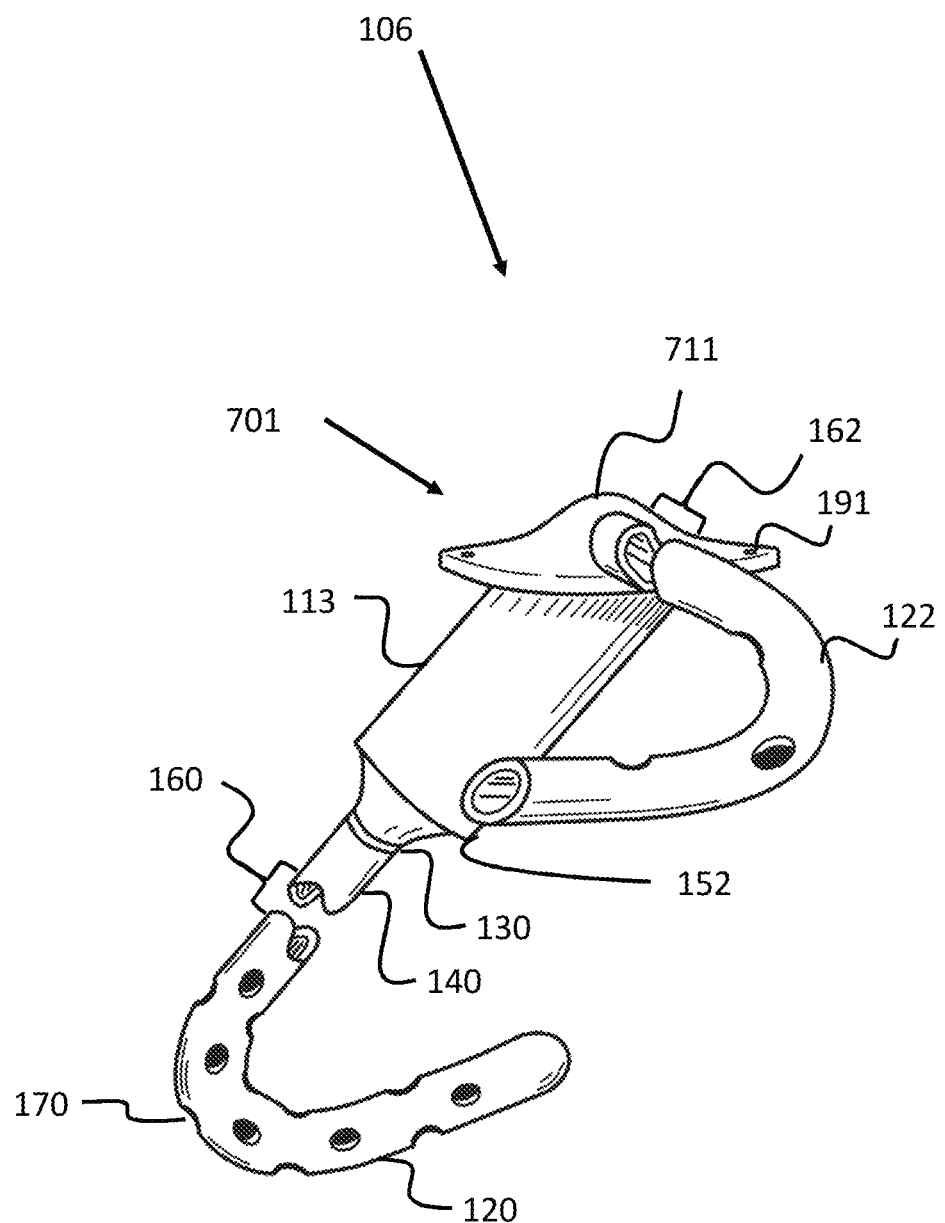
FIG. 19 shows a perspective view of an alternative automatic intercostal pump-based fluid management system including a pump that is shaped to better accommodate the transition from the pleural space to subcutaneous tissues, to provide an arbitrary orientation angle of the pump relative to the chest wall, to provide additional features to secure the automatic intercostal pump-based fluid management system in place, and to better prevent displacement once placed (inlet and outlet tubes represented schematically shortened for illustrative purposes)

Another solution to better accommodate the transition between the pleural cavity and the subcutaneous tissues as well as provide for stabile positioning is shown in FIG. 17. In this embodiment, the transitioning chamber 701 is a rounded, lozenge shaped feature that is configured for and capable of engaging with the rib cage and helps maintain stable positioning of the intercostal pump 113 in the intercostal space between a first rib and a second rib as well as orientation of the intercostal pump 113 relative to the chest wall, in this case the transitioning chamber 701 provides for a roughly 90 degree (or other suitable angle) transition from the pump inlet end 140 of the first tube 120 to the pump outlet end 142 of the second tube 122 and stability of the intercostal pump. While the roughly 90 degree transition shown in FIG. 17 may be desirable, alternative transition angles are also possible and one such alternative is shown in FIG. 18. Additionally, the general shape of the transitioning chamber 701 can vary as demonstrated by the example flanged-mushroom shape shown in FIG. 19. Additional stability features may be provided such as holes 191 in the flanged-mushroom shaped transitioning chamber which allow for tissue ingrowth or for passage of suture to secure the transitioning automatic intercostal pump-based fluid management system 106 in place. In such cases, the flange portion of the mushroom shape, or at least a portion thereof, may be configured such that the holes 191 in the flange portion do not pierce the interior space 330.

e. Pleuroperitoneal Automatic Intercostal Pump with Manual Assist

Figure 20A:
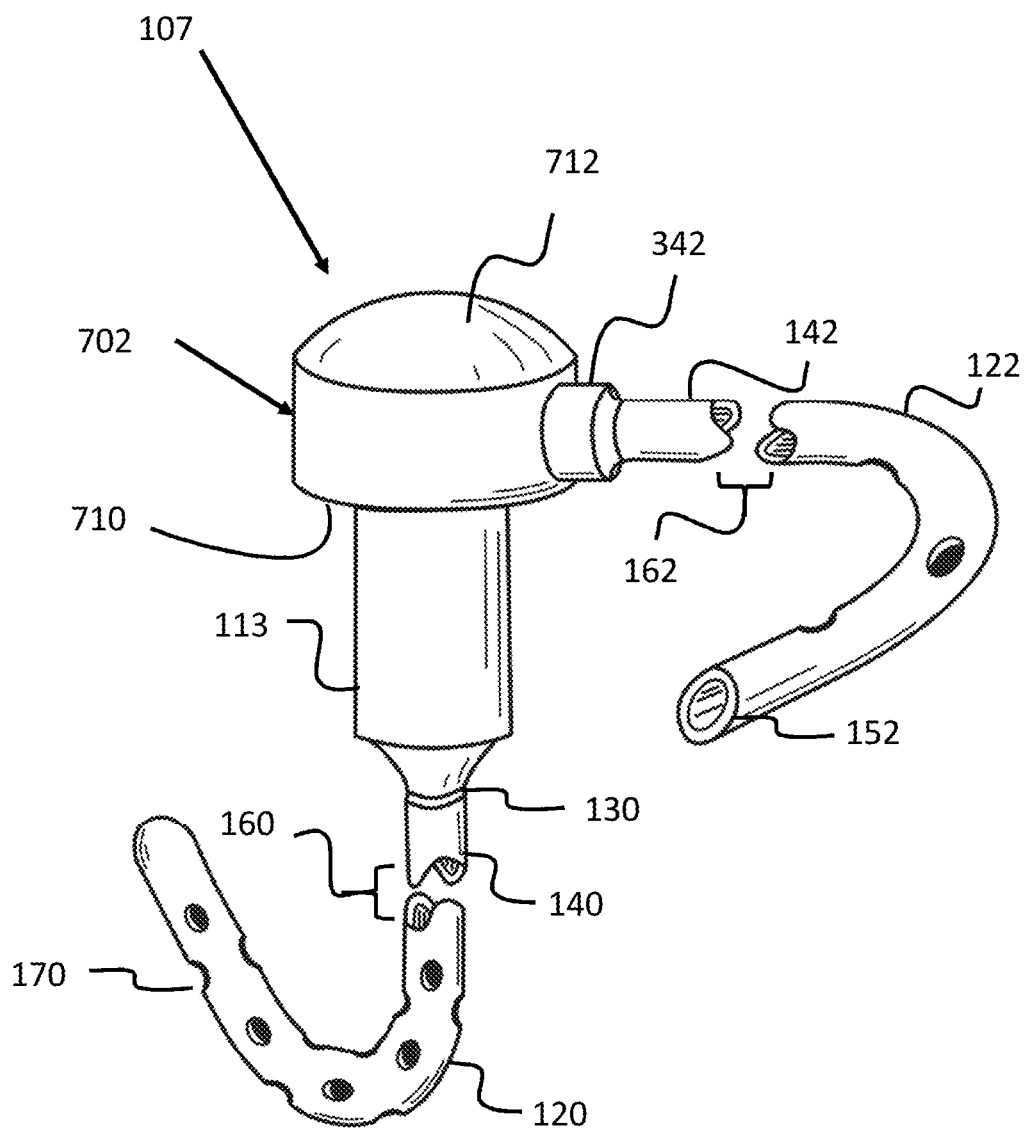
FIG. 20A shows a perspective view of an automatic intercostal pump-based fluid management system including a pump for placement in the intercostal space and a dome shaped diaphragm that can be manually actuated to improve overall function of the pump system.
Figure 20B:
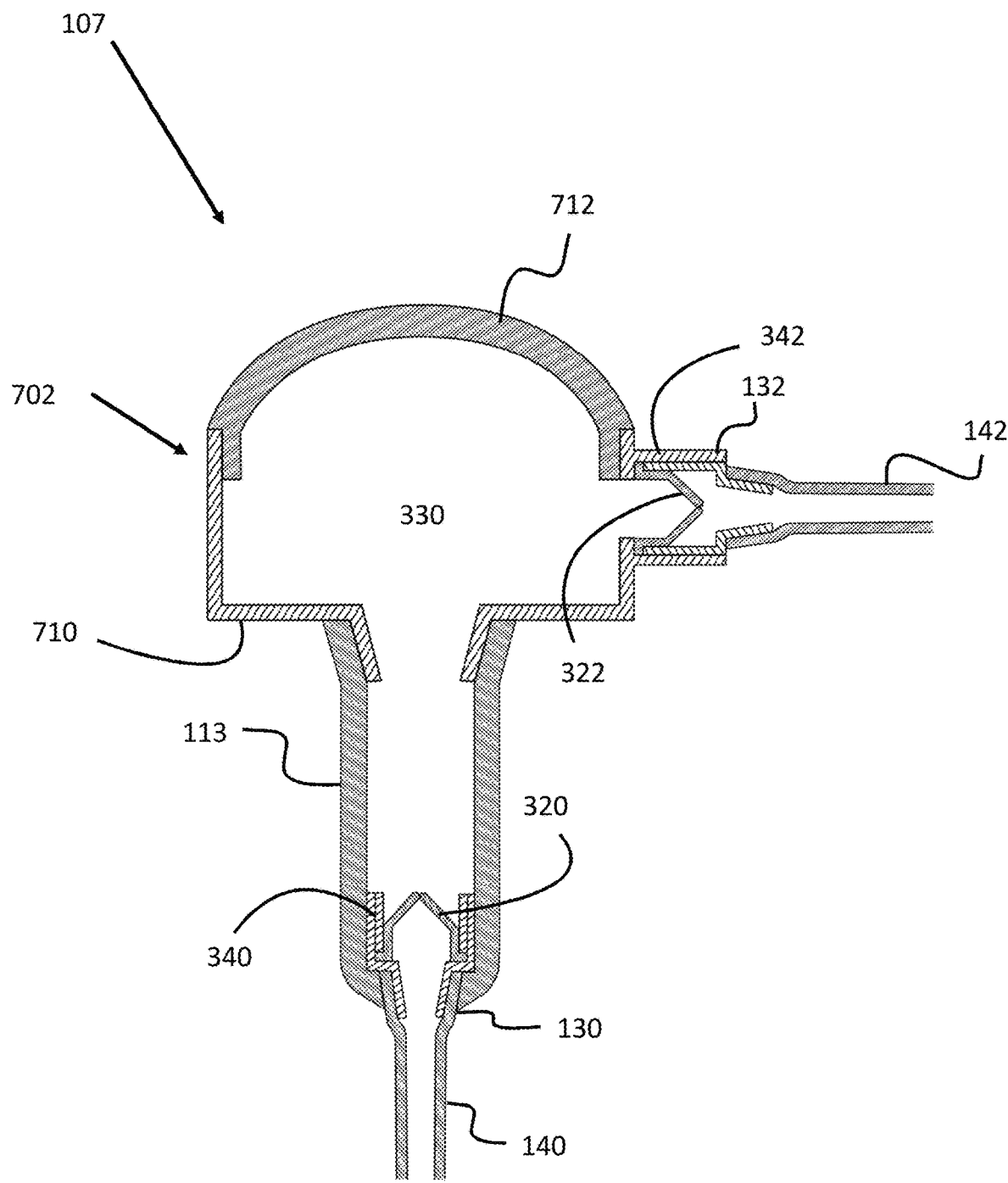
FIG. 20B shows a cross-sectional schematic view of the pump of the automatic intercostal pump-based fluid management system shown in FIG. 20A.
Figure 21:
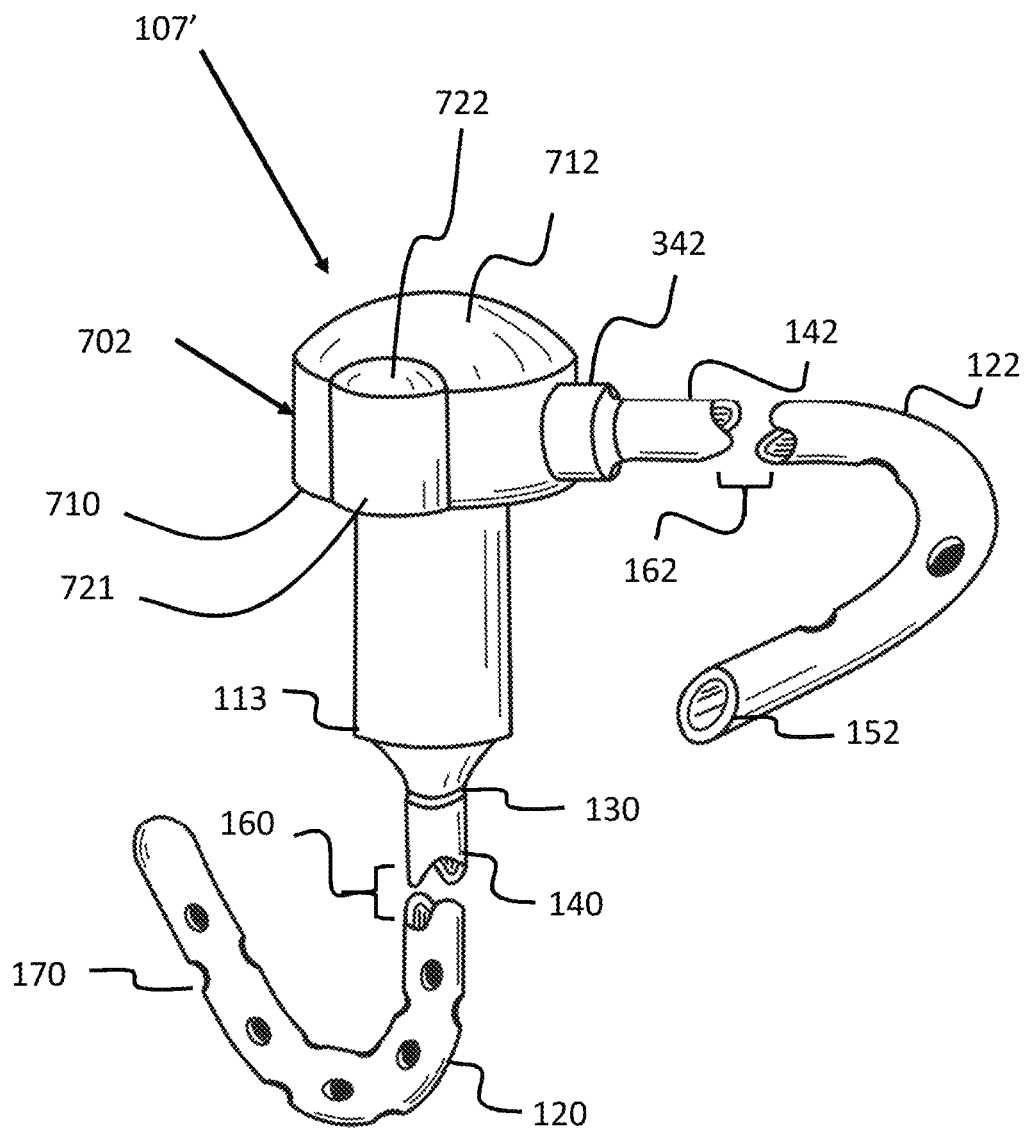
FIG. 21 shows a perspective view of an automatic intercostal pump-based fluid management system including a pump for placement in the intercostal space, a dome shaped diaphragm that can manually actuated to improve overall function of the pump system, and an access port with a dome shaped septum that can be punctured to allow access to the interior of the automatic intercostal pump-based fluid management system.

Another automatic intercostal pump that accommodates the transition between the pleural cavity and the subcutaneous tissues and provides for manual assistance to the pumping action is shown in FIG. 20A. A transitioned automatic intercostal pump-based fluid management system with manual assist 107 includes an intercostal pump 113 connected to a transitioning chamber 702 to better accommodate the transition from the pleural space to subcutaneous tissues. The transitioning chamber 702 is shown as a domed cylinder with intercostal pump 113 connected to a flat first end 710 of the cylinder, a domed second end 712 on an opposite side of the cylinder from the flat first end 710, and an outlet one-way valve frame 342 integrated into or attached to the wall of the cylinder. In this embodiment, the body of the transitioning chamber 702 as well as the first flat end 710 may be constructed of any relatively stiff, or non-flexible material such as nylon, acrylic, polycarbonate, PEEK, ABS, PET, stainless steel, or other suitable material, and the domed second end 712 may be constructed of a polyurethane, silicone, polyvinyl chloride, latex rubber, or other appropriately resilient material that is deformable but returns to its original shape. When placed in a patient, the intercostal pump 113 is placed in an intercostal space between a first rib and a second rib and the transitioning chamber 702 is placed in the subcutaneous tissues under the skin and on the outer portion of the rib cage. In this configuration and placement, as the patient breathes, the intercostal pump 113 is cyclically compressed and decompressed by the first rib and second rib as described, for example, with respect to FIG. 11A and FIG. 11B thereby automatically providing a continuous pumping action on the pump and flow of fluid from the pleural cavity to the peritoneal cavity. Additionally, in this configuration and placement, the transitioning chamber 702 is located on the outside of the rib cage and provides for up to a 90 degree transition from the pump inlet end 140 of the first tube 120 to the pump outlet end 142 of the second tube 122 to better accommodate the transition from the pleural cavity to the subcutaneous tissues. The flat first end 710 of the cylinder provides a stable interface of the transitioning chamber 702 with the rib cage, and the resilient domed end 712 faces outward from the rib cage and is positioned in the subcutaneous tissues under the skin. The subcutaneous resilient domed end 712 is therefore accessible for cyclic (or non-cyclic) manual compression that can provide additional pumping action when desired to supplement fluid flow from the pleural cavity to the peritoneal cavity. Additionally, if the material used to make the resilient domed end 712 of the transitioning chamber 702 is capable of self-sealing after a puncture, the interior 330 of the transitioned automatic intercostal pump-based fluid management system with manual assist 107 can be accessed for example by passing a needle through the resilient and self-sealing material of the domed end 712 to aspirate fluid or to instill anticoagulants, fibrinolytics, and/or other medicaments. While the body and first flat end of the transitioning chamber 702 may be constructed of any relatively stiff, or non-flexible material, it can additionally or alternatively be made of a more flexible material as desired. FIG. 20B shows a cross-sectional schematic view of the pump 113 and transitioning chamber 702 of the transitioning automatic intercostal pump-based fluid management system 107.

f. Pleuroperitoneal Automatic Intercostal Pump with Access Ports

Another automatic intercostal pump that accommodates the transition between the pleural cavity and the subcutaneous tissues and provides an accessory access port 721 is shown in FIG. 20A. A transitioned automatic intercostal pump-based fluid management system with access ports 107' includes an intercostal pump 113 connected to a transitioning chamber 702 to better accommodate the transition from the pleural space to subcutaneous tissues. The transitioning chamber 702 is shown as a domed cylinder with intercostal pump 113 connected to a flat first end 710 of the cylinder, a domed second end 712 on an opposite side of the cylinder from the flat first end 710, and an outlet one-way valve frame 342 integrated into or attached to the wall of the cylinder. An accessory access port 721 is shown as a second domed cylinder with domed end 722 adjacent to the transitioning chamber 702. In this embodiment, the interior of the accessory access port 721 is in fluid communication with the interior 330 of the transitioning chamber which in turn is in fluid communication with the transitioning chamber 702. In this embodiment, the body of the transitioning chamber 702, the first flat end 710 of the transitioning chamber, and the cylinder of the accessory access port 721 may be constructed of any relatively stiff, or non-flexible material such as nylon, acrylic, polycarbonate, PEEK, ABS, PET, stainless steel, or other suitable material. The domed second end 712 of the transitioning chamber 702 may be constructed of polyurethane, silicone, polyvinyl chloride, latex rubber, or other appropriately resilient material that is deformable and returns to its original shape. The domed septum 722 of the accessory access port 721 may be constructed of certain types of polyurethane, silicone, latex rubber, or other appropriately self-sealing material that can be sharply punctured for access but is capable of sealing the puncture. When placed in a patient, the intercostal pump 113 is placed in an intercostal space between a first rib and a second rib and the transitioning chamber 702 is placed in the subcutaneous tissues under the skin and on the outer portion of the rib cage. In this configuration and placement, as the patient breathes, the intercostal pump 113 is cyclically compressed and decompressed by the first rib and second rib as described, for example, with respect to FIG. 11A and FIG. 11B, thereby automatically providing a continuous pumping action on the pump and flow of fluid from the pleural cavity to the peritoneal cavity. Additionally, in this configuration and placement, the transitioning chamber 702 is located on the outside of the rib cage and provides for up to a 90 degree transition from the pump inlet end 140 of the first tube 120 to the pump outlet end 142 of the second tube 122 to better accommodate the transition from the pleural cavity to the subcutaneous tissues. The flat first end 710 of the cylinder provides a stable interface of the transitioning chamber 702 with the rib cage, and the resilient domed end 712 faces outward from the rib cage and is positioned in the subcutaneous tissues under the skin. The subcutaneous resilient domed end 712 is therefore accessible for cyclic (or non-cyclic) manual compression that can provide additional pumping action when desired to supplement fluid flow from the pleural cavity to the peritoneal cavity. Additionally, the self-sealing domed septum 722 of the accessory access chamber 721 is accessible under the skin of the patient by puncture with a needle thereby connecting with the interior space 330 of the transitioning chamber 702 and directly to the outlet side of the inlet valve 320 and the inlet side of the outlet valve 322 in order to sample the contents within the interior space 330 or instill anticoagulants, fibrinolytics, and/or other medicaments into the interior space 330 of the transitioning chamber 702. It should be noted that during sampling from the interior space 330, a negative pressure may be generated during the sampling process causing the inlet valve 320 to open allowing fluid to flow from the pump inlet end 140 of the first tube 120 enabling indirect sampling of the contents within the first tube 120 as well. Similarly, during instillation of anticoagulants, fibrinolytics, and/or other medicaments into the interior space 330, a positive pressure may be generated during the instillation process causing the outlet valve 322 to open allowing fluid to flow into the pump outlet end 142 of the second tube 122 enabling delivered of anticoagulants, fibrinolytics, and/or other medicaments to the contents in the interior of the second tube 122 as well. While the body and first flat end of the transitioning chamber 702 may be constructed of any relatively stiff, or non-flexible material, it can additionally or alternatively be made of a more flexible material as desired.

Figure 22:
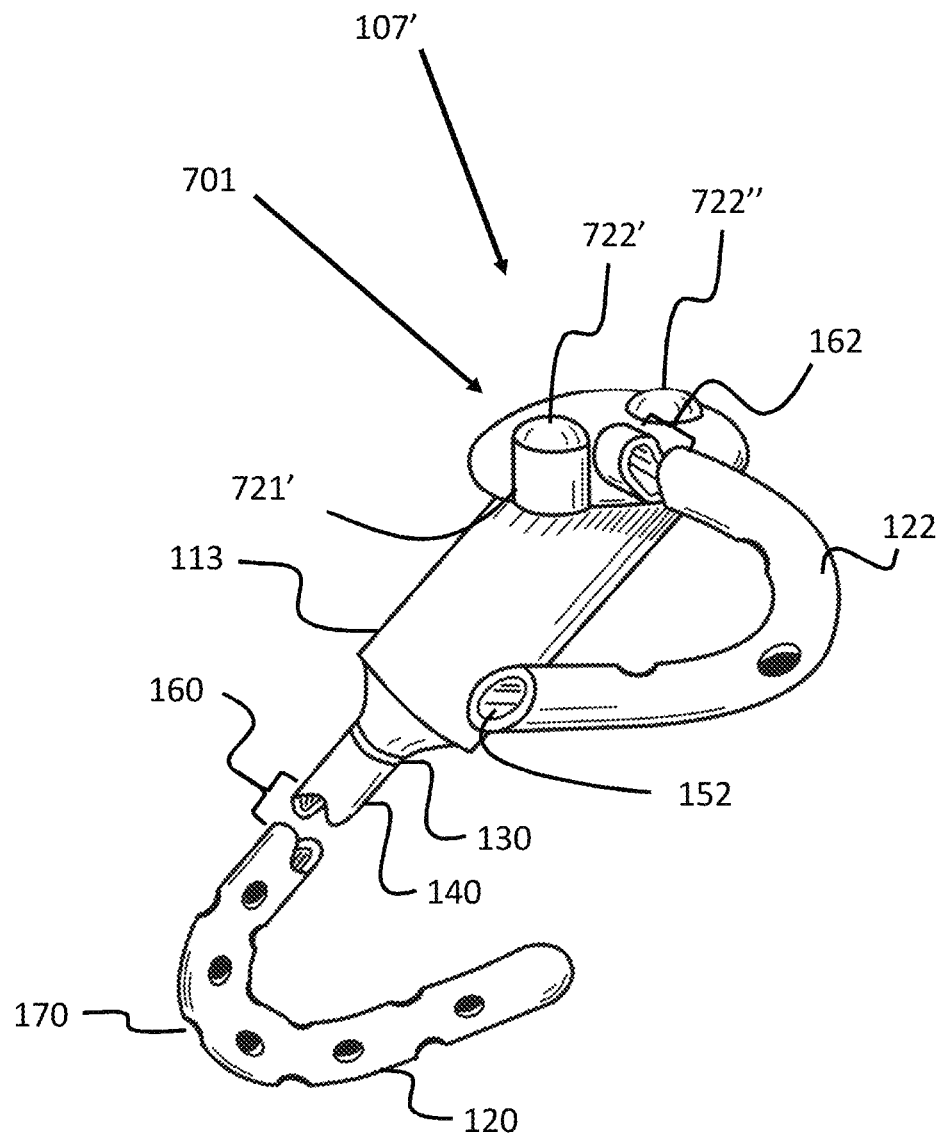
FIG. 22 shows a perspective view of an alternative automatic intercostal pump-based fluid management system including a pump for placement in the intercostal space, a lozenge shaped stability and orientation feature, and two access ports with dome shaped septums that can be punctured to allow access to different areas of the interior of the automatic intercostal pump-based fluid management system.

This concept of using accessory access ports to access the interior of the transitioned automatic intercostal pump-based fluid management system with access ports 107' can be taken further by providing multiple access ports. As seen in FIG. 22, for example, the transitioning chamber 701 is a rounded, lozenge shaped feature, or other suitably shaped feature, that is capable of engaging with the rib cage and thereby help maintain stable positioning of the intercostal pump 113 in the intercostal space between a first rib and a second rib as well as orientation of the intercostal pump 113 relative to the chest wall. There is a first accessory access chamber 721' with a self-sealing domed septum 722' that is in fluid communication with the interior 330 of the transitioning chamber 701 and a second accessory access chamber (not visible in FIG. 22) with a second self-sealing domed septum 722" that is in fluid communication with the interior of the pump inlet end 140 of the first tube 120. Therefore, by traversing the overlying skin and then the first self-sealing domed septum 722' of the first accessory access chamber 721', fluid can be sampled or anticoagulants, fibrinolytics, and/or other medicaments can be selectively instilled into the interior space 330 of the transitioning chamber 702. Similarly, by traversing the overlying skin and then the second self-sealing domed septum 722' of the second accessory access chamber, fluid can be selectively sampled or anticoagulants, fibrinolytics, and/or other medicaments can be instilled into the interior of the pump inlet end 140 of the first tube 120.

g. Pleuroperitoneal Electro-Mechanical Automatic Pump Designs

Figure 23A:
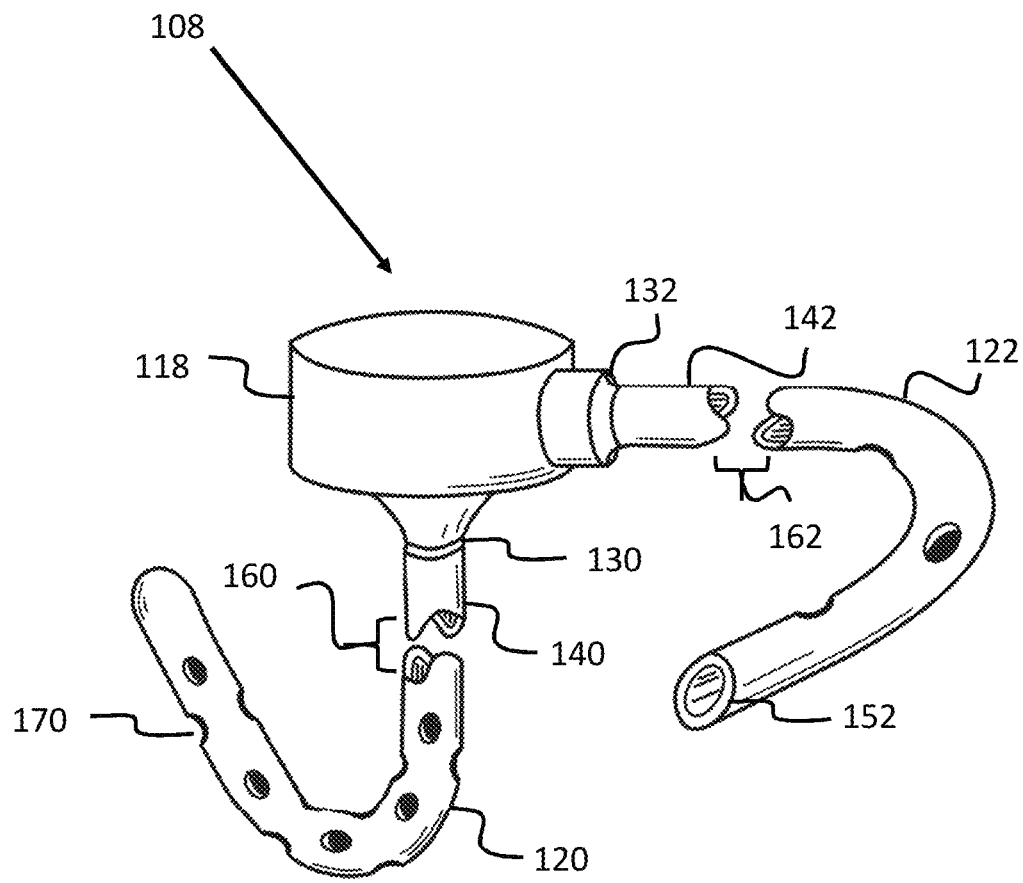
FIG. 23A shows a perspective view of an electro-mechanical automatic pump-based fluid management using a piezoelectric diaphragm.

With reference to FIG. 23A, an electro-mechanical automatic pump-based fluid management system 108 for the movement of fluid from a first body compartment to a second body compartment comprises a pump 118 that generally has an inlet 130 and an outlet 132 and is capable of moving fluid between the inlet 130 and outlet 132. The electro-mechanical automatic pump-based fluid management system 108 also comprises a first tube 120 and a second tube 122. Inlet 130 and outlet 132 each communicate between the interior and the exterior of pump 115 and are coupled to the first tube 120 and the second tube 122, respectively. In other words, inlet 130 and outlet 132 are configured so as to provide for fluid communication between first tube 120 and second tube 122, respectively, and an interior space of pump 118.

Further, first tube 120 may comprise multiple perforations or fenestrations 170 that allow for inlet of fluid into the first tube 120 and a pump-inlet end 140. Generally, first tube 120 is configured so that when in use the perforations 170 may be disposed in an area of a person's body from which fluid is to be drained. On the other hand, pump-inlet end 140 is coupled to inlet 130 of pump 118. The length of first tube 120 may vary, as depicted by length extension 160.

Similarly, second tube 122 comprises a pump-outlet end 142 and a tube-outlet end 152. Generally, second tube 122 is configured so that when automatic pump-based fluid management system 108 is in use, tube-outlet end 152 may be disposed in an area of a person's body to which fluid is to be drained. On the other hand, pump-outlet end 142 is coupled to outlet 132 of the pump 118. The length of second tube 122 may vary, as depicted by length extension 162.

Figure 23B:
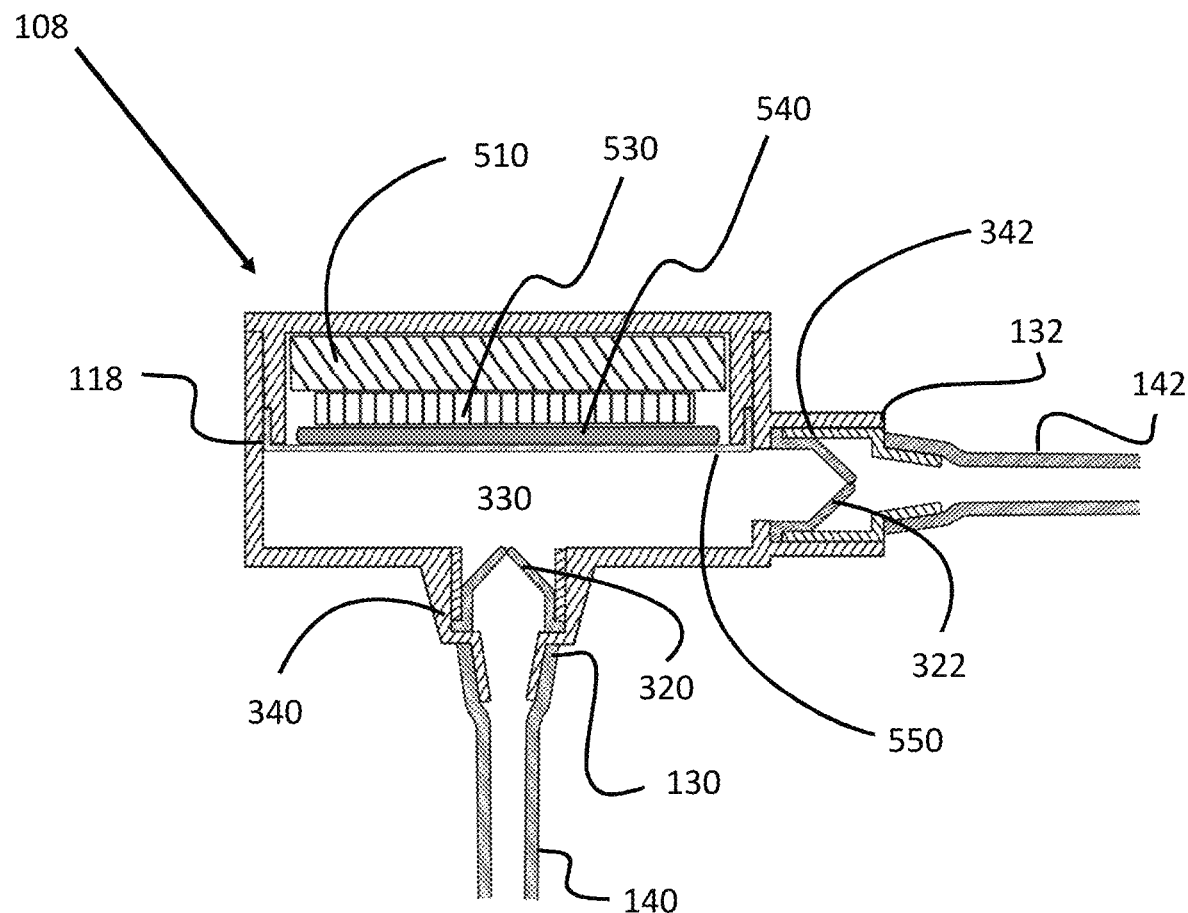
FIGS. 23B, 23C, and 23D show cross-sectional schematic views of the pump of the electro-mechanical automatic pump-based fluid management system shown in FIG. 23A.

FIG. 23B shows a cross-sectional schematic view of electro-mechanical automatic pump-based fluid management system 108 in an inactive state with both an inlet one-way valve 320 and an outlet one-way valve 322 closed. The electro-mechanical pump 118 comprises a pump wall that encloses an interior space 330 with inlet one-way valve 320 and outlet one-way valve 322.

Inlet valve 320 may be situated in the interior space 330 of the pump body in general proximity to inlet 130. Inlet one-way valve 320 may be any suitable one-way valve, such as any one-way valve described herein, and may, for example, be made of silicone. Inlet one-way valve 320 is configured so as to preclude fluid movement from the interior space 330 of pump 118 to inlet 130. At the same time, inlet one-way valve 320 is configured to allow fluid movement from inlet 130 to the interior space 330 of electro-mechanical pump 118. In other words, inlet one-way valve 320 is in fluid communication with inlet 130 so as to provide generally for one-way fluid movement from inlet 130 to interior space 330 of electro-mechanical pump 118.

Correspondingly, outlet one-way valve 322 may be situated in the interior space 330 of the pump body in general proximity to outlet 132. Outlet one-way valve 322 may be any suitable one-way valve, such as any one-way valve described herein, and may, for example, be made of silicone. Outlet one-way valve 322 is configured so as to allow fluid movement from the interior space 330 of electro-mechanical pump 118 to outlet 132. At the same time, outlet one-way valve 322 is configured to preclude or substantially preclude fluid movement from outlet 132 to the interior space 330 of electro-mechanical pump 118. In other words, outlet one-way valve 322 is in fluid communication with outlet 132 so as to provide generally for one-way fluid movement from interior space 330 of electro-mechanical pump 118 to outlet 132.

An inlet one-way valve frame 340 and an outlet one-way valve frame 342 may be integrated into or attached with the body of the electro-mechanical pump 118 and are on the outer perimeter of inlet one-way valve 320 and outlet one-way valve 322. Additionally, the size and shape of the inlet one-way valve frame 340 and outlet one-way valve frame 342 can be chosen to provide joining points or interconnectable joints between the first tube 120 and second tube 122.

Note that, although inlet one-way valve 320 and outlet one-way valve 322 are depicted as situated within the interior space 330 of intercostal pump 118, alternative placement of the valves may be desirable as well. For example, one of, or both of, inlet one-way valve 320 and outlet one-way valve 322 might be situated exterior to the pump body, perhaps within inlet tube 120 and outlet tube 122, respectively, or between inlet tube 120 and the pump body or outlet tube 122 and pump body, respectively. The particular placement of the valves need not be critical, so long as they sufficiently provide substantially for one-way fluid flow into and out of intercostal pump 111.

In electro-mechanical pump 118, a liquid impermeable membrane 550 separates the interior 330 that is in fluid communication with the inlet one-way valve 320 and the outlet one-way valve 322 from a compartment which contains a battery 510, a controller 530, and an electro-mechanical actuator 540. In electro-mechanical pump 118, the electro-mechanical actuator 540 can be a piezoelectric diaphragm connected to the membrane 550, activated and inactivated by the controller 530, and both the piezoelectric diaphragm 540 and the controller 530 may be powered by the battery 510. As shown in FIG. 23B, the piezoelectric diaphragm 540 is in an inactive state, and both the inlet one-way valve 320 and outlet one-way valve 322 are closed.

Figure 23C:
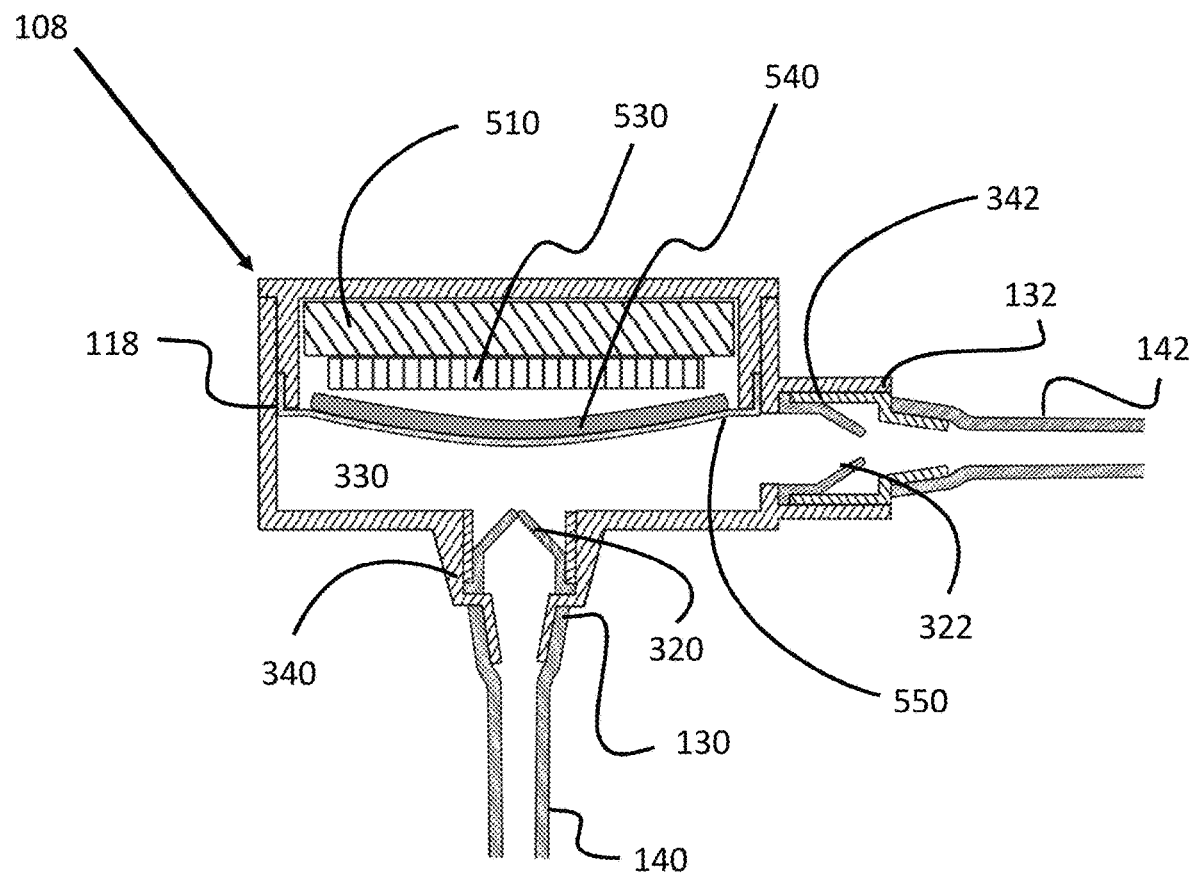
Figure 23D:
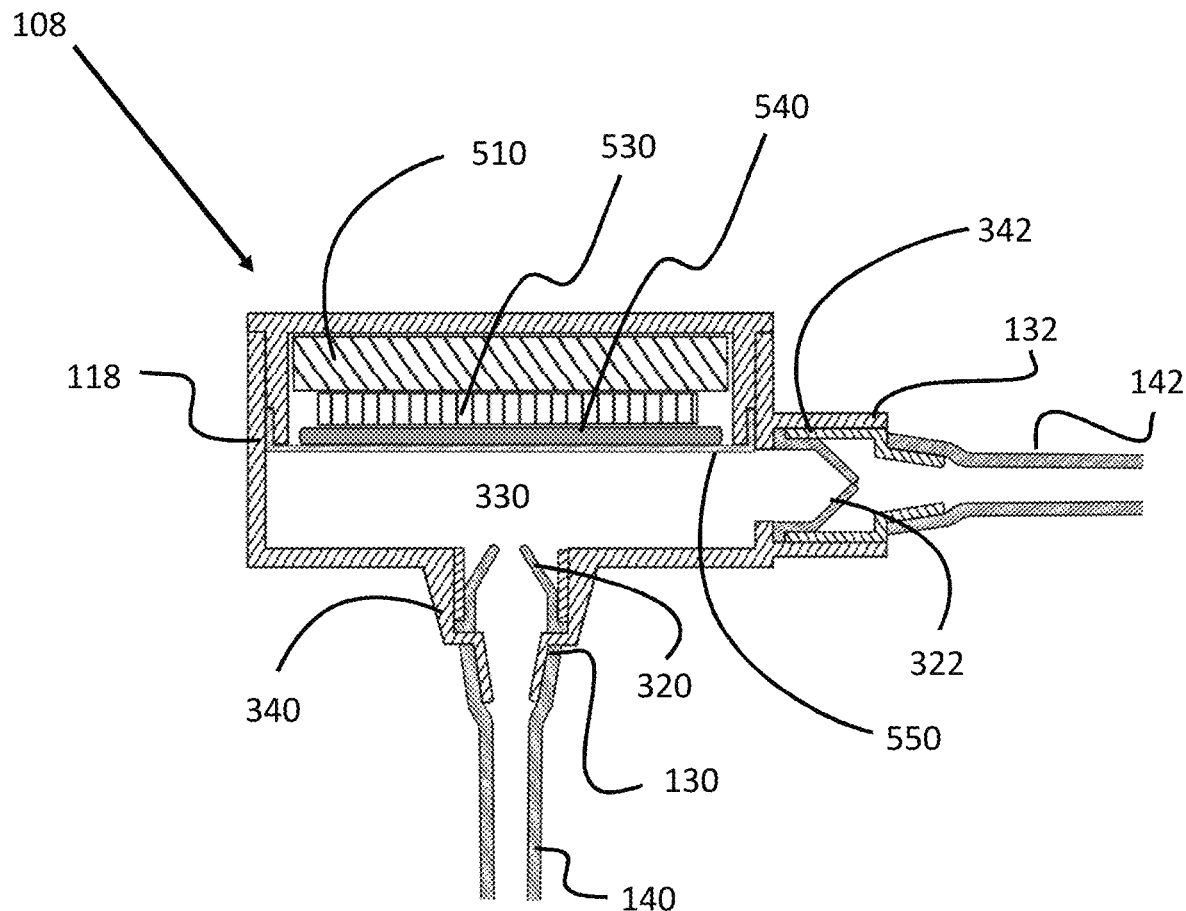

When the controller 530 activates the piezoelectric diaphragm 540, as shown in FIG. 23C, the piezoelectric diaphragm 540 changes shape deforming the membrane 550 such that it impinges on the interior 330 of the electro-mechanical pump 118. This decreases the volume available for fluids in the interior 330, increases the pressure within the interior 330, and opens the outlet one-way vale 322 so that fluid moves from the interior 330 of the electro-mechanical pump 118 to the pump-outlet end 142 of the second tube 122 and eventually to the tube-outlet end 152 of the second tube 122. When the controller 530 inactivates the piezoelectric diaphragm 540, as shown in FIG. 23D, the piezoelectric diaphragm 540 returns to its original shape and the membrane 550 returns to its original shape. This increases the volume available for fluids in the interior 330 of the electro-mechanical pump 118 and decreases the pressure within the interior 330, thereby closing the outlet one-way valve 322 and opening the inlet one-way vale 320 so that fluid moves from inside of the pump-inlet end 140 of the first tube 120 to the interior 330 of the electro-mechanical pump 118. In this way, cyclic activation and inactivation of the piezoelectric diaphragm 540 causes fluid to be pumped.

In the specific setting of recurrent malignant pleural effusions that require treatment to control symptoms, at the end of a 12-week period of daily drainage, 25% of patients will have died and 50% of patients will have stopped draining fluid because the pleural cavity will have achieved pleurodesis secondary to repeated drainage [Wahidi M W, Randomized trial of pleural fluid drainage frequency in patients with malignant pleural effusions. AJRCCM 2017; 195: 1050-1057]. Stated another way, a system that can provide daily removal of effusion fluid from the pleural cavity will provide adequate treatment for 75% of patients with malignant pleural effusions. The volume of pleural effusion fluid that must be drained from the pleural cavity can vary greatly from patient-to-patient and from day-to-day, and in general, effusion drainage volumes decrease with each subsequent drainage. Typical effusion drainage volumes may start at approximately 500 ml per day and decrease to approximately 0 ml per day over 12 weeks. Assuming the decrease in drainage volume is described by the first-order differential equation given below $$\frac{dV}{dt} = -\lambda V$$

where dV is the drainage volume during an infinitesimal time interval dt,
V is the drainage volume, and
λ is the decay constant,
solving this equation yields an exponential decay in drainage of the form $$V(t) = V_0 e^{-\lambda t}$$

where V(t) is the drainage volume on a given day t, and
$V_0$ is the drainage volume on day 0.
Assuming a starting drainage volume of 500 ml on day 0 and a decay constant of 1/28, the drainage will be less than 25 ml per day after 12 weeks and the total volume drained will be 13.5 liters. Similarly, if the starting drainage was excessive with 1000 ml on day 0, assuming the same decay constant of 1/28, the drainage will be less than 50 ml per day after 12 weeks and the total volume drained will be 27.1 liters. So, designing a system that is capable of pumping 27 liters of fluid over a 12-week period would satisfy the drainage requirements of the vast majority of patients with malignant pleural effusions during that 12-week period and at least 75% of patients would require no further interventions. Desired daily drainage values, based on this relationship or any other desired relationship, can be placed into a look-up table that is used to control an electro-mechanical pump. By having the volume pumped each day decrease over time can extend the life of the power supply.

The work that a pump must perform to move fluid through a tube from a first location to a second location can be derived from Bernoulli's Equation and is given as $$E_{Pump} = \frac{P_2 - P_1}{\rho} + \frac{1}{2}(\bar{v}_2^2 - \bar{v}_2^2) + g(z_2 - z_1) + E_{friction}$$

where
$E_{Pump}$ is the energy per unit mass the pump imparts on the fluid,
$P_1$ is the pressure at location 1,
$P_2$ is the pressure at location 2,
$\rho$ is the density of the fluid,
$\bar{v}_1$ is the average velocity of the fluid at location 1,
$\bar{v}_2$ is the average velocity of the fluid at location 2,
g is the force of gravity acting on the fluid,
$z_1$ is the height of the fluid at location 1,
$z_2$ is the height of the fluid at location 2,
$E_{friction}$ is energy loss due to friction as the fluid flows through the tube.

The major frictional losses to move fluid through a tube from a first location to a second location can be derived as $$E_{friction} = \frac{2f\bar{v}^2 L}{d}$$

where
$E_{friction}$ is the major energy loss due to friction as the fluid flows through the tube,
f is the coefficient of friction for the tube,
$\bar{v}$ is the average velocity of the fluid as it passes through the tube,
L is the length of the tube, and
d is the diameter of the tube.

Combining these two equations yields $$E_{Pump} = \frac{P_2 - P_1}{\rho} + \frac{1}{2}(\bar{v}_2^2 - \bar{v}_2^2) + g(z_2 - z_1) + \frac{2f\bar{v}^2 L}{d}.$$

To determine the energy required for an electro-mechanical pump 118 to move effusion fluid from a first area 220 that is the patient's pleural cavity to a second area 230 that is the patient's peritoneal cavity, we can consider a simplified situation where the first location and second location are both at the same height, where the fluid is static in the first location, and the pressure in the second location is higher than in the first location. In this situation, the pump energy equation simplifies to $$E_{Pump} = \frac{P_2 - P_1}{\rho} + \frac{\bar{v}_2^2}{2} + \frac{2f\bar{v}_2^2 L}{d}.$$

If we substitute volumetric flow in for average velocity in a tube with the relationship $$\bar{v}_2 = \frac{k4Q_2}{\pi d^2}$$

where
$Q_2$ is the volumetric flow rate of fluid through the tube, and
k is a correction factor accounting for the velocity profile,
the pump energy equation becomes $$E_{Pump} = \frac{P_2 - P_1}{\rho} + 8\frac{k^2 Q_2^2}{\pi^2 d^4} + 32\frac{fLk^2 Q_2^2}{\pi^2 d^5}.$$

Examination of the above equation shows the heavy dependence of the pump energy on the diameter of the tube when the tube diameter is relatively small. The following example representative values for these terms for the pleural cavity, peritoneal cavity, and potential design characteristics may be considered:
$P_1$, the pleural cavity pressure=–5 cmH$_2$O=–490 Pa,
$P_2$, the peritoneal cavity pressure=+20 cmH$_2$O=1961 Pa,
$\rho$, the density of the effusion fluid=1,000 kg/m$^3$,
$Q_2$, the average volumetric flow of the fluid at location 2 flow rate of 100 ml/min=1.667×10–6 m$^3$/s,
f, the coefficient of friction of the silicone tube=0.5,
k, the correction factor for turbulent flow=1,
L, the length of tubing connecting first and second location=30 cm=0.3 m, and
d, the diameter of the tubing=3 mm=0.003 m.

Substituting these example representative values into the equation yields $$E_{Pump} = \frac{1961 + 490}{1000} + 8\frac{(1)^2(1.667 \times 10^6)^2}{\pi^2(0.003)^4} + 32\frac{(0.5)(0.3)(1)^2(1.667 \times 10^6)^2}{\pi^2(0.003)^5}$$

$$E_{Pump} = 2.451 + 0.0278 + 5.562 = 8.041 \frac{N \cdot m}{kg}.$$

Hence, for each kilogram mass of effusion fluid moved from a first area 220 of a patient to a second area 230 of the patient with the assumptions outlined above, 8.041 J of energy is expended according to this simplified model.

To further refine the model, if a second frictional term is added to the above equations to account for a narrow connection that is 1 cm in length and 1 mm in diameter, then $$E_{Pump} = 2.451 + 0.0278 + 5.562 + 45.05 = 53.09 \frac{N \cdot m}{kg}.$$

It is interesting to note that the 1 cm length and 1 mm diameter connection contributes 8 times (8×) the frictional energy as does the 30 cm length of 3 mm diameter tubing. From this it is seen that for each kilogram mass of effusion fluid moved from a first area 220 of a patient to a second area 230 of the patient with the modified assumptions outlined above, which include a 1 cm tube and a 1 mm narrowing, 53.09 J of energy is expended. Further, for an electro-mechanical pump 118 operating at an efficiency of 50%, 106.2 J of energy must be supplied to move 1 kg of effusion fluid. Thus, over the first 3 months, where it is expected that 27 liters of effusion fluid must be moved, a power supply should desirably be capable of delivering a minimum of 2,866.9 J. Additionally, to allow for a greater pressure gradient between the first area 220 and the second area 230 of the patient, for higher frictional losses in the tube (particularly given the diameter of the tube), and for lower efficiency, the power source should be able to preferably supply a minimum of about 5,000 J of energy, or more preferably supply a minimum of about 10,000 J of energy or even about 15,000 J of energy. For reference, a AA battery rated at 2800 mAH and operating at 1.5 V contains 15,120 J of energy.

Furthermore, with the strong dependence of $E_{Pump}$ on the diameter of the tubes and connections required to transfer fluid between the first area 220 and the second area 230, it may be desirable for the electro-mechanical automatic pump-based fluid management system 108 to have all tube, connection, and opening diameters (notwithstanding the operation, e.g., opening and closing, of the one-way valves) equal to or greater than 1 mm, preferably equal to or greater than 2 mm, more preferably equal to or greater than 3 mm or even up to or greater than 4 mm. Alternatively, it may be desirable to limit the length of connections and openings that are smaller than 1 mm to be equal to or less than 1 cm in length, preferably equal to or less than 0.5 cm in length, and more preferably equal to or less than 0.2 cm in length.

Activation and operation of the electro-mechanical pump 118 can be optimized based on the fluid movement requirements between the first area 220 and the second area 230 of the patient. For the pleural cavity to peritoneal cavity outlined above, requirements for effusion fluid movement may be 500 ml on day one and decrease over time to less than 25 ml by day 84, or 1 liter on day one and decrease over time to less than 50 ml by day 84. For such situations, the controller 530 can be programmed to turn the pump on for a period of time based on the pump's capacity that will pump a desired volume of fluid on day one and then decrease the time that the pump is on for each subsequent day according to, for example, the relationship $$V(t)=V_0 e^{-\lambda t}$$

where
$V_0$, as an example, is 1 liter,
$\lambda$ is 1/28, and
t is the number of days post implantation.

Alternatively, pump-on time can be based on a look-up table that is populated with a desired daily drainage volume. The electro-mechanical pump 118 may be turned on once per day to pump the entire desired volume of fluid at once or the total pump-on time may be divided throughout the day. For example, the electro-mechanical pump 118 may be turned on once every hour to pump about 1/24 of the total desired daily drainage volume. Other patterns of pump-on and pump-off times may also be used.

Furthermore, the controller 530 can be designed with sensing features that can monitor fluid flow when the electro-mechanical pump 118 is on, and once fluid flow has stopped, the electro-mechanical pump 118 can be turned off. For example, if the initially estimated or desired volume of fluid flow on day 1 is 1 liter, but flow stops after 550 ml of fluid has been pumped, the controller 530 can be programmed to shut the electro-mechanical pump 118 off. Alternatively, the electro-mechanical pump 118 can simply be turned on every hour or other suitable period(s) of time and left on until fluid flow drops below some pre-determined value, such as but not limited to, 1 ml/min or 5 ml/min. Additionally, the controller 530 can be designed with sensing features that can monitor pressure inside the pump while the electro-mechanical pump 118 is turned on and programmed to turn the electro-mechanical pump 118 off when the pressure inside the pump drops below a predefined value. For example, the controller may turn the electro-mechanical pump 118 off when the pressure drops below about 5 $cmH_2O$, below about 0 $cmH_2O$, below about −5 $cmH_2O$, below about −10 $cmH_2O$, or below about −20 $cmH_2O$.

In the electro-mechanical pump 118, the electro-mechanical actuator 540 was described as a piezoelectric diaphragm, but alternative actuators for a diaphragm pump, such as but not limited to, an electric motor and cam among other alternatives, could be used to achieve a similar action. Indeed, the electro-mechanical pump 118 could be a gear pump, screw pump, rotary vane pump, diaphragm pump, piezoelectric diaphragm pump, plunger pump, peristaltic pump, lobe pump, piston pump, centrifugal pump, or any other type of pump.

h. Pleuroperitoneal Electro-Mechanical and Automatic Intercostal Pump Design

Figure 24A:
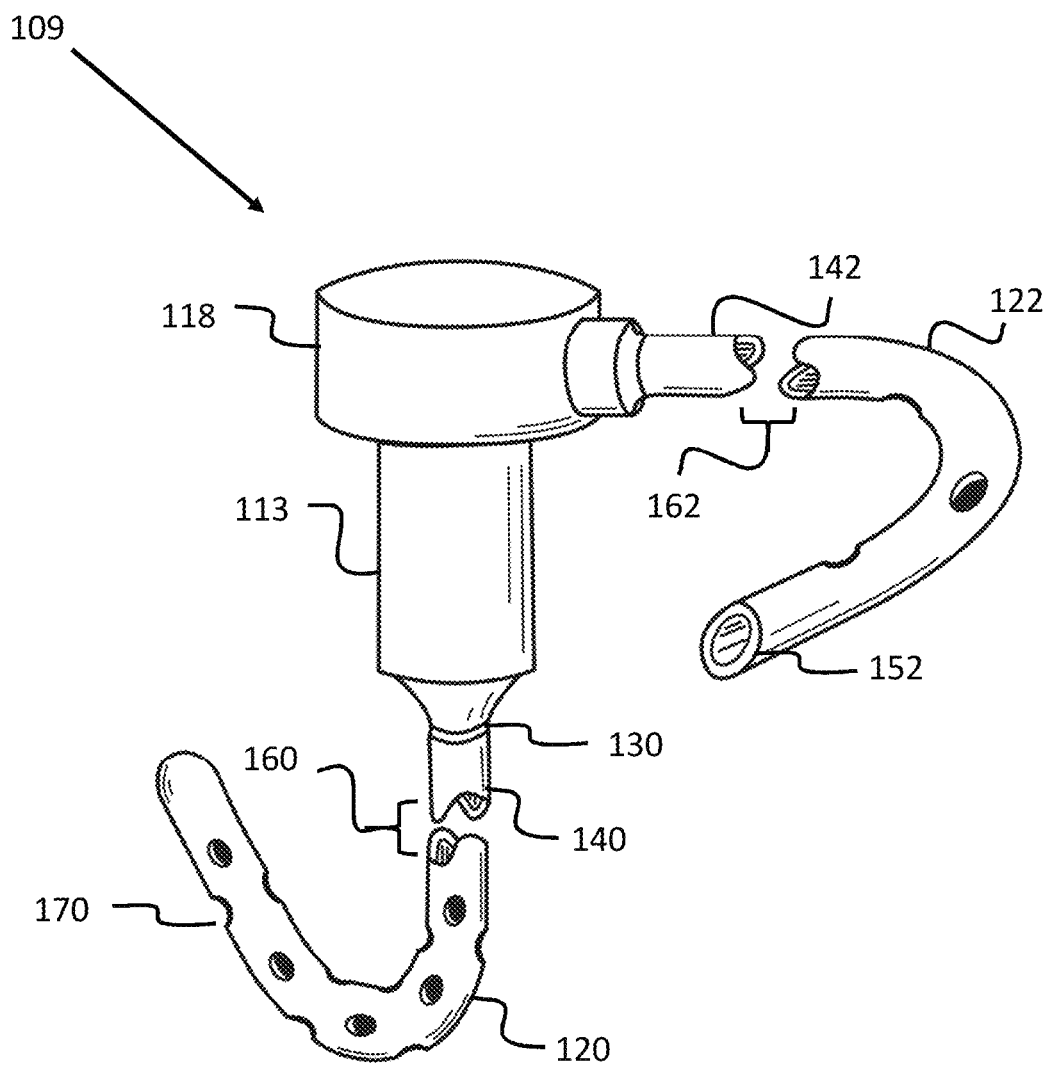
FIG. 24A shows a perspective view of an automatic intercostal pump-based fluid management system including a pump for placement in the intercostal space and an electro-mechanical pump that can be activated to improve overall function of the pump system.
Figure 24B:
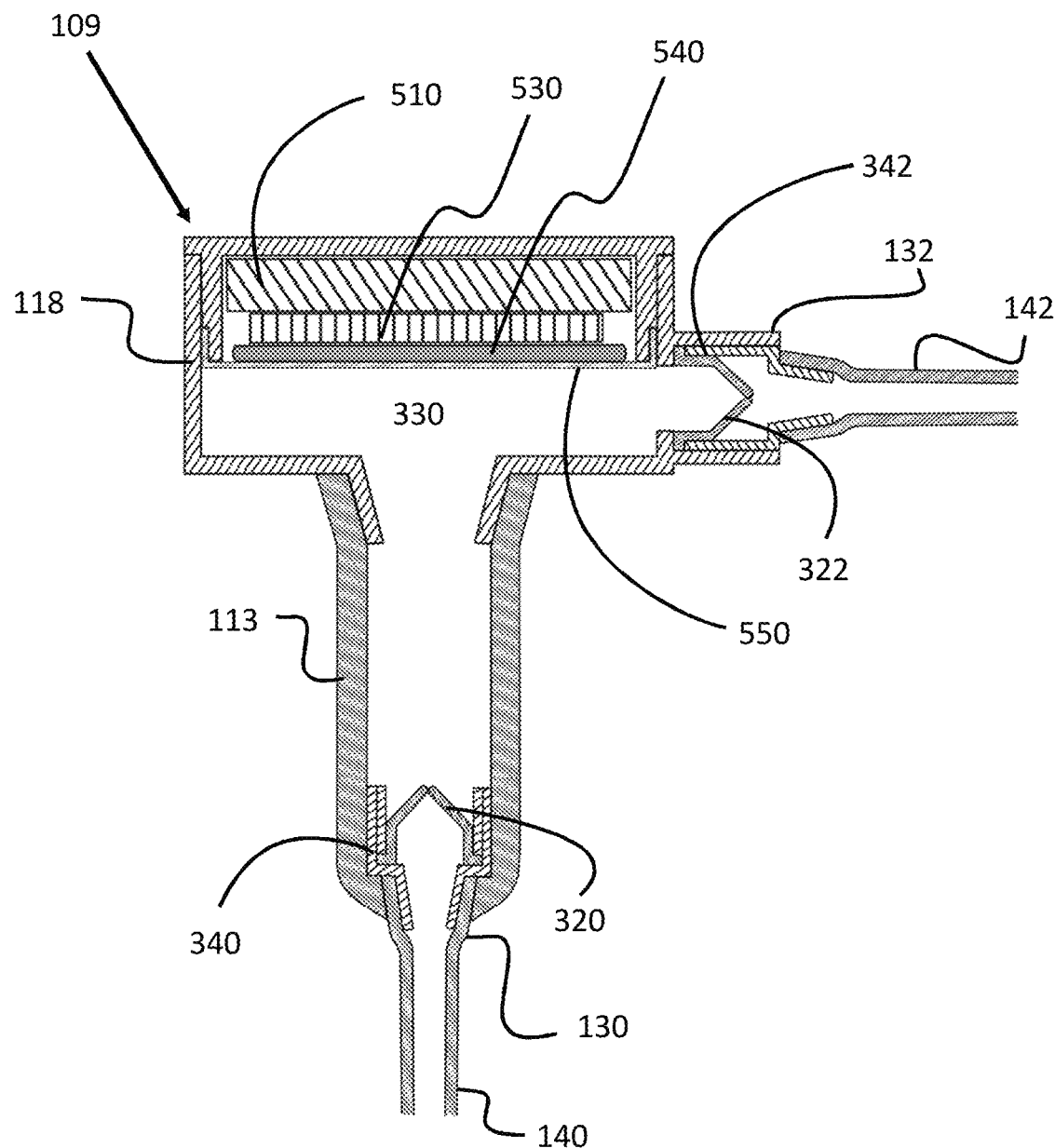
FIG. 24B shows a cross-sectional schematic view of the pump of the automatic intercostal pump-based fluid management system shown in FIG. 24A.

With reference to FIG. 24A and FIG. 24B, a combination electro-mechanical and automatic intercostal pump-based fluid management system 109 is shown that incorporates an intercostal pump 113, which operates as described with reference for example to FIG. 11A and FIG. 11B, and an electro-mechanical pump 118 as described with reference for example to FIGS. 23A through 23D. These pumps may share a common interior 330, inlet one-way valve 320, and outlet one-way valve 322. In operation, the intercostal pump 113 may be cyclically compressed and decompressed between a first rib and second rib to produce continual fluid flow between pump inlet 130 and pump outlet 132. The electro-mechanical pump 118 can be configured to supplement fluid flow as needed.

5. Other Automatic Pump Based Fluid Management Systems

A fluid management system that includes automatic pump 110 may be used for draining fluid from and to various areas of a patient's body. That is, a fluid management system that includes the intercostal pump described herein is not limited to uses involving draining fluid from a patient's pleural cavity to the patient's peritoneal cavity.

One example of an alternative use of a fluid management system that incorporates the intercostal pump described herein is draining fluid from a patient's cerebrospinal region. According to this alternative use, tube 120 may be configured to extend from automatic pump 110 to the patient's cerebrospinal region such that tube-inlet end 150 may be disposed in the patient's cerebrospinal region. In this way, excess cerebrospinal fluid may be drained.

Another example of an alternative use of a fluid management system that incorporates the inter-costal pump described herein is draining fluid from a patient's pericardial region.

Other alternative uses are certainly possible. In general, a fluid management system that incorporates the intercostal pump described herein may be used to drain fluid to and from any combination of regions in a patient's body with which fluid communication can be sufficiently established with any automatic intercostal pump-based fluid management system 100 described herein.

6. Automatic Pump Based Fluid Management System with Reservoir

Figure 25:
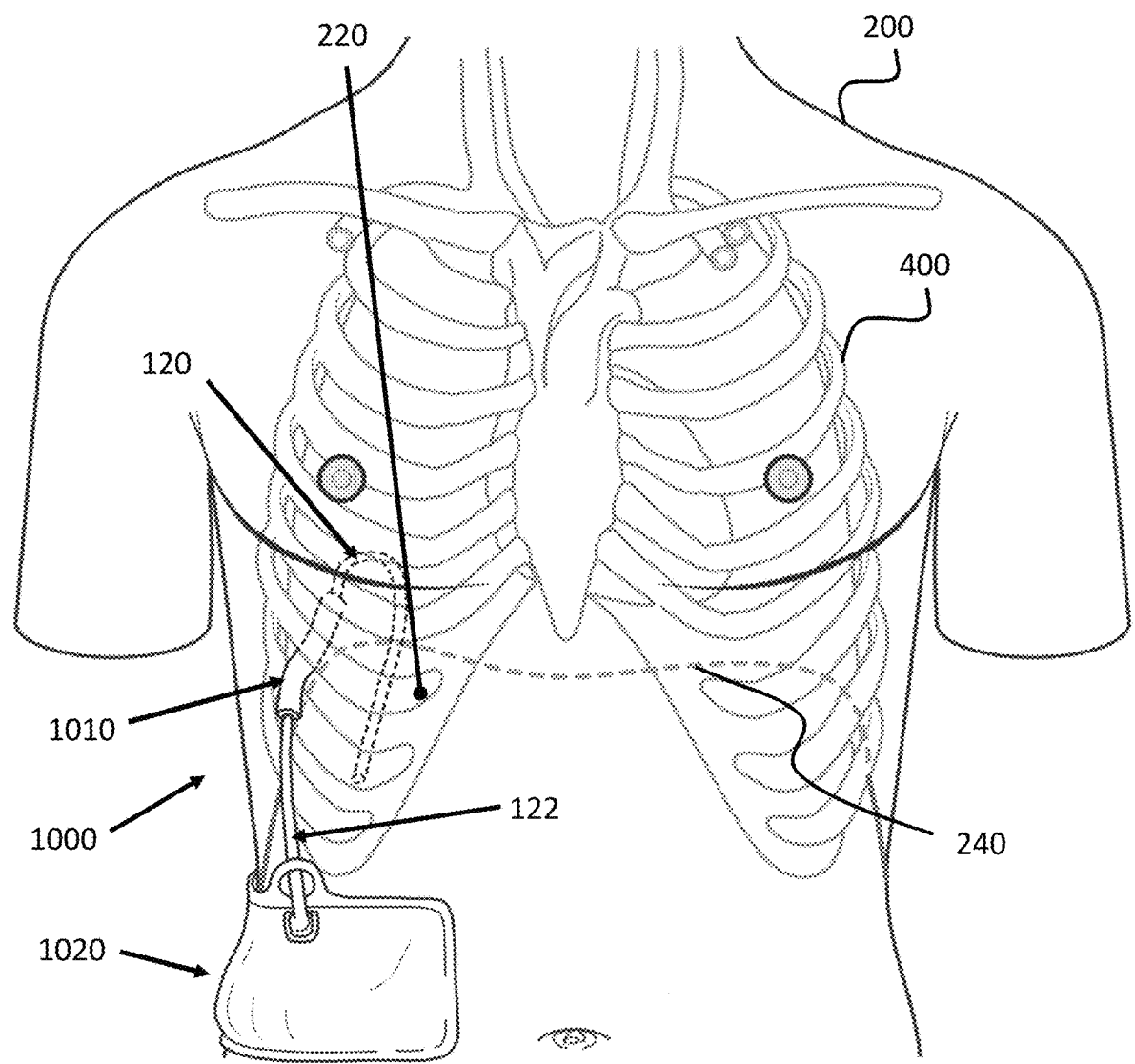
FIG. 25 shows an automatic intercostal pump-based fluid management system, implanted in a patient, and coupled with an external reservoir.

With reference to FIG. 25, automatic intercostal pump-based fluid management system 1000 is shown implanted with at least a portion of the pump 1010 and a first tube 120 within the patient's body 200 and at least a portion of the second tube 122 located outside of the patient's body providing for drainage of fluid from a first area 220 within the patient's body to an external reservoir 1020 located outside the patient's body. In one embodiment, as in the example embodiment depicted in FIG. 25, fluid is drained from a patient's pleural cavity 220 to the external reservoir 1020.

In an embodiment, automatic intercostal pump 1010 is configured so that it may be placed, at least partially, in the intercostal region between two ribs. In other words, when implanted, intercostal pump 1010 extends through the patient's intercostal space, or at least a portion thereof. Accordingly, first tube 120, and correspondingly, pump inlet 130, are disposed on the interior of the patient's rib cage. Second tube 122, and correspondingly, pump outlet 132, are disposed on the exterior of the patient's rib cage. In this way, upon breathing and the corresponding compression/decompression of the rib cage, patient 210 will automatically cause intercostal pump 1010 to operate (e.g., "pump"). This configuration allows the patient to ambulate with minimal hardware while fluid in the pleural cavity is being actively pumped out.

Figure 26A:
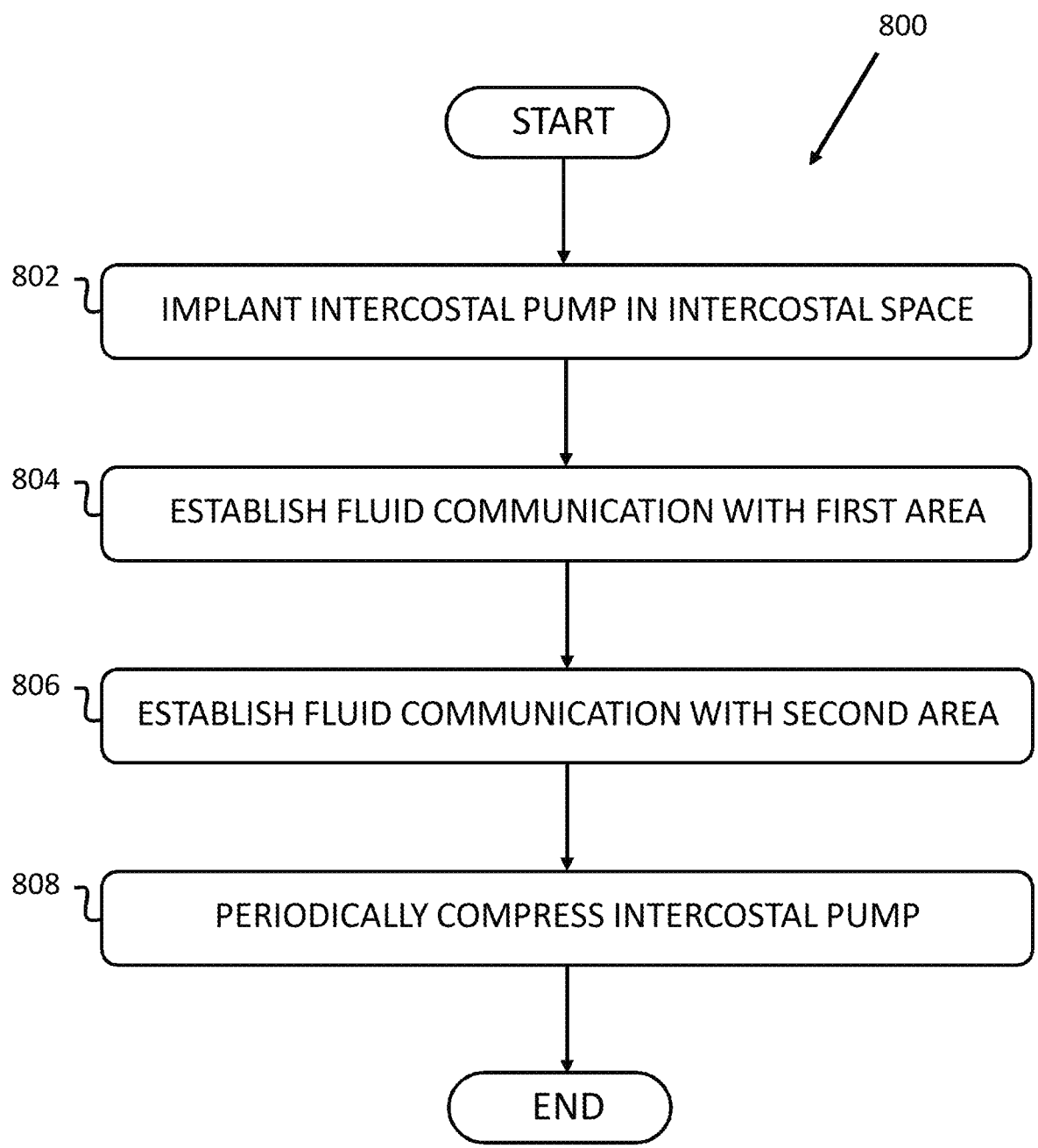
FIGS. 26A and 26B show methods for draining body fluid using an automatic intercostal pump-based fluid management system.

7. Methods for Draining Fluid in a Patient's Body Using an Automatic Pump-Based Fluid Management System A method draining a fluid from a first area of a patient's or person's body to a second area of the patient's or person's body may be carried out generally by implanting and using any of the various automatic pump-based fluid management systems described herein. With reference to FIG. 26A and method 800, with respect to an example of a method for draining pleural fluid, at step 802, the intercostal pump, e.g., 110, 111, 112, etc., of an automatic pump-based fluid management system, such as any of the various embodiments described herein, is implanted in an intercostal space of a patient such that the pump may be compressed between a first rib, e.g., 412, and second rib, e.g., 414. The intercostal pump, e.g., 110, 111, 112, etc., may be implanted using any suitable known or yet to be discovered surgical techniques. At step 804, fluid communication is established between a first area of a patient and the inlet 130 of intercostal pump, e.g., 110, 111, 112, etc. For example, first tube, e.g., 120, may be extended from a patient's pleural cavity to inlet 130. At step 806, fluid communication is established between a second area of a patient and the outlet 132 of intercostal pump, e.g., 110, 111, 112, etc. For example, second tube, e.g., 122, may be extended from outlet 132 to a patient's peritoneal cavity. At step 808, the intercostal pump, e.g., 110, 111, 112, etc., is periodically compressed and/or electro-mechanically pumped, depending on which of the various embodiments described above is utilized, to move fluid from the first area of the patient via the first tube, through the intercostal pump, and into the second area of the patient via the second tube.

Figure 26B:
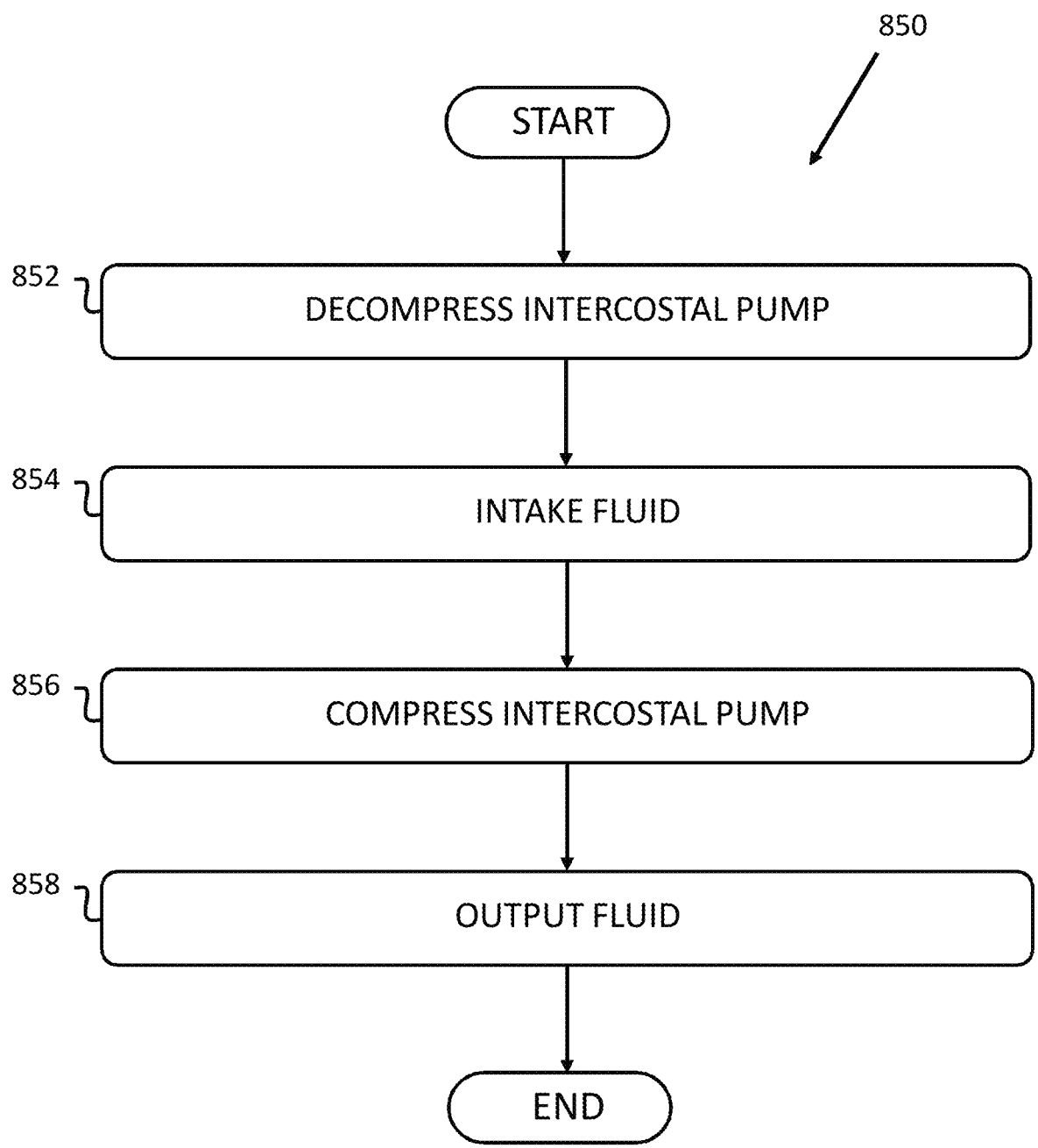

For example, intercostal pump, e.g., 110, 111, 112, etc., may be compressed between first rib, e.g., 412, and second rib, e.g., 414, during a patient's breath cycle. Specifically, with reference to FIG. 26B and method 850, at step 852, the intercostal pump, e.g., 110, 111, 112, etc., is decompressed. For example, the intercostal pump, e.g., 110, 111, 112, etc., is initially compressed between first rib 412 and second rib 414 while a patient's ribs are in a contracted stated (i.e., the patient has previously exhaled). As the patient inhales, the rib cage is expanded and first rib 412 and second rib 414 move away from one another. As a result, the intercostal pump, e.g., 110, 111, 112, etc., is decompressed. At step 854, the intercostal pump, e.g., 110, 111, 112, etc., intakes fluid. That is, as a result of decompressing intercostal pump, e.g., 110, 111, 112, etc., at step 852, a pumping force draws fluid into the interior space, e.g., 330, of the intercostal pump, e.g., 110, 111, 112, etc. At step 856, the intercostal pump, e.g., 110, 111, 112, etc., is compressed. For example, the intercostal pump, e.g., 110, 111, 112, etc., is compressed between first rib 412 and second rib 414 as a result of the patient's rib cage being contracted (i.e., the patient exhales). As the patient exhales, the rib cage is contracted and first rib 412 and second rib 414 move towards one another. As a result, the intercostal pump, e.g., 110, 111, 112, etc., is compressed. At step 858, the intercostal pump, e.g., 110, 111, 112, etc., outputs fluid. That is, as a result of compressing intercostal pump, e.g., 110, 111, 112, etc., at step 856, a pumping force forces fluid out of the interior space, e.g., 330, of the intercostal pump, e.g., 110, 111, 112, etc. In some methods, an electro-mechanical pump, e.g., 118, may be used alternatively to or additionally to the intercostal pump, e.g., 110, 111, 112, etc.

8. Miscellaneous

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall effect or result as if absolute and total completion were obtained. The use of "substantially" or "generally" is equally applicable when used in a negative connotation to refer to the complete or near complete lack of an action, characteristic, property, state, structure, item, or result.

Unless otherwise specified, as used herein, the phrases "at least one of [X] and [Y]" or "at least one of [X] or [Y]," where [X] and [Y] are different components that may be included in an embodiment of the present disclosure, means that the embodiment could include component [X] without component [Y], the embodiment could include component [Y] without component [X], or the embodiment could include both components [X] and [Y]. Similarly, when used with respect to three or more components, such as "at least one of [X], [Y], and [Z]" or "at least one of [X], [Y], or [Z]," the phrases mean that the embodiment could include any one of the three or more components, any combination or sub-combination of any of the components, or all of the components.

Example embodiments of an automatic pump-based fluid management system are described above. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

The invention claimed is:
1. A pump-based fluid management system comprising:
a pump body having an interior chamber in fluid communication with an inlet and an outlet;

an inlet one-way valve in general proximity to the inlet configured to allow fluid movement from the inlet to the interior chamber and at least substantially preclude fluid movement from the interior chamber to the inlet; and an outlet one-way valve in general proximity to the outlet configured to allow fluid movement from the interior chamber to the outlet and at least substantially preclude fluid movement from the outlet to the interior chamber;

wherein the pump body is comprised of a resilient flexible material selected such that when the pump body is implanted between adjacent ribs of a patient user, expansion and contraction of the patient user's rib cage causes decompression and compression, respectively, of the pump body and automatic pumping of fluid received at the inlet through the pump body and out the outlet; and wherein the pump body further comprises a manually depressible portion comprised of a deformable material that returns to its original shape after deformation, the manually depressible portion configured to face outward from the rib cage of the patient user when the pump body is implanted between adjacent ribs of the patient user, the manually depressible portion further configured, upon being depressed, to pump fluid from the interior chamber to the outlet.

2. The pump-based fluid management system of claim 1, wherein the manually depressible portion comprises a generally domed-shaped portion of the pump body.

3. The pump-based fluid management system of claim 2, wherein the generally domed-shape portion is comprised of a self-sealing material.

4. The pump-based fluid management system of claim 1, further comprising:
a first tube configured to extend from the inlet and allow fluid movement from a first body area of the patient user to the inlet; and
a second tube configured to extend from the outlet and allow fluid movement from the outlet to a second body area of the patient user.

5. The pump-based fluid management system of claim 1, wherein at least one of the inlet one-way valve and the outlet one-way valve is configured to reseal with a differential back pressure of less than about 15 cmH$_2$O.

6. The pump-based fluid management system of claim 5, wherein the differential back pressure to reseal the at least one of the inlet one-way valve and the outlet one-way valve is less than about 5 cmH$_2$O.

7. The pump-based fluid management system of claim 5, wherein both the inlet one-way valve and the outlet one-way valve are configured to resist deformation from an applied back pressure once resealed.

8. The pump-based fluid management system of claim 7, wherein an applied back pressure of 50 cmH$_2$O on the inlet one-way valve or the outlet one-way valve correspondingly produces a deformation of the inlet one-way valve or the outlet one-way valve resulting in a back-flow of less than 200 microliters.

9. The pump-based fluid management system of claim 1, wherein at least a portion of the pump body comprises a generally cylindrical cross-section with an inner diameter of between about 4 mm and 10 mm and an outer diameter of between about 6 mm and 12 mm.

10. The pump-based fluid management system of claim 9, wherein the inner diameter is between about 6 mm and 7 mm and the outer diameter is between about 8 mm and 10 mm.

11. The pump-based fluid management system of claim 9, wherein the at least a portion of the pump body comprises a wall thickness of between about 0.7 mm and 1.0 mm.

12. The pump-based fluid management system of claim 1, wherein the pump body comprises at least one reinforcing member integrated into or attached to a wall of the pump body and configured to distribute a force applied to the wall along a length of the wall.

13. The pump-based fluid management system of claim 1, wherein at least a portion of the pump body is comprised of a self-sealing material.

14. The pump-based fluid management system of claim 1, further comprising an accessory access port in fluid communication with the interior chamber.

15. The pump-based fluid management system of claim 14, wherein the accessory access port is comprised of a self-sealing material.

16. The pump-based fluid management system of claim 1, wherein the pump body further comprises at least one of:
an orientation feature configured to interface with at least one rib of the patient user when the pump body is implanted between the adjacent ribs of the patient user and configured to orient the pump body at a desired angle relative the at least one rib; or
a transition portion that angles a first portion of the pump body comprising the inlet relative a second portion of the pump body comprising the outlet.

* * * * *

UNITED STATES PATENT AND TRADEMARK OFFICE
CERTIFICATE OF CORRECTION

PATENT NO. : 11,571,555 B2
APPLICATION NO. : 16/819352
DATED : February 7, 2023
INVENTOR(S) : Martin L. Mayse Page 1 of 1

It is certified that error appears in the above-identified patent and that said Letters Patent is hereby corrected as shown below:

In the Specification

In Column 10, Line 36, delete "120" and insert --220-- therefor

In Column 22, Line 6, delete "342" and insert --340-- therefor

In Column 22, Line 7, delete "122." and insert --120.-- therefor

In Column 23, Line 66, delete "414" and insert --412-- therefor

In Column 23, Line 67, delete "416," and insert --414,-- therefor

In Column 24, Line 1, delete "414" and insert --412-- therefor

In Column 24, Line 2, delete "416," and insert --414,-- therefor

In Column 28, Line 44, delete "115" and insert --118-- therefor

In Column 32, Line 29, delete "$1.667 \times 10\text{-}6$" and insert --$1.667 \times 10^{-6}$-- therefor Signed and Sealed this
Eighth Day of August, 2023

*Katherine Kelly Vidal*
Katherine Kelly Vidal
*Director of the United States Patent and Trademark Office*